US00RE46699E

(19) United States
(12) Reissued Patent
Woods et al.

(10) Patent Number: US RE46,699 E
(45) Date of Reissued Patent: Feb. 6, 2018

(54) LOW IMPEDANCE OXIDE RESISTANT GROUNDED CAPACITOR FOR AN AIMD

(71) Applicant: Greatbatch Ltd., Clarence, NY (US)

(72) Inventors: Jason Woods, Carson City, NV (US); Richard L. Brendel, Carson City, NV (US); Robert A. Stevenson, Canyon Country, CA (US); Christopher Michael Williams, Alden, NY (US); Robert Naugler, Eldersburg, MD (US); Christine A. Frysz, Orchard Park, NY (US)

(73) Assignee: Greatbatch Ltd., Clarence, NY (US)

(21) Appl. No.: 15/358,202

(22) Filed: Nov. 22, 2016

Related U.S. Patent Documents

Reissue of:
(64) Patent No.: 9,108,066
Issued: Aug. 18, 2015
Appl. No.: 14/202,653
Filed: Mar. 10, 2014

U.S. Applications:
(63) Continuation-in-part of application No. 13/873,832, filed on Apr. 30, 2013, now Pat. No. 8,868,189, and
(Continued)

(51) Int. Cl.
*A61N 1/00* (2006.01)
*A61N 1/375* (2006.01)
(Continued)

(52) U.S. Cl.
CPC ..... *A61N 1/3754* (2013.01); *H01G 2/02* (2013.01); *H01G 4/228* (2013.01); *H01G 4/35* (2013.01);
(Continued)

(58) Field of Classification Search
CPC ..... A61N 1/3754; H01G 4/40; H01G 4/35; H01G 2/02; H01G 4/228; H01R 13/7195; H03H 1/0007
(Continued)

(56) References Cited

U.S. PATENT DOCUMENTS 3,137,808 A 6/1964 Coda et al.
3,189,978 A 6/1965 Stetson
(Continued)

FOREIGN PATENT DOCUMENTS

EP 0243573 11/1987
EP 0145430 5/1991
(Continued)

OTHER PUBLICATIONS

Johnson, et al., "Characterization of the Relationship between MR-Induced Distal Tip Heating in Cardiac Pacing Leads and Electrical Performance of Novel Filtered Tip Assemblies", 17th Scientific Meeting & Exhibition of the International Society for Magnetic Resonance in Medicine, Honolulu, Hawaii, Apr. 2009, 307.

(Continued)

*Primary Examiner* — Jeffrey R Jastrzab
(74) *Attorney, Agent, or Firm* — Michael F. Scalise

(57) ABSTRACT

A hermetically sealed filtered feedthrough assembly for an AIMD includes an insulator hermetically sealed to a conductive ferrule or housing. A conductor is hermetically sealed and disposed through the insulator in non-conductive relation to the conductive ferrule or housing between a body fluid side and a device side. A feedthrough capacitor is disposed on the device side. A first low impedance electrical connection is between a first end metallization of the capacitor and the conductor. A second low impedance electrical connection is between a second end metallization of the capacitor and the ferrule or housing. The second low impedance electrical connection includes an oxide-resistant metal addition attached directly to the ferrule or housing and an electrical connection coupling the second end metallization electrically and physically directly to the oxide-resistant metal addition.

31 Claims, 38 Drawing Sheets

Related U.S. Application Data a continuation-in-part of application No. 13/743,276, filed on Jan. 16, 2013, now Pat. No. 9,233,253.

(60) Provisional application No. 61/841,419, filed on Jun. 30, 2013.

(51) Int. Cl.

| | |
|---|---|
| ***H01G 4/40*** | (2006.01) |
| ***H01R 13/7195*** | (2011.01) |
| ***H01G 4/228*** | (2006.01) |
| ***H01G 2/02*** | (2006.01) |
| ***H01G 4/35*** | (2006.01) |
| ***H03H 1/00*** | (2006.01) |
| ***H03H 7/01*** | (2006.01) |

(52) U.S. Cl.
CPC ..... *H01G 4/40* (2013.01); *H01R 13/7195* (2013.01); *H03H 1/0007* (2013.01); *H03H 7/1766* (2013.01); *H03H 2001/0042* (2013.01); *H03H 2001/0085* (2013.01)

(58) Field of Classification Search
USPC ..... 607/37, 38
See application file for complete search history.

(56) References Cited

U.S. PATENT DOCUMENTS

| | | | |
|---|---|---|---|
| 3,617,830 | A | 11/1971 | Perna |
| 3,681,612 | A | 8/1972 | Kinzler et al. |
| 3,745,430 | A | 7/1973 | Kerr et al. |
| 3,871,382 | A | 3/1975 | Mann |
| 3,961,294 | A | 6/1976 | Hollyday |
| 3,968,802 | A | 7/1976 | Ballis |
| 3,980,975 | A | 9/1976 | Maxon, Jr. et al. |
| 4,188,598 | A | 2/1980 | Hunt |
| 4,236,127 | A | 11/1980 | Scherba |
| 4,295,467 | A | 10/1981 | Mann et al. |
| 4,320,763 | A | 3/1982 | Money |
| 4,424,551 | A | 1/1984 | Stevenson et al. |
| 4,431,005 | A | 2/1984 | McCormick |
| 4,437,474 | A | 3/1984 | Peers-Trevarton |
| 4,445,501 | A | 5/1984 | Bresler |
| 4,572,198 | A | 2/1986 | Codrington |
| 4,585,001 | A | 4/1986 | Belt |
| 4,633,181 | A | 12/1986 | Murphy-Boesch et al. |
| 4,643,186 | A | 2/1987 | Rosen et al. |
| 4,654,880 | A | 3/1987 | Sontag |
| 4,672,972 | A | 6/1987 | Berke |
| 4,689,621 | A | 8/1987 | Kleinberg |
| 4,712,555 | A | 12/1987 | Thornander et al. |
| 4,746,864 | A | 5/1988 | Satoh |
| 4,754,752 | A | 7/1988 | Ginsburg et al. |
| 4,757,820 | A | 7/1988 | Itoh |
| 4,766,381 | A | 8/1988 | Conturo et al. |
| 4,788,980 | A | 12/1988 | Mann et al. |
| 4,799,499 | A | 1/1989 | Bisping |
| 4,813,429 | A | 3/1989 | Eshel et al. |
| 4,823,812 | A | 4/1989 | Eshel et al. |
| 4,832,023 | A | 5/1989 | Murphy-Chutorian et al. |
| 4,858,064 | A | 8/1989 | Segawa et al. |
| 4,858,623 | A | 8/1989 | Bradshaw et al. |
| 4,859,950 | A | 8/1989 | Keren |
| 4,932,411 | A | 6/1990 | Fritschy et al. |
| 4,940,052 | A | 7/1990 | Mann et al. |
| 4,944,298 | A | 7/1990 | Sholder |
| 4,960,106 | A | 10/1990 | Kubokawa |
| 4,989,608 | A | 2/1991 | Ratner |
| 4,991,580 | A | 2/1991 | Moore |
| 5,019,075 | A | 5/1991 | Spears et al. |
| 5,039,965 | A | 8/1991 | Higgins |
| 5,044,375 | A | 9/1991 | Bach, Jr. et al. |
| 5,052,404 | A | 10/1991 | Hodgson |
| 5,063,348 | A | 11/1991 | Kuhara et al. |
| 5,095,911 | A | 3/1992 | Pomeranz |
| 5,099,208 | A | 3/1992 | Fitzpatrick et al. |
| 5,167,233 | A | 12/1992 | Eberle et al. |
| 5,178,618 | A | 1/1993 | Kandarpa |
| 5,190,046 | A | 3/1993 | Shturman |
| 5,197,468 | A | 3/1993 | Proctor et al. |
| 5,209,233 | A | 5/1993 | Holland et al. |
| 5,211,165 | A | 5/1993 | Dumoulin et al. |
| 5,217,010 | A | 6/1993 | Tsitlik et al. |
| 5,222,506 | A | 6/1993 | Patrick et al. |
| 5,246,438 | A | 9/1993 | Langberg |
| 5,251,120 | A | 10/1993 | Smith |
| 5,268,810 | A | 12/1993 | Dimarco et al. |
| 5,271,400 | A | 12/1993 | Dumoulin et al. |
| 5,272,283 | A | 12/1993 | Kuzma |
| 5,300,108 | A | 4/1994 | Rebell et al. |
| 5,306,291 | A | 4/1994 | Kroll et al. |
| 5,307,808 | A | 5/1994 | Dumoulin et al. |
| 5,307,814 | A | 5/1994 | Kressel et al. |
| 5,318,025 | A | 6/1994 | Dumoulin et al. |
| 5,323,776 | A | 6/1994 | Blakeley et al. |
| 5,323,778 | A | 6/1994 | Kandarpa et al. |
| 5,331,505 | A | 7/1994 | Wilheim |
| 5,333,095 | A | 7/1994 | Stevenson et al. |
| 5,334,045 | A | 8/1994 | Cappa et al. |
| 5,334,193 | A | 8/1994 | Nardelia |
| 5,348,010 | A | 9/1994 | Schnall et al. |
| 5,352,979 | A | 10/1994 | Conturo |
| 5,358,515 | A | 10/1994 | Hurter et al. |
| 5,363,845 | A | 11/1994 | Chowdhury et al. |
| 5,365,928 | A | 11/1994 | Rhinehart et al. |
| 5,370,644 | A | 12/1994 | Langberg |
| 5,398,683 | A | 3/1995 | Edwards et al. |
| 5,400,787 | A | 3/1995 | Marandos |
| 5,404,880 | A | 4/1995 | Throne |
| 5,413,104 | A | 5/1995 | Buijs et al. |
| 5,419,325 | A | 5/1995 | Dumoulin et al. |
| 5,428,337 | A | 6/1995 | Vinciarelli et al. |
| 5,433,717 | A | 7/1995 | Rubinsky et al. |
| 5,437,277 | A | 8/1995 | Dumoulin et al. |
| 5,443,066 | A | 8/1995 | Dumoulin et al. |
| 5,443,489 | A | 8/1995 | Ben-Haim |
| 5,447,156 | A | 9/1995 | Dumoulin et al. |
| 5,450,090 | A | 9/1995 | Gels et al. |
| 5,451,232 | A | 9/1995 | Rhinehart et al. |
| 5,462,055 | A | 10/1995 | Casey et al. |
| 5,466,254 | A | 11/1995 | Helland |
| 5,470,345 | A | 11/1995 | Hassler et al. |
| 5,476,095 | A | 12/1995 | Schnall et al. |
| 5,476,483 | A | 12/1995 | Bornzin et al. |
| 5,491,300 | A | 2/1996 | Huppenthal et al. |
| 5,493,259 | A | 2/1996 | Blalock et al. |
| 5,498,261 | A | 3/1996 | Strul |
| 5,507,743 | A | 4/1996 | Edwards et al. |
| 5,512,825 | A | 4/1996 | Atalar et al. |
| 5,514,173 | A | 5/1996 | Rebell et al. |
| 5,540,679 | A | 7/1996 | Fram et al. |
| 5,545,201 | A | 8/1996 | Helland et al. |
| 5,558,093 | A | 9/1996 | Pomeranz |
| 5,578,008 | A | 11/1996 | Hara |
| 5,588,432 | A | 12/1996 | Crowley |
| 5,590,657 | A | 1/1997 | Cain et al. |
| 5,591,218 | A | 1/1997 | Jacobson |
| 5,620,476 | A | 4/1997 | Truex et al. |
| 5,623,241 | A | 4/1997 | Minkoff |
| 5,623,724 | A | 4/1997 | Gurkovich et al. |
| 5,629,622 | A | 5/1997 | Scampini |
| 5,650,759 | A | 7/1997 | Hittman et al. |
| 5,662,108 | A | 9/1997 | Budd et al. |
| 5,682,897 | A | 11/1997 | Pomeranz |
| 5,683,435 | A | 11/1997 | Truex et al. |
| 5,685,878 | A | 11/1997 | Falwell et al. |
| 5,697,958 | A | 12/1997 | Paul et al. |
| 5,699,801 | A | 12/1997 | Atalar et al. |
| 5,700,548 | A | 12/1997 | Warnier et al. |
| 5,706,810 | A | 1/1998 | Rubinsky et al. |
| 5,715,825 | A | 2/1998 | Crowley |
| 5,716,390 | A | 2/1998 | Li |
| 5,722,998 | A | 3/1998 | Prutchi et al. |

(56) References Cited

U.S. PATENT DOCUMENTS 5,735,884 A 4/1998 Thompson et al.
5,735,887 A 4/1998 Barreras et al.
5,741,321 A 4/1998 Brennen
5,751,539 A 5/1998 Stevenson et al.
5,757,252 A 5/1998 Cho et al.
5,759,202 A 6/1998 Schroeppel
5,765,779 A 6/1998 Hancock et al.
5,769,800 A 6/1998 Gelfand et al.
5,772,693 A 6/1998 Brownlee
5,775,338 A 7/1998 Hastings
5,779,669 A 7/1998 Haissaguerre et al.
5,782,891 A 7/1998 Hassler et al.
5,792,055 A 8/1998 McKinnon
5,800,467 A 9/1998 Park et al.
5,822,174 A 10/1998 Yamate et al.
5,824,026 A 10/1998 Diaz
5,824,029 A 10/1998 Weijand et al.
5,833,608 A 11/1998 Acker
5,836,992 A 11/1998 Thompson et al.
5,840,031 A 11/1998 Crowley
5,851,226 A 12/1998 Skubitz et al.
5,855,995 A 1/1999 Haq et al.
5,864,234 A 1/1999 Ludeke
5,868,674 A 2/1999 Glowinski et al.
5,879,347 A 3/1999 Saadat
5,891,134 A 4/1999 Goble et al.
5,896,267 A 4/1999 Hittman et al.
5,905,627 A 5/1999 Brendel et al.
5,916,162 A 6/1999 Snelten et al.
5,928,145 A 7/1999 Ocali et al.
5,928,159 A 7/1999 Eggers et al.
5,929,729 A 7/1999 Swarup
5,938,609 A 8/1999 Pomeranz
5,938,692 A 8/1999 Rudie
5,959,336 A 9/1999 Barsan
5,959,829 A 9/1999 Stevenson et al.
5,964,705 A 10/1999 Truwit et al.
5,973,906 A 10/1999 Stevenson et al.
5,973,907 A 10/1999 Reed
5,978,204 A 11/1999 Stevenson
6,004,269 A 12/1999 Crowley et al.
6,008,980 A 12/1999 Stevenson et al.
6,011,995 A 1/2000 Guglielmi et al.
6,026,316 A 2/2000 Kucharczyk et al.
6,027,500 A 2/2000 Buckles et al.
6,031,375 A 2/2000 Atalar et al.
6,031,710 A 2/2000 Wolf et al.
6,041,496 A 3/2000 Haq et al.
6,045,532 A 4/2000 Eggers et al.
6,052,614 A 4/2000 Morris, Sr. et al.
6,055,457 A 4/2000 Bonner
6,066,136 A 5/2000 Geistert
6,099,524 A 8/2000 Lipson et al.
6,101,417 A 8/2000 Vogel et al.
6,128,522 A 10/2000 Acker et al.
6,129,670 A 10/2000 Burdette et al.
6,137,161 A 10/2000 Gilliland et al.
6,141,594 A 10/2000 Flynn et al.
6,146,743 A 11/2000 Haq et al.
6,159,560 A 12/2000 Stevenson et al.
6,171,240 B1 1/2001 Young et al.
6,171,241 B1 1/2001 McVeigh et al.
6,188,219 B1 2/2001 Reeder et al.
6,198,972 B1 3/2001 Hartlaub et al.
6,209,764 B1 4/2001 Hartlaub et al.
6,226,545 B1 5/2001 Gilderdale
6,236,205 B1 5/2001 Ludeke et al.
6,238,390 B1 5/2001 Tu et al.
6,252,761 B1 6/2001 Branchevsky
6,263,229 B1 7/2001 Atalar et al.
6,272,370 B1 8/2001 Gillies et al.
6,275,369 B1 8/2001 Stevenson et al.
6,280,385 B1 8/2001 Melzer et al.
6,284,080 B1 9/2001 Haq et al.
6,284,971 B1 9/2001 Atalar et al.
6,332,089 B1 12/2001 Acker et al.
6,370,427 B1 4/2002 Alt et al.
6,373,673 B1 4/2002 Anthony
6,390,996 B1 5/2002 Halperin et al.
6,395,637 B1 5/2002 Park et al.
6,408,202 B1 6/2002 Lima et al.
6,414,835 B1 7/2002 Wolf et al.
6,424,234 B1 7/2002 Stevenson
6,428,537 B1 8/2002 Swanson et al.
6,433,653 B1 8/2002 Matsumura et al.
6,456,481 B1 9/2002 Stevenson
6,459,935 B1 10/2002 Piersma
6,470,545 B1 10/2002 Branchevsky
6,473,291 B1 10/2002 Stevenson
6,473,314 B1 10/2002 Custer et al.
6,486,529 B2 11/2002 Chi et al.
6,493,591 B1 12/2002 Stokes
6,512,666 B1 1/2003 Duva
6,529,103 B1 3/2003 Brendel et al.
6,535,766 B1 3/2003 Thompson et al.
6,539,253 B2 3/2003 Thompson et al.
6,539,261 B2 3/2003 Molin
6,549,800 B1 4/2003 Atalar et al.
6,556,009 B2 4/2003 Kellman et al.
6,566,978 B2 5/2003 Stevenson et al.
6,567,259 B2 5/2003 Stevenson et al.
6,567,703 B1 5/2003 Thompson et al.
6,593,884 B1 7/2003 Gilboa et al.
6,606,513 B2 8/2003 Lardo et al.
6,615,483 B2 9/2003 Lindegren
6,628,980 B2 9/2003 Atalar et al.
6,633,780 B1 10/2003 Berger et al.
6,643,903 B2 11/2003 Stevenson et al.
6,654,628 B1 11/2003 Silber et al.
6,660,116 B2 12/2003 Wolf
6,675,033 B1 1/2004 Lardo et al.
6,675,036 B2 1/2004 Kreger et al.
6,675,779 B2 1/2004 King et al.
6,675,780 B1 1/2004 Wendels et al.
6,687,550 B1 2/2004 Doan
6,690,963 B2 2/2004 Ben-Haim et al.
6,694,583 B2 2/2004 Branchevsky
6,697,675 B1 2/2004 Safarevich et al.
6,701,176 B1 3/2004 Halperin et al.
6,714,809 B2 3/2004 Lee et al.
6,728,575 B2 4/2004 Hedberg
6,728,579 B1 4/2004 Lindgren et al.
6,759,388 B1 7/2004 Marchant et al.
6,765,779 B2 7/2004 Stevenson et al.
6,765,780 B2 7/2004 Brendel et al.
6,768,630 B2 7/2004 Togashi
6,771,067 B2 8/2004 Kellman et al.
6,795,730 B2 9/2004 Connelly et al.
6,806,806 B2 10/2004 Anthony
6,823,215 B2 11/2004 Obel et al.
6,829,509 B1 12/2004 MacDonald et al.
6,847,837 B1 1/2005 Melzer et al.
6,868,288 B2 3/2005 Thompson
6,871,091 B2 3/2005 Wilkinson et al.
6,876,885 B2 4/2005 Swoyer et al.
6,882,248 B2 4/2005 Stevenson et al.
6,888,715 B2 5/2005 Stevenson et al.
6,898,454 B2 5/2005 Atalar et al.
6,901,292 B2 5/2005 Hrdlicka et al.
6,904,307 B2 6/2005 Karmarkar et al.
6,925,328 B2 8/2005 Foster et al.
6,930,242 B1 8/2005 Helfer et al.
6,931,283 B1 8/2005 Magnusson
6,931,286 B2 8/2005 Sigg et al.
6,934,588 B1 8/2005 Brand et al.
6,944,489 B2 9/2005 Zeijlemaker et al.
6,944,507 B2 9/2005 Froberg et al.
6,949,929 B2 9/2005 Gray et al.
6,950,696 B2 9/2005 Bjorling et al.
6,952,613 B2 10/2005 Swoyer et al.
6,971,391 B1 12/2005 Wang et al.
6,985,347 B2 1/2006 Stevenson et al.
6,985,775 B2 1/2006 Reinke et al.
6,999,818 B2 2/2006 Stevenson et al.

(56) References Cited

U.S. PATENT DOCUMENTS

| | | | |
|---|---|---|---|
| 7,012,192 | B2 | 3/2006 | Stevenson et al. |
| 7,013,180 | B2 | 3/2006 | Villaseca et al. |
| 7,015,393 | B2 | 3/2006 | Weiner et al. |
| 7,038,900 | B2 | 5/2006 | Stevenson et al. |
| 7,039,455 | B1 | 5/2006 | Brosovich et al. |
| 7,046,499 | B1 | 5/2006 | Imani et al. |
| 7,047,073 | B2 | 5/2006 | Hoijer et al. |
| 7,050,855 | B2 | 5/2006 | Zeijlemaker et al. |
| 7,068,491 | B1 | 6/2006 | Burdon et al. |
| 7,091,412 | B2 | 8/2006 | Wang et al. |
| 7,092,766 | B1 | 8/2006 | Salys et al. |
| 7,110,227 | B2 | 9/2006 | Anthony et al. |
| 7,113,387 | B2 | 9/2006 | Stevenson et al. |
| 7,123,013 | B2 | 10/2006 | Gray |
| 7,127,294 | B1 | 10/2006 | Wang et al. |
| 7,148,783 | B2 | 12/2006 | Parsche et al. |
| 7,149,578 | B2 | 12/2006 | Edvardsson |
| 7,149,773 | B2 | 12/2006 | Haller et al. |
| 7,155,271 | B2 | 12/2006 | Halperin |
| 7,162,302 | B2 | 1/2007 | Wang et al. |
| 7,164,572 | B1 | 1/2007 | Burdon et al. |
| 7,164,950 | B2 | 1/2007 | Kroll et al. |
| 7,174,219 | B2 | 2/2007 | Wahlstrand et al. |
| 7,199,995 | B2 | 4/2007 | Stevenson |
| 7,236,816 | B2 | 6/2007 | Kumar et al. |
| 7,236,834 | B2 | 6/2007 | Christopherson et al. |
| 7,276,474 | B2 | 10/2007 | Marchant et al. |
| 7,301,748 | B2 | 11/2007 | Anthony et al. |
| 7,310,216 | B2 | 12/2007 | Stevenson et al. |
| 7,319,905 | B1 | 1/2008 | Morgan et al. |
| 7,322,832 | B2 | 1/2008 | Kronich et al. |
| 7,327,553 | B2 | 2/2008 | Brendel |
| 7,363,090 | B2 | 4/2008 | Halperin |
| 7,369,898 | B1 | 5/2008 | Kroll et al. |
| 7,387,928 | B2 | 6/2008 | Cheung |
| 7,388,378 | B2 | 6/2008 | Gray et al. |
| 7,422,568 | B2 | 9/2008 | Yang et al. |
| 7,423,860 | B2 | 9/2008 | Anthony et al. |
| 7,428,136 | B2 | 9/2008 | Barnett |
| 7,433,168 | B2 | 10/2008 | Anthony |
| 7,436,672 | B2 | 10/2008 | Ushijima et al. |
| 7,439,449 | B1 | 10/2008 | Kumar et al. |
| 7,446,996 | B2 | 11/2008 | Togashi |
| 7,450,396 | B2 | 11/2008 | Ye et al. |
| 7,480,988 | B2 | 1/2009 | Ok et al. |
| 7,495,884 | B2 | 2/2009 | Togashi |
| 7,517,769 | B2 | 4/2009 | Van Schuylenbergh et al. |
| 7,529,590 | B2 | 5/2009 | MacDonald |
| 7,561,906 | B2 | 7/2009 | Atalar et al. |
| 7,586,728 | B2 | 9/2009 | Anthony |
| 7,593,208 | B2 | 9/2009 | Anthony et al. |
| 7,675,729 | B2 | 3/2010 | Anthony et al. |
| 7,679,926 | B2 | 3/2010 | Hsu et al. |
| 7,689,288 | B2 | 3/2010 | Stevenson et al. |
| 7,693,576 | B1 | 4/2010 | Lavie et al. |
| 7,702,387 | B2 | 4/2010 | Stevenson et al. |
| 7,719,854 | B2 | 5/2010 | Youker et al. |
| 7,729,770 | B2 | 6/2010 | Cabelka et al. |
| 7,733,621 | B2 | 6/2010 | Anthony et al. |
| 7,812,691 | B1 | 10/2010 | Fisk et al. |
| 7,839,146 | B2 | 11/2010 | Gray |
| 7,844,319 | B2 | 11/2010 | Susil et al. |
| 7,844,343 | B2 | 11/2010 | Wahlstrand et al. |
| 7,853,324 | B2 | 12/2010 | Stevenson et al. |
| 7,899,551 | B2 | 3/2011 | Westlund et al. |
| 7,901,761 | B1 | 3/2011 | Jiang et al. |
| 7,957,806 | B2 | 6/2011 | Stevenson et al. |
| 7,989,080 | B2 | 8/2011 | Greenberg et al. |
| 8,000,804 | B1 | 8/2011 | Wessendorf et al. |
| 8,043,454 | B1 | 10/2011 | Jiang et al. |
| 8,095,224 | B2 | 1/2012 | Truex et al. |
| 8,163,397 | B2 | 4/2012 | Ok et al. |
| 8,219,208 | B2 | 7/2012 | Stevenson et al. |
| 8,301,249 | B2 | 10/2012 | Min et al. |
| 8,659,870 | B2 | 2/2014 | Brendel et al. |
| 8,763,245 | B1 | 7/2014 | Lucisano et al. |
| 8,874,206 | B2 | 10/2014 | Malinowski et al. |
| 9,108,066 | B2 | 8/2015 | Woods et al. |
| 2002/0027282 | A1 | 3/2002 | Kawakami et al. |
| 2002/0055678 | A1 | 5/2002 | Scott et al. |
| 2002/0095197 | A1 | 7/2002 | Lardo et al. |
| 2002/0139556 | A1 | 10/2002 | Ok et al. |
| 2002/0177771 | A1 | 11/2002 | Guttman et al. |
| 2002/0192688 | A1 | 12/2002 | Yang et al. |
| 2003/0013928 | A1 | 1/2003 | Saruwatari |
| 2003/0013948 | A1 | 1/2003 | Russell |
| 2003/0028094 | A1 | 2/2003 | Kumar et al. |
| 2003/0028095 | A1 | 2/2003 | Tulley et al. |
| 2003/0050557 | A1 | 3/2003 | Susil et al. |
| 2003/0053284 | A1 | 3/2003 | Stevenson et al. |
| 2003/0083570 | A1 | 5/2003 | Cho et al. |
| 2003/0083723 | A1 | 5/2003 | Wilkinson et al. |
| 2003/0083726 | A1 | 5/2003 | Zeijlemaker et al. |
| 2003/0140931 | A1 | 7/2003 | Zeijlemaker et al. |
| 2003/0144704 | A1 | 7/2003 | Terry et al. |
| 2003/0144705 | A1 | 7/2003 | Funke |
| 2003/0144706 | A1 | 7/2003 | Funke |
| 2003/0144716 | A1 | 7/2003 | Reinke et al. |
| 2003/0144718 | A1 | 7/2003 | Zeijlemaker et al. |
| 2003/0144719 | A1 | 7/2003 | Zeijlemaker |
| 2003/0144720 | A1 | 7/2003 | Villaseca et al. |
| 2003/0144721 | A1 | 7/2003 | Villaseca et al. |
| 2003/0171792 | A1 | 9/2003 | Zarinetchi et al. |
| 2003/0179536 | A1* | 9/2003 | Stevenson et al. ..... 361/302 |
| 2003/0204217 | A1 | 10/2003 | Greatbatch |
| 2003/0208252 | A1 | 11/2003 | O'Boyle et al. |
| 2003/0212373 | A1 | 11/2003 | Hall et al. |
| 2003/0213605 | A1 | 11/2003 | Brendel et al. |
| 2004/0015079 | A1 | 1/2004 | Berger et al. |
| 2004/0034338 | A1 | 2/2004 | Thierfelder et al. |
| 2004/0088012 | A1 | 5/2004 | Kroll et al. |
| 2004/0167392 | A1 | 8/2004 | Halperin et al. |
| 2004/0210289 | A1 | 10/2004 | Wang et al. |
| 2004/0230271 | A1 | 11/2004 | Wang et al. |
| 2004/0249428 | A1 | 12/2004 | Wang et al. |
| 2004/0263173 | A1 | 12/2004 | Gray |
| 2004/0263174 | A1 | 12/2004 | Gray et al. |
| 2005/0007718 | A1 | 1/2005 | Stevenson et al. |
| 2005/0070972 | A1 | 3/2005 | Wahlstrand et al. |
| 2005/0113669 | A1 | 5/2005 | Helfer et al. |
| 2005/0113676 | A1 | 5/2005 | Weiner et al. |
| 2005/0113873 | A1 | 5/2005 | Weiner et al. |
| 2005/0113874 | A1 | 5/2005 | Connelly et al. |
| 2005/0113876 | A1 | 5/2005 | Weiner et al. |
| 2005/0190527 | A1 | 9/2005 | Stevenson et al. |
| 2005/0195556 | A1 | 9/2005 | Shah |
| 2005/0197677 | A1 | 9/2005 | Stevenson |
| 2005/0201039 | A1 | 9/2005 | Stevenson et al. |
| 2005/0215914 | A1 | 9/2005 | Bornzin et al. |
| 2005/0222642 | A1 | 10/2005 | Przybyszewski et al. |
| 2005/0222647 | A1 | 10/2005 | Wahlstrand et al. |
| 2005/0222656 | A1 | 10/2005 | Wahlstrand et al. |
| 2005/0222657 | A1 | 10/2005 | Wahlstrand et al. |
| 2005/0222658 | A1 | 10/2005 | Hoegh et al. |
| 2005/0222659 | A1 | 10/2005 | Olsen et al. |
| 2005/0247472 | A1 | 11/2005 | Helfer et al. |
| 2005/0248340 | A1 | 11/2005 | Berkcan et al. |
| 2005/0248907 | A1 | 11/2005 | Stevenson et al. |
| 2006/0009819 | A1 | 1/2006 | Przybyszewski |
| 2006/0025820 | A1 | 2/2006 | Phillips et al. |
| 2006/0030774 | A1 | 2/2006 | Gray et al. |
| 2006/0032665 | A1 | 2/2006 | Ice |
| 2006/0041294 | A1 | 2/2006 | Gray |
| 2006/0085043 | A1 | 4/2006 | Stevenson |
| 2006/0100506 | A1 | 5/2006 | Halperin et al. |
| 2006/0119361 | A1 | 6/2006 | Karmarkar et al. |
| 2006/0200218 | A1 | 9/2006 | Wahlstrand |
| 2006/0211979 | A1 | 9/2006 | Smith et al. |
| 2006/0212096 | A1 | 9/2006 | Stevenson |
| 2006/0221543 | A1 | 10/2006 | Stevenson et al. |
| 2006/0229693 | A1 | 10/2006 | Bauer et al. |
| 2006/0247684 | A1 | 11/2006 | Halperin |
| 2006/0247747 | A1 | 11/2006 | Olsen et al. |
| 2006/0247748 | A1 | 11/2006 | Wahlstrand et al. |

(56) References Cited

U.S. PATENT DOCUMENTS

| | | | |
|---|---|---|---|
| 2006/0252314 | A1 | 11/2006 | Atalar et al. |
| 2006/0259093 | A1 | 11/2006 | Stevenson et al. |
| 2006/0271138 | A1 | 11/2006 | MacDonald |
| 2007/0035910 | A1 | 2/2007 | Stevenson |
| 2007/0043399 | A1 | 2/2007 | Stevenson et al. |
| 2007/0060969 | A1 | 3/2007 | Burdon et al. |
| 2007/0060970 | A1 | 3/2007 | Burdon et al. |
| 2007/0083244 | A1 | 4/2007 | Stevenson et al. |
| 2007/0088416 | A1 | 4/2007 | Atalar et al. |
| 2007/0093142 | A1 | 4/2007 | MacDonald et al. |
| 2007/0106332 | A1 | 5/2007 | Denker et al. |
| 2007/0112398 | A1 | 5/2007 | Stevenson et al. |
| 2007/0123949 | A1 | 5/2007 | Dabney et al. |
| 2007/0167867 | A1 | 7/2007 | Wolf |
| 2007/0168005 | A1 | 7/2007 | Gray |
| 2007/0168006 | A1 | 7/2007 | Gray |
| 2007/0179554 | A1 | 8/2007 | Lyer et al. |
| 2007/0179577 | A1 | 8/2007 | Marshall et al. |
| 2007/0203529 | A1 | 8/2007 | Iyer et al. |
| 2007/0208383 | A1 | 9/2007 | Williams |
| 2007/0236861 | A1 | 10/2007 | Burdon et al. |
| 2007/0250143 | A1 | 10/2007 | Sommer et al. |
| 2007/0255332 | A1 | 11/2007 | Cabelka et al. |
| 2007/0255377 | A1 | 11/2007 | Marshall et al. |
| 2007/0288058 | A1 | 12/2007 | Halperin et al. |
| 2007/0299490 | A1 | 12/2007 | Yang et al. |
| 2008/0004670 | A1 | 1/2008 | McVenes et al. |
| 2008/0033497 | A1 | 2/2008 | Bulkes et al. |
| 2008/0039709 | A1 | 2/2008 | Karmarkar |
| 2008/0049376 | A1 | 2/2008 | Stevenson et al. |
| 2008/0049410 | A1 | 2/2008 | Kawaguchi et al. |
| 2008/0051854 | A1 | 2/2008 | Bulkes et al. |
| 2008/0071313 | A1 | 3/2008 | Stevenson et al. |
| 2008/0116997 | A1 | 5/2008 | Dabney |
| 2008/0132986 | A1 | 6/2008 | Gray et al. |
| 2008/0132987 | A1 | 6/2008 | Westlund |
| 2008/0140149 | A1 | 6/2008 | John et al. |
| 2008/0158746 | A1 | 7/2008 | Anthony et al. |
| 2008/0161886 | A1 | 7/2008 | Stevenson et al. |
| 2008/0195180 | A1 | 8/2008 | Stevenson et al. |
| 2008/0195186 | A1 | 8/2008 | Li et al. |
| 2008/0195187 | A1 | 8/2008 | Li et al. |
| 2008/0221638 | A1 | 9/2008 | Wedan et al. |
| 2008/0239622 | A1 | 10/2008 | Hsu et al. |
| 2008/0243218 | A1 | 10/2008 | Bottomley et al. |
| 2008/0247111 | A1 | 10/2008 | Anthony et al. |
| 2008/0247116 | A1 | 10/2008 | Kawano et al. |
| 2008/0247117 | A1 | 10/2008 | Elam et al. |
| 2008/0262584 | A1 | 10/2008 | Bottomley et al. |
| 2008/0262592 | A1 | 10/2008 | Jordan et al. |
| 2008/0264685 | A1 | 10/2008 | Park et al. |
| 2008/0269591 | A1 | 10/2008 | Halperin et al. |
| 2008/0277153 | A1 | 11/2008 | Teshome et al. |
| 2008/0314502 | A1 | 12/2008 | Ok et al. |
| 2009/0036944 | A1 | 2/2009 | Fonte |
| 2009/0097219 | A1 | 4/2009 | Cho et al. |
| 2009/0099440 | A1 | 4/2009 | Vohl |
| 2009/0099555 | A1 | 4/2009 | Vohl et al. |
| 2009/0107717 | A1 | 4/2009 | Hsu et al. |
| 2009/0116167 | A1 | 5/2009 | Stevenson et al. |
| 2009/0128976 | A1 | 5/2009 | Anthony |
| 2009/0139760 | A1 | 6/2009 | Tanaka |
| 2009/0163980 | A1 | 6/2009 | Stevenson |
| 2009/0180237 | A1 | 7/2009 | Hou et al. |
| 2009/0187229 | A1 | 7/2009 | Lavie |
| 2009/0236141 | A1 | 9/2009 | Kim et al. |
| 2009/0243756 | A1 | 10/2009 | Stevenson et al. |
| 2009/0259265 | A1 | 10/2009 | Stevenson et al. |
| 2009/0270948 | A1 | 10/2009 | Nghiem et al. |
| 2009/0281592 | A1 | 11/2009 | Vase |
| 2009/0312835 | A1 | 12/2009 | Stevenson |
| 2010/0010602 | A1 | 1/2010 | Wedan et al. |
| 2010/0016936 | A1 | 1/2010 | Stevenson et al. |
| 2010/0023000 | A1 | 1/2010 | Stevenson et al. |
| 2010/0023086 | A1 | 1/2010 | Lim |
| 2010/0023095 | A1 | 1/2010 | Stevenson et al. |
| 2010/0046135 | A1 | 2/2010 | Niki et al. |
| 2010/0046137 | A1 | 2/2010 | Adachi |
| 2010/0076538 | A1 | 3/2010 | Desai et al. |
| 2010/0109966 | A1 | 5/2010 | Mateychuk et al. |
| 2010/0114276 | A1 | 5/2010 | Min et al. |
| 2010/0114277 | A1 | 5/2010 | Zhao et al. |
| 2010/0138192 | A1 | 6/2010 | Min |
| 2010/0149042 | A1 | 6/2010 | Utsi et al. |
| 2010/0151113 | A1 | 6/2010 | Shelton |
| 2010/0160989 | A1 | 6/2010 | Legay |
| 2010/0160991 | A1 | 6/2010 | Lim |
| 2010/0174348 | A1 | 7/2010 | Bulkes et al. |
| 2010/0174349 | A1 | 7/2010 | Stevenson et al. |
| 2010/0198312 | A1 | 8/2010 | Stevenson et al. |
| 2010/0217262 | A1 | 8/2010 | Stevenson et al. |
| 2010/0217264 | A1 | 8/2010 | Odom et al. |
| 2010/0217341 | A1 | 8/2010 | John et al. |
| 2010/0234907 | A1 | 9/2010 | Dobak, III |
| 2011/0000699 | A1 | 1/2011 | Bealka et al. |
| 2011/0034965 | A1 | 2/2011 | Troetzschel et al. |
| 2011/0043297 | A1 | 2/2011 | Stevenson et al. |
| 2011/0048990 | A1 | 3/2011 | Goda |
| 2011/0106205 | A1 | 5/2011 | Reiterer et al. |
| 2011/0248184 | A1 | 10/2011 | Shah |
| 2012/0193117 | A1 | 8/2012 | Specht et al. |

FOREIGN PATENT DOCUMENTS

| | | |
|---|---|---|
| EP | 0466424 | 1/1992 |
| EP | 0557127 | 8/1993 |
| EP | 0673621 | 9/1995 |
| EP | 0697725 | 2/1996 |
| EP | 0498996 | 3/1997 |
| EP | 0930509 | 12/1998 |
| EP | 1021730 | 4/2003 |
| EP | 0930509 | 3/2004 |
| EP | 1469910 | 12/2006 |
| EP | 2025361 | 11/2007 |
| EP | 1883449 | 1/2009 |
| EP | 2025361 | 2/2009 |
| EP | 2392382 | 12/2011 |
| JP | 60141034 | 7/1985 |
| JP | 61181925 | 8/1986 |
| JP | 62233905 | 10/1987 |
| JP | 4071536 | 3/1992 |
| JP | 6054823 | 3/1994 |
| JP | 06070902 | 3/1994 |
| JP | 6176962 | 6/1994 |
| JP | 7272975 | 10/1995 |
| JP | 9094238 | 4/1997 |
| JP | 11239572 | 9/1999 |
| JP | 2004254257 | 9/2004 |
| JP | 2004289760 | 10/2004 |
| JP | 2005117606 | 4/2005 |
| JP | 2007129565 | 5/2007 |
| WO | 8704080 | 7/1987 |
| WO | 9210213 | 6/1992 |
| WO | 9423782 | 10/1994 |
| WO | 9740396 | 10/1997 |
| WO | 9852461 | 11/1998 |
| WO | 9919739 | 4/1999 |
| WO | 0010456 | 3/2000 |
| WO | 0025672 | 5/2000 |
| WO | 02083016 | 10/2002 |
| WO | 2003037424 | 5/2003 |
| WO | 2003063946 | 8/2003 |
| WO | 2003063952 | 8/2003 |
| WO | 2003063953 | 8/2003 |
| WO | 2003063955 | 8/2003 |
| WO | 2003063956 | 8/2003 |
| WO | 2003063957 | 8/2003 |
| WO | 2005081784 | 9/2005 |
| WO | 2005102445 | 11/2005 |
| WO | 2005102446 | 11/2005 |
| WO | 2005102447 | 11/2005 |
| WO | 2005115531 | 12/2005 |
| WO | 2006093685 | 9/2006 |
| WO | 2007047966 | 4/2007 |

(56) References Cited

FOREIGN PATENT DOCUMENTS

| | | |
|---|---|---|
| WO | 2007089988 | 8/2007 |
| WO | 2007102893 | 9/2007 |
| WO | 2007145671 | 12/2007 |
| WO | 2008077037 | 6/2008 |
| WO | 2008111986 | 9/2008 |
| WO | 2010008833 | 1/2010 |
| WO | 2013/158552 | 10/2013 |

OTHER PUBLICATIONS

Lu, et al., "Pt-Al2O3 interfacial bonding in implantable hermetic feedthroughs: Morphology and orientation", Society for Biomaterial—2011 Wiley Periodicals, Inc., Dec. 24, 2011, 817-824.
Luchinger, "Safety Aspects of Cardiac Pacemakers in Magnetic Resonance Imaging", A dissertation submitted to the Swiss Federal Institute of Technology Zurich, Switzerland, 2002.
European Search Report, Application No. 12157697.9 dated Jul. 5, 2012.
Shellock, et al., "Comparative Analyses of MR-Induced Distal Heating in Novel Filtered Cardiac Pacing Leads UsingTwo Geometric Configurations", 17th Scientific Meeting & Exhibition of the International Society for Magnetic Resonance in Medicine, Honolulu, Hawaii, Apr. 2009, 3014.
Shellock, "MRI Issues for Neuromodulation Devices", Institute for Magnetic Resonance Safety Education, and Research (IMRSER).
Susil, et al., "Multifunctional Interventional Devices for MRI: A Combined Electrophysiology/MRI Catheter", 2002, 594-600.
Susil, et al., U.S. Appl. No. 60/283,725, Multifunctional Interventional Devices for Use in MRI, Apr. 13, 2001.
Weiner, et al., U.S. Appl. No. 60/269,817, Electromagnetic Interference immune Cardiac Assist System, Feb. 20, 2001.
Wilk, et al., "High-K Gate Dielectrics: Current Status and Materials Properties Considerations", Journal of Applied Physi s, vol. 89, No. 10, May 15, 2001, 5243-5275.
European Search, application 13151536.3, dated Jun. 13, 2013.
European Search, application 13151537.1, dated Jun. 24, 2013.
European Search, application 13151537.1, dated Jul. 11, 2013.
European Search, application 13151535.5, dated Jul. 22, 2013.
Balanis, "Advanced Engineering Electromagnetics", 1989.
Clement, et al., "Estimation of Effective Lead Loop Area for Implantable Pulse Generators and Cardioverter/ Defibrillators for Determination of Susceptibility to Radiated Electromagnetic Interference", AAMI EMC Task Force, Apr. 12, 2004, 10 pages.
Ennis, et al., "Cautions About the Use of Equivalent Series Resistance (ESR) in Specifying Capacitors", Mar. 8, 1993, 58-64.
European Search, application 10167031.3 dated Sep. 19, 2012.
European Search, application 10167045.3, dated Oct. 10, 2012.
Gabriel, et al., "The Dielectric Properties of Biological Tissues: Parametric Models for the Dielectric Spectrum of Tissues", Parametric Models for the Dielectric Spectrum of Tissues, Phys. Med. Bio. 41, 1996, 2271-2293.
Ariel Roguin et al., Modem Pacemaker and Implantable Cardioverter/Defibrillator Systems Can Be Magnetic Resonance Imaging Safe, Circulation—Journal of the American Heart Association, Aug. 4, 2004 (originally published online Jul. 26, 2004), pp. 475-482, American Heart Association, Dallas, Texas, USA.
C. Gabriel, S. Gabriel and E. Cortout, I. Dielectric Properties of Biological Tissues: Literature Survey.
S. Gabriel, R.W. Lau and C. Gabriel, II. Dielectric Properties of Biological Tissues: Measurements and the Frequency Range 0Hz 10 20 GHz.
S. Gabriel, R.W. Lau and C. Gabriel, III. Dielectric Properties of Biological Tissues: Parametric Models for the Dielectric Spectrum of Tissues.
Constatine A. Balanis, Advanced Engineering Elecfromagnetics, John Wiley & Sons, Inc., 1989.
Robert C. Susil, Christopher J. Yeung, Henry R. Halperin, Albert CL. Lardo, Ergin Atalar, Multifunctional Interventional Devices for MRI: A Combined Electrophysiology/MRI Catheter, Magnetic Resonance in Medicine, 2002, pp. 594-600, Wiley-Liss, Inc., Departments of Biomedical Engineering, Radiology & Medicine, Johns Hopkins University School of Medicine, Baltimore, Maryland.
European Search Report dated Oct. 10, 2012.
European Search Report dated Sep. 19, 2012.
Maurts K. Konings, Lambertus W. Bartels, Henk F.M. Smts and Chris J.G. Bakker, "Heatng around Intravascular Guidewires by Resonating RF Waves," Journal of Magnetic Resonance Imaging, 12:79-85, 2000.
Michael J. Weiner, Wilson Greatbatch, Patrick R. Connelly, U.S. Appl. No. 60/269,817, filed Feb. 20, 2001, entitled "Electromagnetic Interference Immune Cardiac Assist System."
Wes Clement et al., "Estimation of Effective Lead Loop Area for Implantable Pulse Generators and Implantable Cardioverter Defibriallators," AAMI EMC Task Force, Apr. 12, 2004, 10 pages.
F.G. Shellock et al, Comparative Analysis of MR-Induced Distal Heating in Novel Filtered Cardiac Pacing Leads Using Two Geometric Configurations; 17th Scientific Meeting & Exhibition of the International Society for Magnetic Resonance in Medicine, Honolulu, Hawaii, Apr. 18-24, 2009, p. No. 3104.

* cited by examiner

FIG. 15
PRIOR ART
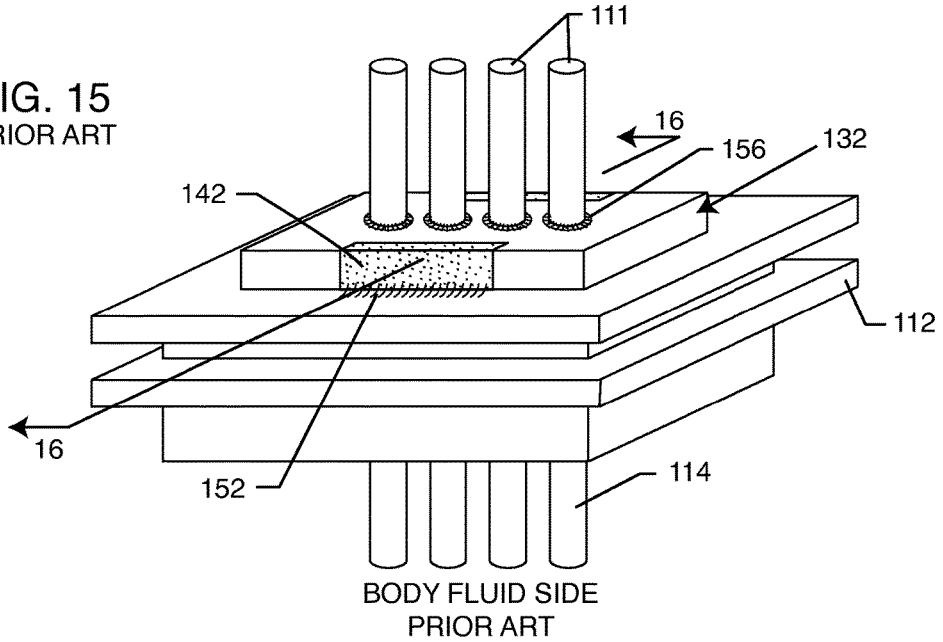
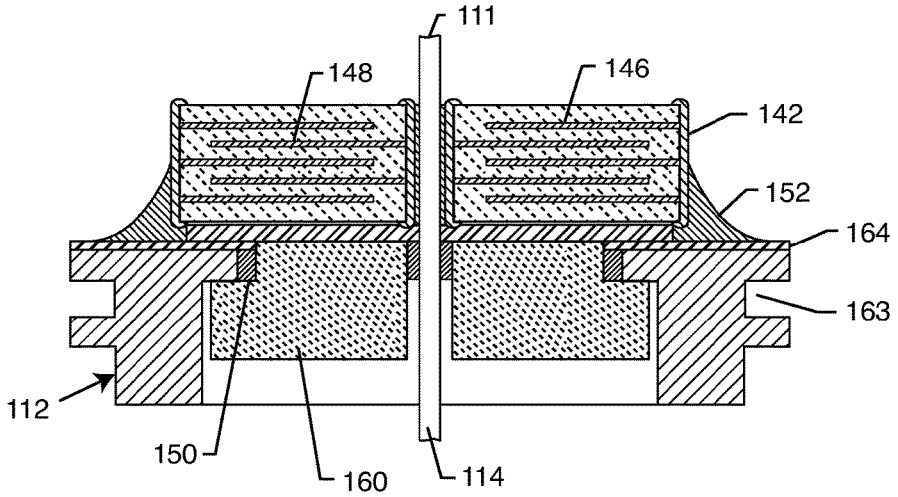
FIG. 16
PRIOR ART

LOW IMPEDANCE OXIDE RESISTANT GROUNDED CAPACITOR FOR AN AIMD

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application claims priority to U.S. provisional application Ser. No. 61/841,419, filed on Jun. 30, 2013. The present application also claims priority to and is a continuation-in-part application of U.S. application Ser. No. 13/873,832, filed on Apr. 30, 2013, the contents of which are incorporated herein by reference. The present application also claims priority to and is a continuation-in-part application of U.S. patent application Ser. No. 13/743,276, filed on Jan. 16, 2013, the contents of which are incorporated herein by reference.

FIELD OF THE INVENTION

The present invention generally relates to feedthrough capacitors. More particularly, the present invention relates to a feedthrough capacitor located on the device side with a low impedance and oxide-resistance electrical connection.

BACKGROUND OF THE INVENTION

Feedthrough capacitors and MLCC chip capacitors are well known in the prior art for active implantable medical devices (AIMDs). One is directed to U.S. Pat. Nos. 5,333,095; 5,905,627; 6,275,369; 6,529,103; and 6,765,780 all of which are incorporated herein by reference. The hermetic seal feedthrough terminal assemblies generally consist of a titanium ferrule into which an alumina hermetic seal is gold brazed. One or more lead wires penetrate through the alumina in non-conductive relationship with the ferrule. Gold brazes are also used to form a hermetic terminal between the one or more leadwires and the alumina ceramic.

First, some general information concerning good engineering design practice for electromagnetic interference (EMI) filters. It is very important to intercept the EMI at the point of lead conductor ingress and egress to the AIMD. It would be an inferior practice to put filtering elements down in the circuit board as this would draw EMI energy inside of the AIMD housing where it could re-radiate or cross-couple to sensitive AIMD circuits. A superior approach is to mount one or more feedthrough or MLCC-type capacitors right at the point of leadwire entrance so that it can be coupled to high frequency EMI signals from the lead conductors directly to the AIMD housing, which acts as an energy dissipating surface.

There are some interesting design challenges however. The titanium ferrule, which is laser welded into the overall AIMD housing, is at ground potential. Titanium tends to form oxides which act as either insulators or semi-conductors. Accordingly, grounding the feedthrough capacitor electrode plates directly to the titanium ferrule is contra-indicated. Reference is made to U.S. Pat. No. 6,465,779 (which is incorporated with this reference) which describes gold bond pad areas where the feedthrough capacitor external metallization can be directly connected to gold. The gold to which the feedthrough capacitor is directly connected is the braze material used to form the hermetic seal between the alumina and the titanium ferrule. As noted above, the hermetic seal is formed via a brazing process. By attaching the capacitor's ground plates to the gold, one can be assured that there will be no oxide that will increase the capacitor's equivalent series resistance (ESR) which can seriously degrade the capacitor's performance at high frequency. An undesirable aspect of using the gold braze for attachment is that gold is very expensive. Accordingly, there is a need for methods that provide a reliable low impedance ground path which are oxide resistant for grounding of AIMD filter capacitors. The present invention fulfills these needs and provides other related advantages.

SUMMARY OF THE INVENTION

An exemplary embodiment of a hermetically sealed filtered feedthrough assembly for an implantable medical device includes an insulator hermetically sealed to a conductive ferrule or housing. A conductor is hermetically sealed and disposed through the insulator in non-conductive relation to the conductive ferrule or housing between a body fluid side and a device side. A feedthrough capacitor is disposed on the device side. The feedthrough capacitor includes a first and a second end metallization, wherein the first end metallization is connected to at least one active electrode plate and wherein the second end metallization is connected to at least one ground electrode plate. The at least one active electrode plate is interleaved and disposed parallel to the at least one ground electrode plate, wherein the at least one active and at least one ground electrode plates are disposed within a capacitor dielectric. A first low impedance electrical connection is between the first end metallization and the conductor. A second low impedance electrical connection is between the second end metallization and the ferrule or housing. The second low impedance electrical connection includes an oxide-resistant metal addition attached directly to the ferrule or housing and an electrical connection coupling the second end metallization electrically and physically directly to the oxide-resistant metal addition.

In other exemplary embodiments the oxide-resistant metal addition may include a different material as compared to the ferrule or housing. The oxide-resistant metal addition may include a noble metal such as gold, platinum, palladium, silver and combinations thereof. The oxide-resistant metal addition may be laser welded to the ferrule or housing. The oxide-resistant metal addition may include a brazed metal such as gold. Possible braze materials include gold, gold-based metal, platinum, platinum based metal, palladium, palladium based metal, silver and silver based metal. Non-limiting noble metal based braze examples are gold-palladium, gold-boron, and palladium-silver. It is anticipated that proprietary brazes such as but not limited to the Pallabraze product family (palladium-containing) and Orobraze product family (gold-containing) offered by Johnson Matthey may be used. The braze material may be a rod, a ribbon, a powder, a paste, a cream, a wire and a preform such as but not limited to stamped washers.

A grounding loop may be defined on the device side having the first low impedance electrical connection and the second low impedance connection from the conductor through the feedthrough capacitor to the ferrule or housing. The total resistance of the grounding loop may be less than 1 milliohm. The total inductance of the grounding loop may be less than 10 nanohenries or less than 1 nanohenry.

The conductor may include a leadwire having platinum, palladium, silver or gold.

The insulator may be flush with the ferrule or housing on the device side. The insulator may include an alumina substrate comprised of at least 96% alumina and the conductor having a substantially closed pore and substantially pure platinum fill disposed within a via hole and extending between the body fluid side and the device side of the alumina substrate.

A hermetic seal may be between the platinum fill and the alumina substrate, wherein the platinum fill forms a tortuous and mutually conformal knitline or interface between the alumina substrate and the platinum fill, wherein the hermetic seal has a leak rate that is no greater than $1\times10^{-7}$ std cc He/sec.

An inherent shrink rate during a heat treatment of the alumina dielectric substrate in a green state may be greater than that of the platinum fill in the green state.

The oxide-resistant metal addition may include a wire, a pad, an L-shaped pad or an L-shaped pad with cutouts or combinations thereof.

A ground wire may be disposed through both the insulator and the feedthrough capacitor, where the ground wire is not electrically coupled to the at least one active and one ground electrode plate.

The ferrule or housing may include an integrally formed conductive peninsula, where the ground wire is electrically coupled to the peninsula.

The feedthrough capacitor may have a resonant frequency above 400 MHz. The feedthrough capacitor may have a capacitance of between 300 picofarads and 10,000 picofarads.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 15 is an assembly view taken from FIGS. 11-14 showing the quad polar rectangular feedthrough capacitor mounted onto the hermetic seal housing and the ferrule;

FIG. 16 is a sectional view taken from section 16-16 from FIG. 15;

DETAILED DESCRIPTION OF THE PREFERRED EMBODIMENTS

Figure 1:
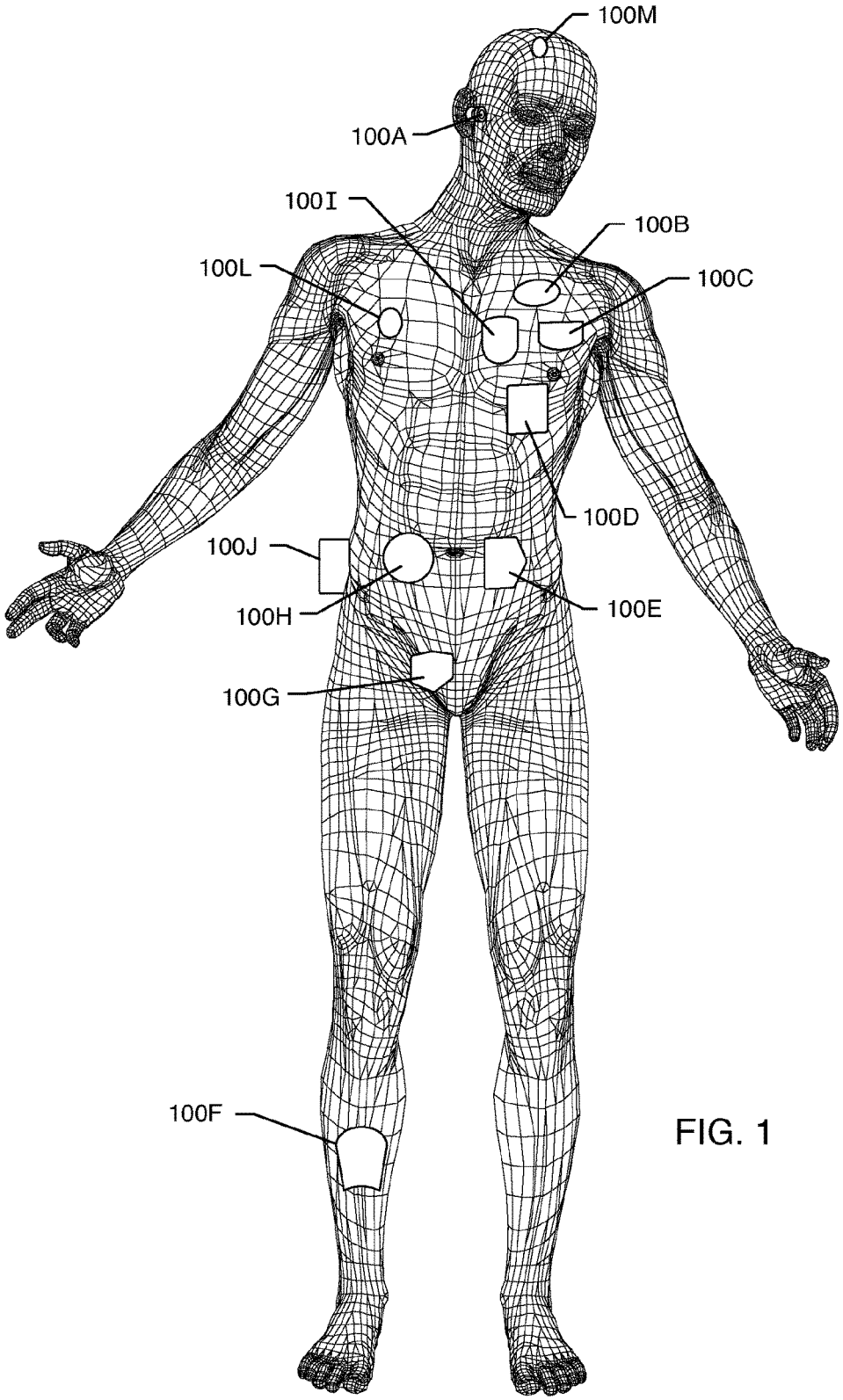
FIG. 1 illustrates a wire-formed diagram of a generic human body showing various types of active implantable and external medical devices currently in use.

FIG. 1 is a wire-formed diagram of a generic human body showing various types of active implantable and external medical devices 100 that are currently in use. 100A is a family of external and implantable hearing devices which can include the group of hearing aids, cochlear implants, piezoelectric sound bridge transducers and the like. 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for example but not limited to sensing the onset of the seizure and also providing electrical stimulation to brain tissue to prevent the seizure from actually happening, or for treating memory loss, Alzheimer's and the like. The lead wires that come from a deep brain stimulator are often placed using real time imaging. Most commonly such lead wires are placed during real time MRI. 100C shows a cardiac pacemaker which is well-known in the art. 100D includes the family of left ventricular assist devices (LVAD's), and artificial hearts, including the recently introduced artificial heart known as the ABIOCOR. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. 100F includes a variety of external or implantable bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillators (ICD) devices and also includes the family of congestive heart failure devices (CHF). This is also known in the art as cardio resynchronization therapy devices, otherwise known as CRT devices. 100J illustrates an externally worn pack. This pack could be an external insulin pump, an external drug pump, an external neurostimulator, a Holter monitor with skin electrodes or even a ventricular assist device power pack.

Figure 2:
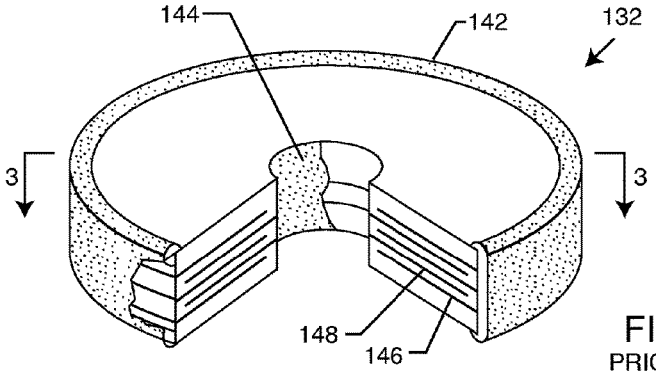
FIG. 2 PRIOR ART
FIG. 2 is an isometric cut-away view of a unipolar feedthrough capacitor.

FIG. 2 is an isometric cut-away view of a unipolar feedthrough capacitor 132. It has an outside diameter metallization 142 and an inside diameter metallization 144. Active electrode plates 148 and ground electrode plates 146 are interleaved in the dielectric body. The active electrode plate set 148 is connected to the inside diameter metallization 144. The ground electrode plate set 146 is connected to the outside diameter metallization 142. Metallization surfaces 142 and 144 can be glass fritted platinum silver or various types of plating. The metallization surfaces 142 and 144 are very important as it is easy to make electrical connection to these surfaces to other circuit elements.

Figure 3:
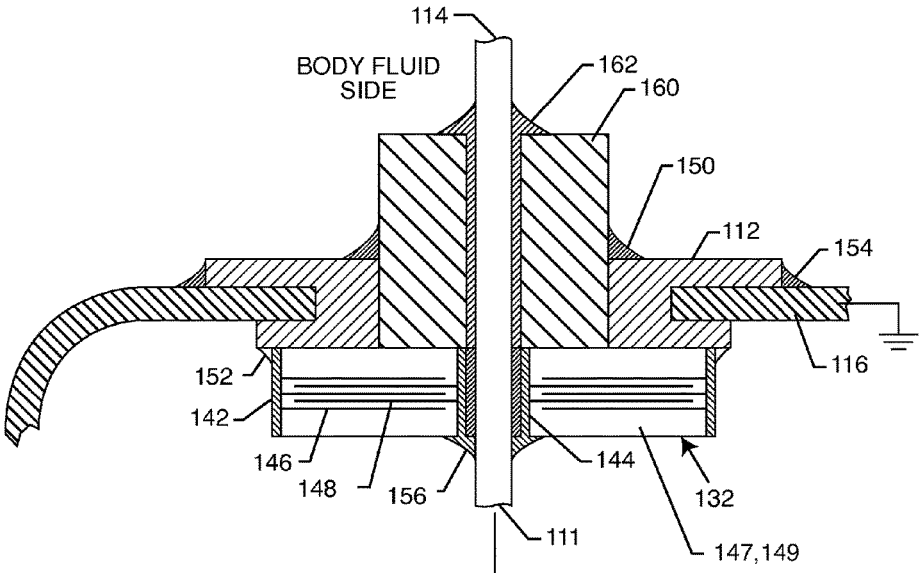
FIG. 3 PRIOR ART
FIG. 3 is a cross-sectional view of the unipolar capacitor of FIG. 2 shown connected to the hermetic terminal of an AIMD.

FIG. 3 is a cross-sectional view of the unipolar capacitor of FIG. 2 shown connected to the hermetic terminal of an active implantable medical device, such as a cardiac pacemaker. Shown is a hermetic seal formed from an insulator 160, such as an alumina ceramic, glass or the like. A gold braze 162 forms a hermetic seal between the insulator 160 and leadwire 114, 111. The leadwire labeled 114 on the body fluid side is generally directed to an implantable lead that has an electrode contactable to biological cells (not shown). And there is a second gold braze 150 which hermetically connects the outside diameter of the insulator material 160 to a ferrule 112. In the prior art, the ferrule is generally of titanium. The AIMD housing 116 is also generally of titanium. A laser weld 154 is formed which connects the ferrule 112 to the AIMD housing 116 electrically and mechanically. The laser weld 154 also forms a hermetic seal. The unipolar feedthrough capacitor 132 of FIG. 2 is shown mounted directly to the hermetic seal insulator. An electrical connection 156 connects the capacitor inside diameter metallization 144 to leadwire 111. There is also an electrical connection material 152 connected directly to the ferrule 112 as shown.

This electrical connection 152 is substantially inferior to the present invention and thus undesirable. As shown, an electrical connection is being made directly to the titanium surface 112. It is well known that titanium, particularly when brought to elevated temperatures, forms oxides. Oxides of titanium, for example, titanium dioxide is so stable, it's used as a paint pigment. It is also highly resistive and also has semi-conductive properties. For this reason, this inserts an undesirable series resistance $R_{OXIDE}$ between the feedthrough capacitor and the ferrule 112 and/or AIMD housing 116.

Figure 4:
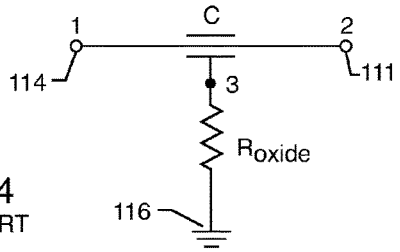
FIG. 4 PRIOR ART
FIG. 4 is a schematic diagram of the unipolar feedthrough capacitor shown in FIGS. 2 and 3.

FIG. 4 is a schematic diagram of unipolar feedthrough capacitor shown in FIGS. 2 and 3. Shown is an ideal feedthrough capacitor C. In general, feedthrough capacitors are three-terminal devices in that there is an input side 114 (terminal one), an output side 111 (terminal two) and a ground 116 (terminal three). It is well known that an implanted lead can undesirably act as an antenna and couple to high frequency electromagnetic interference (EMI) energy. This EMI energy may be undesirably coupled along the implanted leadwire conductors to lead 111, which is directed to sensitive AIMD electronics. It is well known that EMI can disrupt the proper operation of AIMD electronic circuitry. For example, there have been a number of case reports of complete inhibition of cardiac pacemakers when EMI was falsely detected as a normal cardiac rhythm and the pacemaker inhibited. This is immediately life-threatening as its leaves a pacemaker dependent patient without a heart beat during the entire time of the EMI exposure. The feature in the feedthrough capacitor as illustrated in FIGS. 2 and 3 is to divert incoming EMI energy in the implanted lead and dissipate it to the electromagnetically shielded housing 116 of the AIMD which said EMI energy may be dissipated as a harmless amount of thermal or RF energy. In other words, it is the job of feedthrough capacitors to protect the sensitive AIMD electronics while at the same time freely allowing pacing or therapeutic pulses to pass and also to allow the AIMD to sense biological signals that are generally in the frequency range from zero to 2000 Hz without interruption. The capacitor is also known as a frequency variable impedance element. The capacitive reactance $X_c$ in ohms:

$$X_c=1/[2\pi fc]$$

This inverse relationship with frequency means that, at very low frequencies, the capacitor looks like an open circuit (as if it were not there at all), and at very high frequencies, the capacitor acts as a short circuit where it diverts undesirable RF energy such as emissions from cellular telephones, microwave ovens or the like.

Referring once again to FIG. 4, one can see $R_{OXIDE}$. This resistive element is highly undesirable because it degrades the performance of the feedthrough capacitor all across its frequency range. There is also a great deal of variability in this oxide. During the gold brazing operation or during the formation of the hermetic seal, oxide poisoning may reach any corner or part of the brazing oven. The inventors have experienced some of the parts to be relatively oxide free where others in the lot may have a very thick or heavy oxide build-up.

Figure 5:
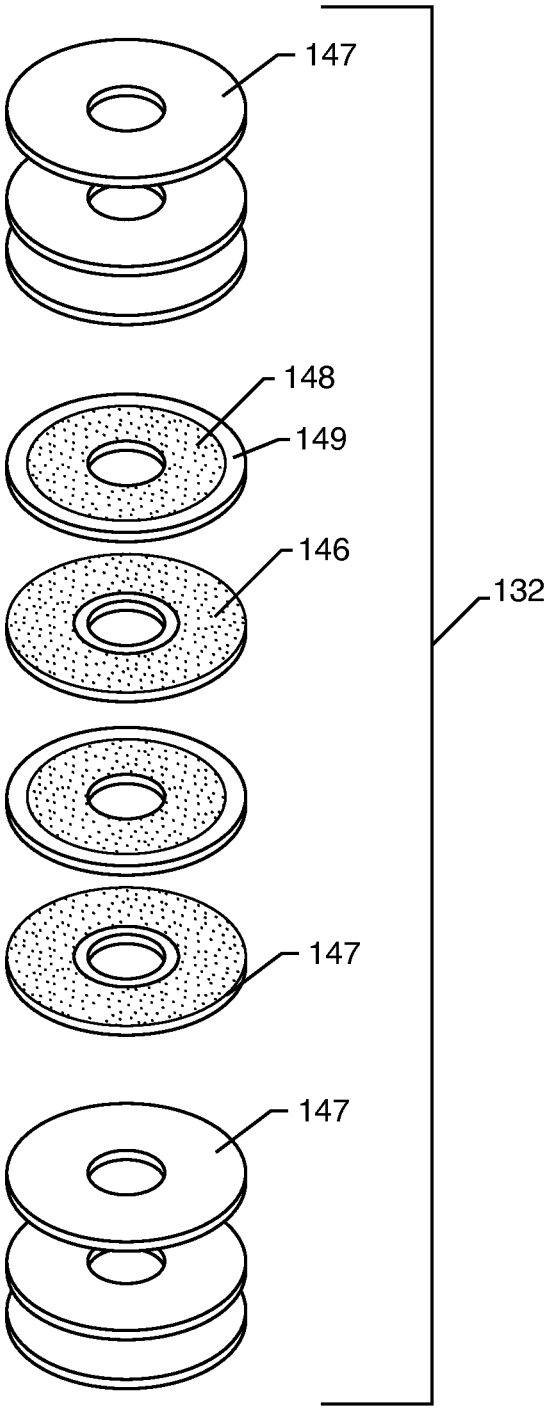
FIG. 5 PRIOR ART
FIG. 5 is an exploded view of the cover sheets and internal electrodes of the unipolar capacitor previously described in FIGS. 2 and 3.

FIG. 5 is an exploded view of the cover sheets 147 and internal electrodes of the unipolar capacitor 132 previously described in FIGS. 2 and 3. One can see that there are active electrode plates 148 screened onto dielectric layers 149 and interleaved with ground electrode plates 146. A number of blank cover sheets 147 are placed on top and bottom for insulative and mechanical strength purposes.

Figure 6:
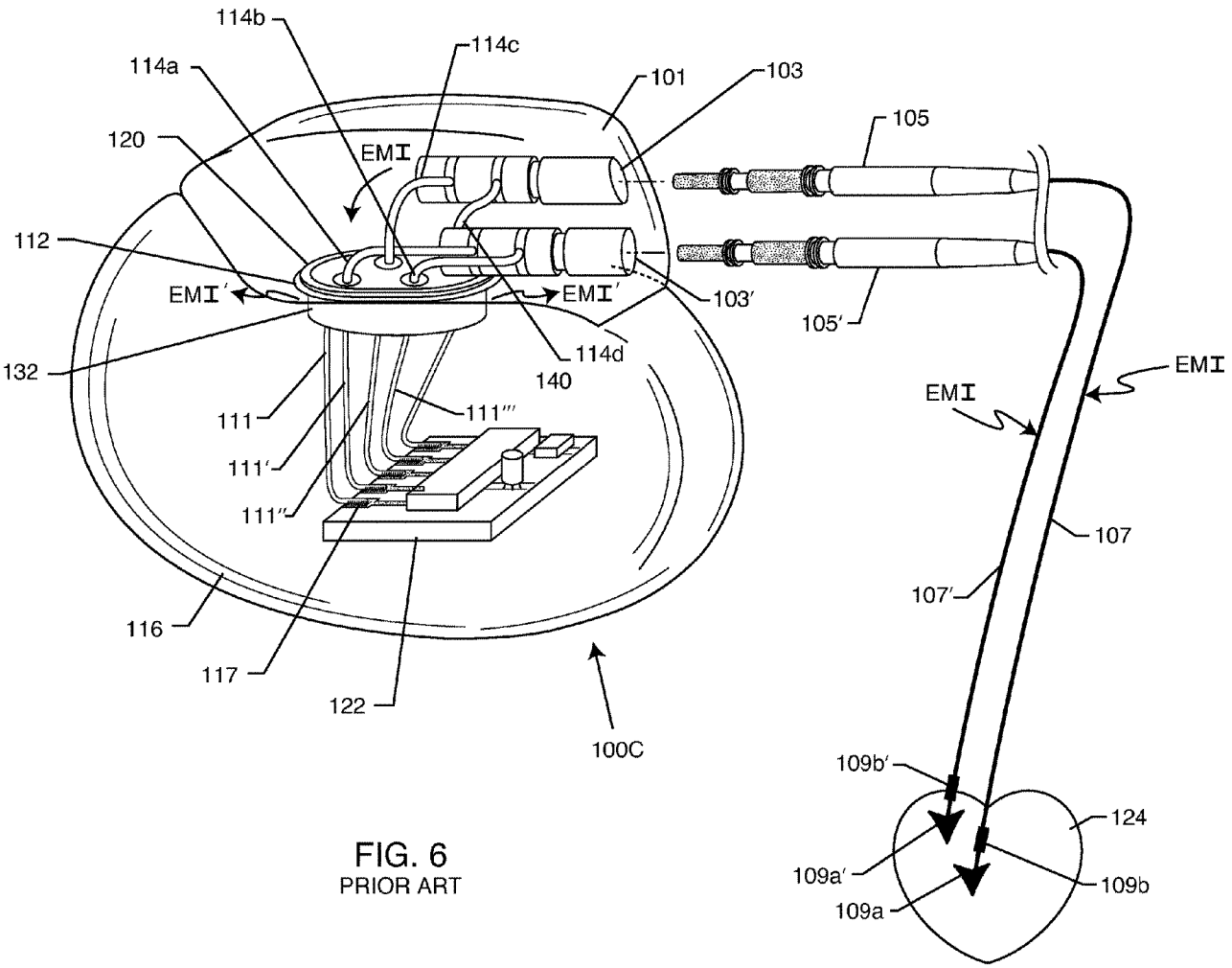
FIG. 6 PRIOR ART
FIG. 6 is a diagrammatic exploded view of a typical AIMD.

FIG. 6 is a diagrammatic explosion of a typical AIMD, such as a cardiac pacemaker 100C. It has an overall electromagnetic shielded titanium housing 116 along with a polymer header block (connector block) 101. Shown, are two implantable leads 107 and 107', which in this case are directed to chambers of the heart 124. There are additional electrodes located at point 109 in the right ventricle and distal electrodes 109' located in the right atrium. In the art, this is known as a simple dual chamber bipolar pacemaker. As shown, EMI can be undesirably coupled to leads 107 and 107' where it can be conductive to the leadwires 114 of the hermetic seal assembly 120. The feedthrough capacitor element 132 diverts the EMI conducted on leads 114 into the conductive AIMD housing 116 where it is dissipated as eddy currents or RF energy (EMI') as simply coupled to surrounding body tissues. In any event, the EMI is prevented from reaching the delicate AIMD circuit boards 122.

Figure 7:
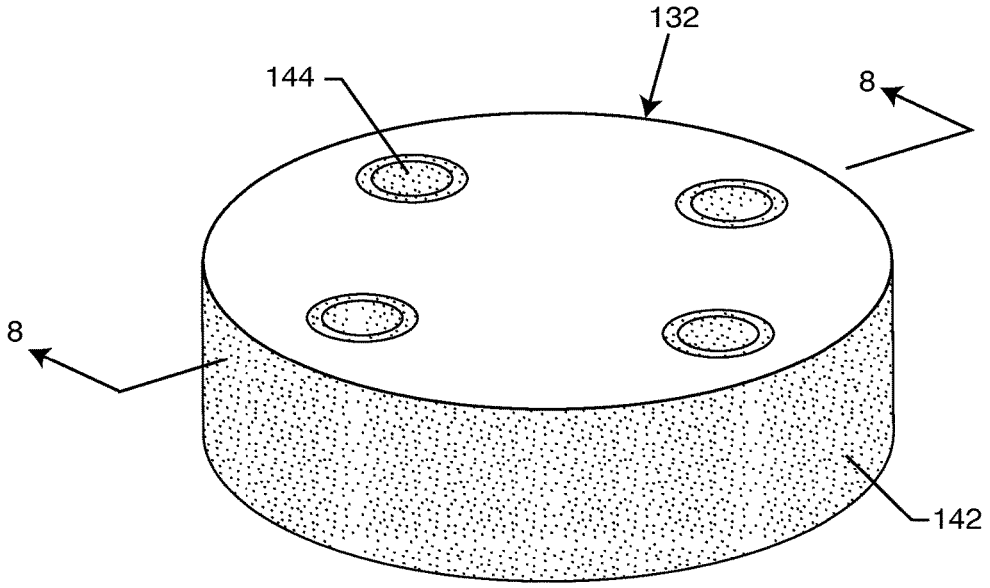
FIG. 7 PRIOR ART
FIG. 7 is an isometric view of the quad polar feedthrough capacitor previously described in the prior art pacemaker of FIG. 6.

FIG. 7 is an isometric view of the quad polar feedthrough capacitor 132 previously described in the prior art pacemaker of FIG. 6. The quad polar feedthrough capacitor has an outside diameter metallization 142 and four feedthrough holes all of which have inside diameter metallization 144.

Figure 8:
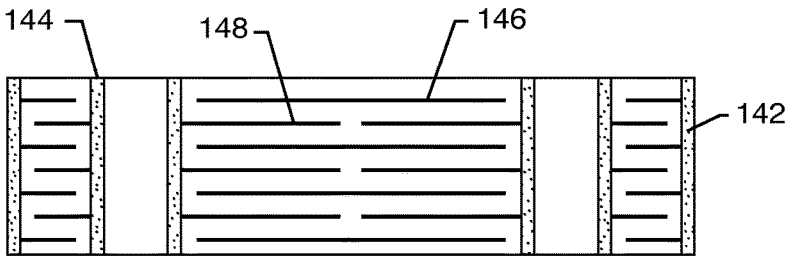
FIG. 8 PRIOR ART
FIG. 8 is a sectional view taken from section 8-8 of FIG. 7 and illustrates the quad polar feedthrough capacitor interior electrode plates.

FIG. 8 is a sectional view taken from section 8-8 of FIG. 7 and illustrates the quad polar feedthrough capacitor interior electrode plates. There is a ground electrode plate set 146 which is coupled to the outside diameter metallization 142. There are four different sets of active electrode plates 148 which are each coupled to their own individual feedthrough hole 134.

Figure 9:
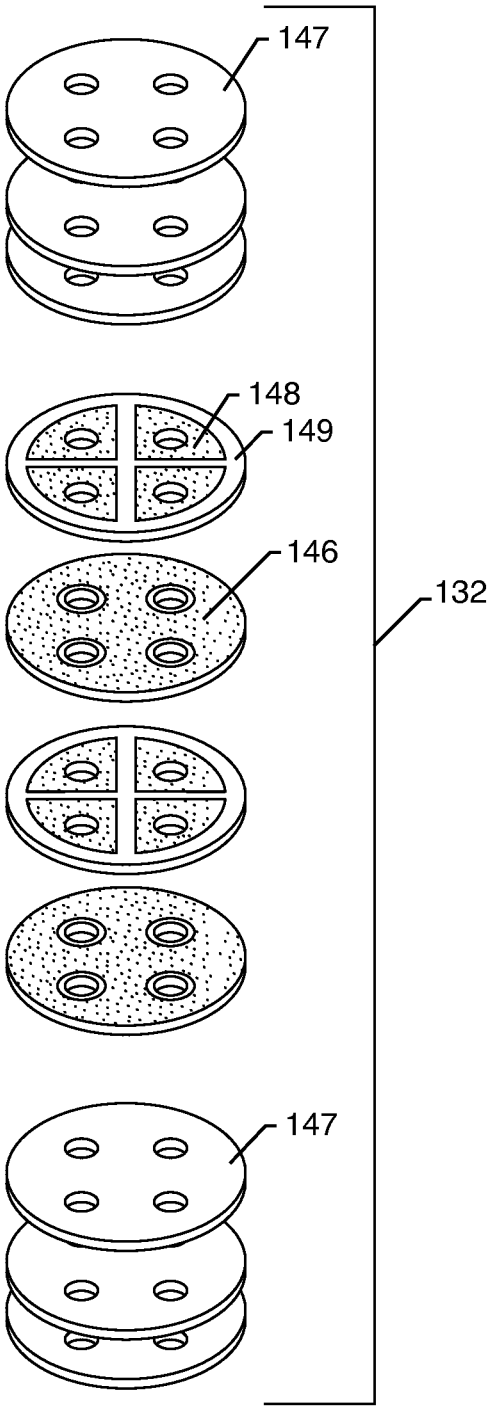
FIG. 9 PRIOR ART
FIG. 9 is an exploded view of the quad polar feedthrough capacitor of FIG. 7.

FIG. 9 is an exploded view of the quad polar feedthrough capacitor of FIG. 7. Shown, are the four active electrode plate areas 148 and the ground electrode plates 146. As previously described, these active and ground electrode plates are in interleaved relationship. There are also a number of blank ceramic cover sheets 147 added on top and bottom for mechanical strength and electrical insulation. Those skilled in the capacitor art will understand that a higher voltage capacitor could be built by interleaving additional blank electrodes between the active and ground electrode plates thereby building up the dielectric thickness. Typically, the dielectric material could be of barium titanate ceramic and could vary in dielectric constant k anywhere from 50 all the way up to several thousand.

Figure 10:
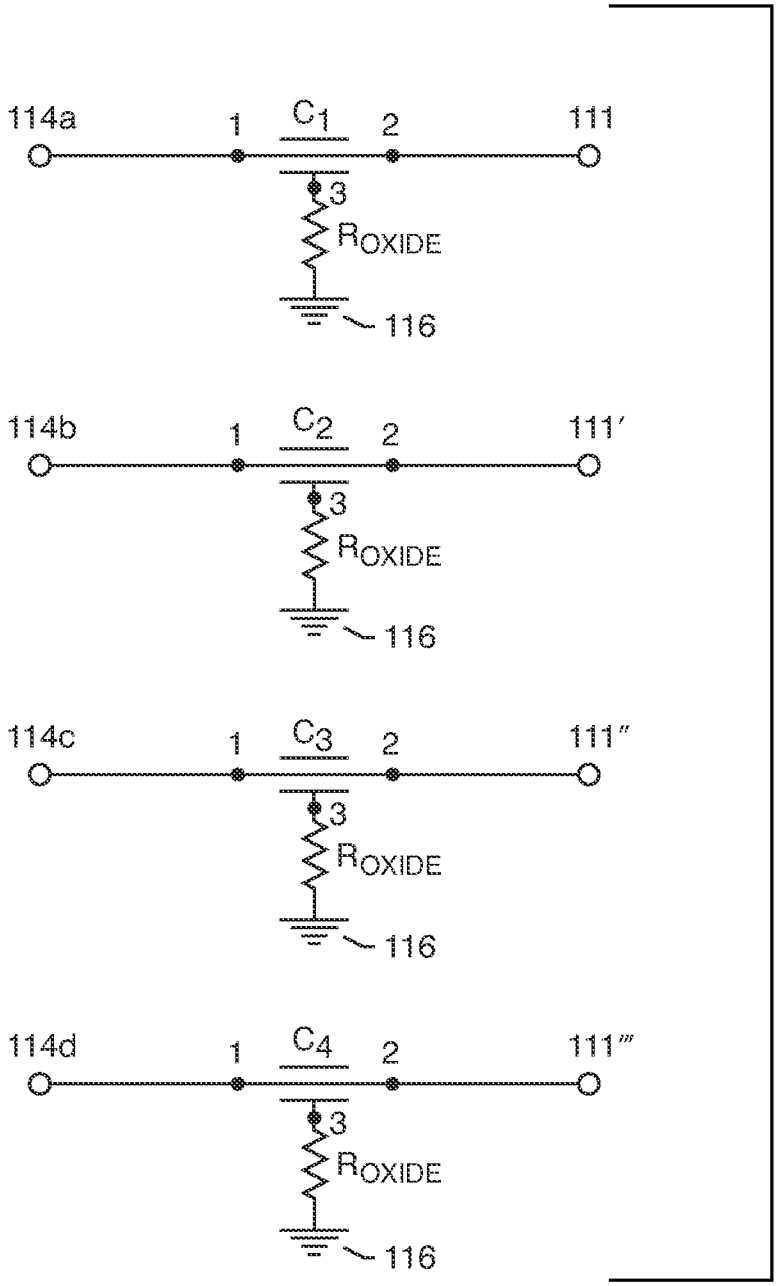
FIG. 10 PRIOR ART
FIG. 10 is the schematic diagram of the quad polar feedthrough capacitor of FIG. 7.

FIG. 10 is the schematic diagram of the quad polar feedthrough capacitor of FIG. 7. Again, as previously described for the unipolar capacitor of FIG. 2 and FIG. 4, there is an undesirable resistance $R_{OXIDE}$ as shown. Ideally, feedthrough capacitors are three-terminal devices that have no series inductance or series resistance. This is why they make such effective broadband electromagnetic interference filters. In general, a feedthrough capacitor can provide attenuation over a very broad frequency range extending even to 18 to 20 GHz. However, this oxide is highly undesirable as it can seriously degrade filter performance. In general, filter performance is described by the terms insertion loss or by attenuation. Both of these are generally measured in a balanced 50 ohm system with the measurement units in decibels.

Figure 11:
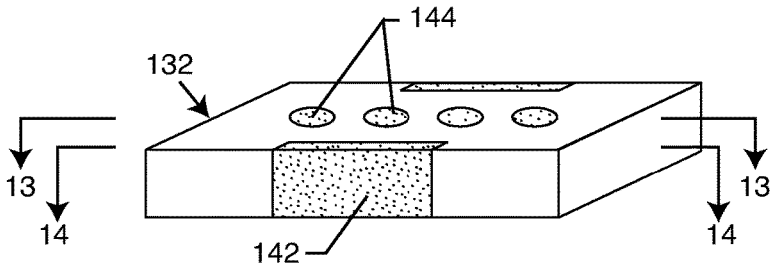
FIG. 11 PRIOR ART
FIG. 11 illustrates a prior art quad polar feedthrough capacitor that is rectangular instead of round.
Figure 12:
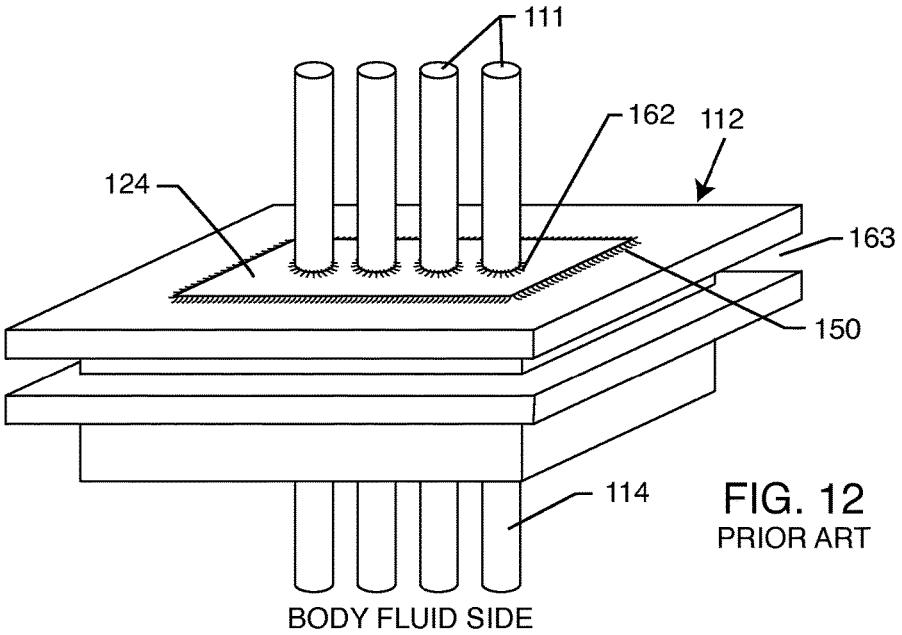
FIG. 12 PRIOR ART
FIG. 12 is an isometric view of the feedthrough assembly before the feedthrough capacitor is placed.

FIG. 11 illustrates a prior art quad polar feedthrough capacitor that, in this case, is rectangular instead of round. It still has an outside metallization 142, but in this embodiment, instead of being all around a perimeter or outside diameter, it is shown only over a portion of the rectangular edge of the capacitor. This can actually be done in many ways. One way would be to extend the metallization 142 around the entire perimeter of the capacitor. Feedthrough metallization 144 is provided for each of the four feedthrough holes. FIG. 11 in combination with FIG. 12 illustrates an exploded assembly view wherein the capacitor of FIG. 11 is designed to be mounted atop a prior art quad polar hermetic terminal of FIG. 12. The hermetic terminal of FIG. 12 has four leadwires 111, 114, a hermetic insulator 124 and a ferrule, generally of titanium 112. There is a gold braze 150 which forms a hermetic joint between the ferrule 112 and the generally alumina ceramic insulator 124. There are four more gold brazes 162 which join leadwire 111 to the inside diameter holes of the hermetic insulator 124.

Figure 13:
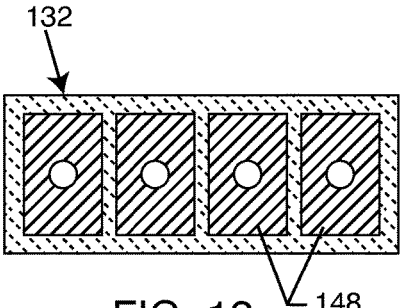
FIG. 13 PRIOR ART
FIG. 13 is taken from section 13-13 from FIG. 11 showing the four active electrode plates.

FIG. 13 is taken from section 13-13 from FIG. 11. Shown are the four active electrode plates 148 of the feedthrough capacitor.

Figure 14:
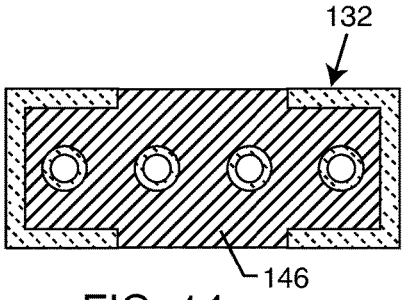
FIG. 14 PRIOR ART
FIG. 14 is taken from section 14-14 from FIG. 11 and illustrates the ground electrode plate.

FIG. 14 is taken from section 14-14 from FIG. 11 and illustrates the ground electrode plate 146 of the feedthrough capacitor.

FIG. 15 is an assembly view taken from FIGS. 11 and 12 showing the quad polar rectangular feedthrough capacitor mounted onto the hermetic seal housing and the ferrule 112. An electrical connection 152 is generally made with a thermal-setting conductive adhesive between the capacitor metallization 142 directly to the ferrule 112.

FIG. 16 is a sectional view taken from section 16-16 from FIG. 15. This sectional view goes through one of the leadwires 111 and shows the interior ground electrode plate set 146 and the active electrode plate set 148. The ground electrode plates 146 make electrical and mechanical contact to the capacitor ground metallization 142. There is an electrical connection 152 shown directly to the top surface of the titanium ferrule 112. There is a cross-hatched area 164 which shows the formation of a very undesirable layer of titanium oxides. For simplicity, this layer is shown only on the top surface, but in reality, it would coat all of the surfaces of the titanium cross-section. As previously mentioned, the formation of this oxide can happen during initial gold brazing, during subsequent storage and handling of the overall filter feedthrough subassembly, or during laser welding of the ferrule 112 into the AIMD housing 116. One particular problem is that the thermal-setting conductive adhesive 152 always contains a certain amount of available oxygen. When a laser weld is formed to the AIMD housing, which is positioned to be placed in slot 163, this significantly raises the temperature of thermal-setting conductive adhesive 152. This is why a thermal-setting conductive polyimide is the connection material of choice, as a conductive polyimide is stable at temperatures well above 300 degrees C. This is in comparison to most epoxies which are only rated to about 230 degrees C. When this assembly is raised through laser welding to high temperature, oxygen can be released from a thermal-setting conductive material 152 and then be formed as a titanium dioxide or trioxide 164 on the ferrule 112 of the hermetic seal.

Figure 17:
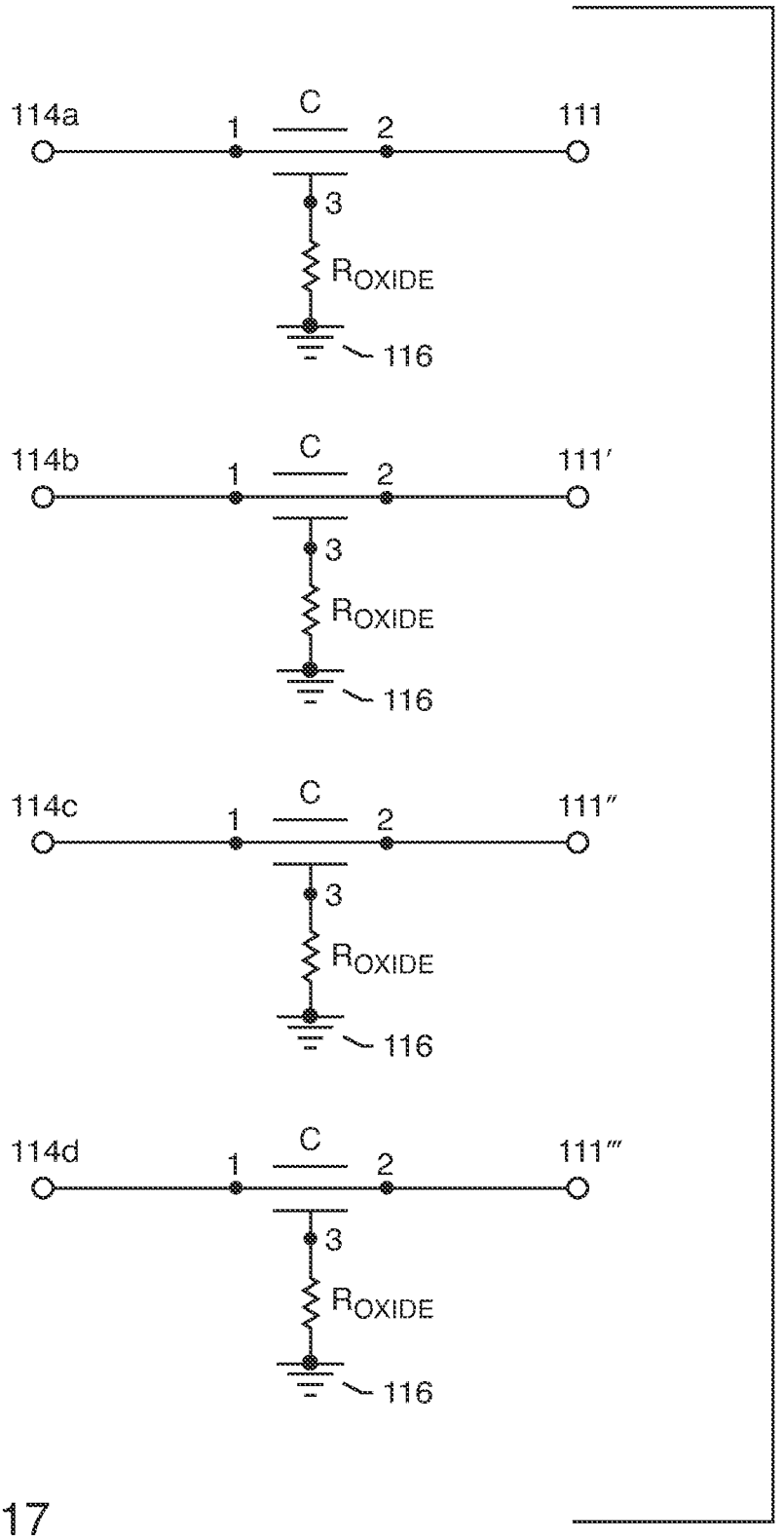
FIG. 17 PRIOR ART
FIG. 17 is the schematic diagram of the quad polar feedthrough capacitors previously illustrated in FIGS. 14 and 15.

FIG. 17 is the schematic diagram of the quad polar feedthrough capacitors previously illustrated in FIGS. 11, 15 and 16. Shown, is the undesirable $R_{OXIDE}$ which is shown in series between the ideal feedthrough capacitor and ground, which is the same electrical potential as the AIMD housing 116. As will be shown, the presence of this resistive oxide seriously degrades the filter performance.

Figure 18:
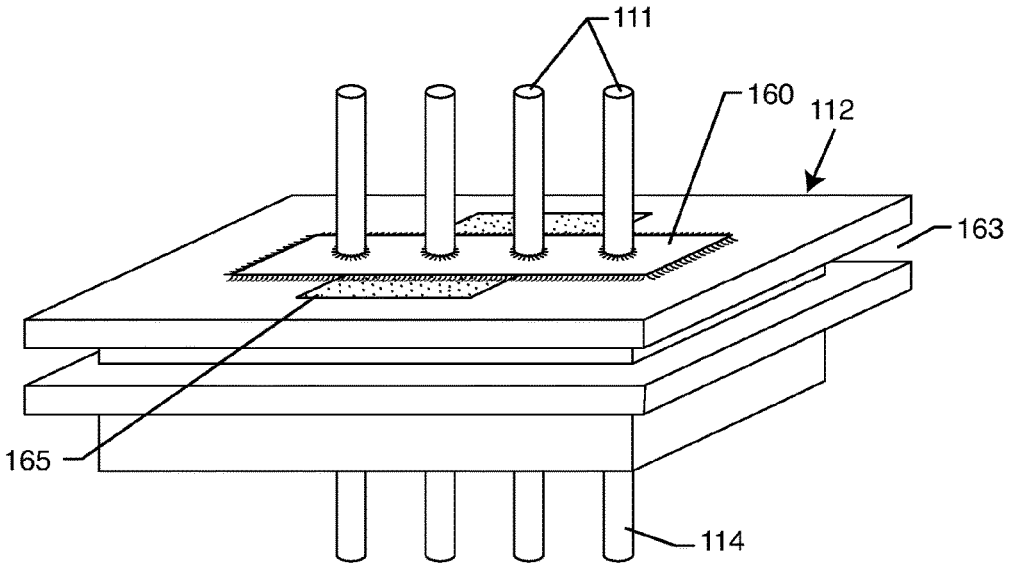
FIG. 18 PRIOR ART
FIG. 18 is a perspective view showing gold bond pads used to eliminate the problem of attachment to oxides of titanium between the feedthrough capacitor outside diameter and its ground electrode plate sets.
Figure 20:
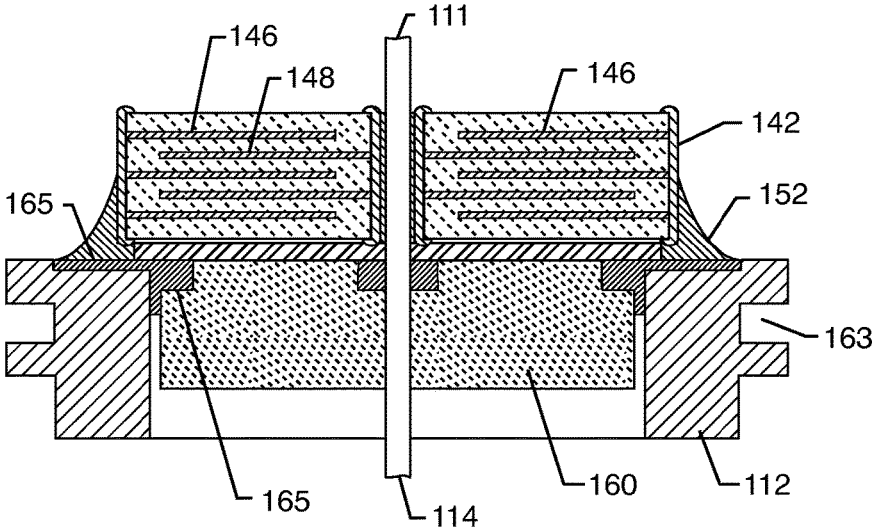
FIG. 20 PRIOR ART
FIG. 20 is a sectional view of the structure of FIG. 19 taken through lines 20-20.

FIG. 18 is taken from FIG. 20 of U.S. Pat. No. 6,765,779 which describes gold bond pads to eliminate the problem of attachment to oxides of titanium between the feedthrough capacitor outside diameter and its ground electrode plate sets. Referring to FIG. 18, one can see that there are novel gold braze pads 165 that have been added. Referring to FIG. 12, one can see that these gold braze pads 165 are not present.

Figure 19:
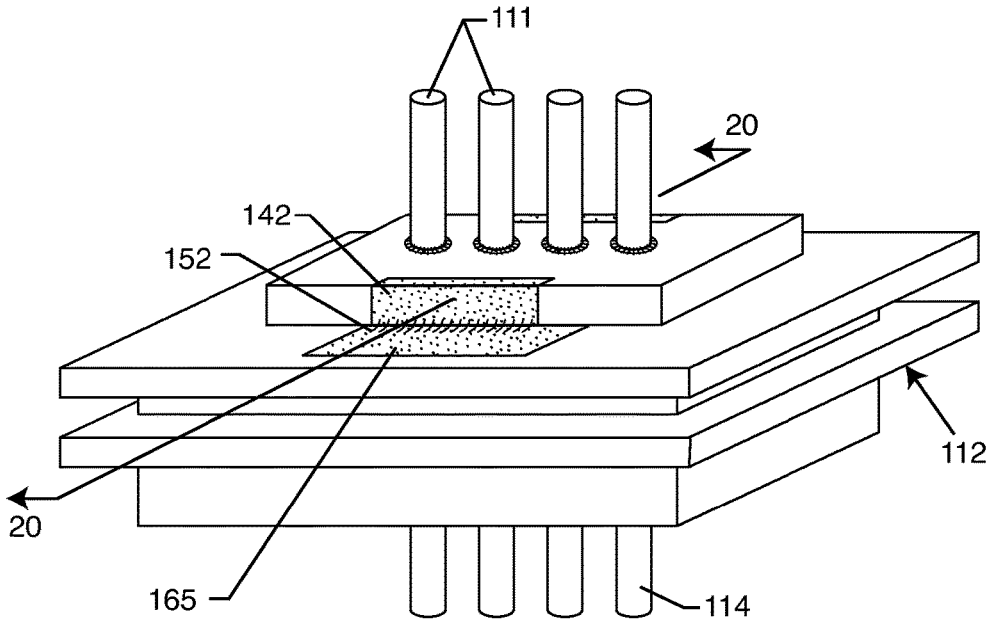
FIG. 19 PRIOR ART
FIG. 19 shows that the electrical connections between the capacitor's ground metallization is now directly connected to this oxide resistant noble pad.

FIG. 19 shows that the electrical connections 152 between the capacitor's ground metallization 142 is now directly made to this non-oxidizable noble pad. U.S. Pat. No. 6,765,779 is incorporated herein by reference. As is shown in this '779 patent, a preferred material for the oxide resistant pad 165 is gold. In a particularly preferred embodiment, this gold pad 165 is continuous and is co-formed at the same time the hermetic seal (gold braze) is made to the alumina ceramic insulator 160. In fact, this is a limitation of U.S. Pat. No. 6,765,779 in that the gold bond pad 165 is always formed as part of the co-braze to the alumina ceramic insulator 160.

FIG. 20 is generally taken from section 20-20 from FIG. 19. It is very similar to FIG. 16 except that the gold braze area 165 has been enlarged to include the gold bond pad area 165. Pure gold has a high melting point (1064° C.) which is above the allotropic transformation temperature of titanium (883° C.). Titanium is soluble in gold, particularly more so at elevated temperature. Elevated temperature maximizes titanium dissolution into gold. As previously noted, titanium is highly reactive to air readily forming surface oxides. Brazing to titanium, therefore, is generally performed at high vacuum. At high vacuum brazing temperatures, when a gold brazed joint [164] *165* is formed between, for example, a gold braze preform and a titanium ferrule, the titanium reacts with the gold to form a direct metallurgical bond to the titanium ferrule 112. As this direct metallurgical bond is gold-rich, it essentially retains the high conductivity of the gold and its oxide resistant properties. In this regard, the enlarged gold braze area surface, that is, the bonding pad that is formed is part of the oxide-resistant metallurgical bond. This enlarged gold braze area serves as the[,] electrical connection material that is connectable to the capacitor ground metallization 142. To summarize, a continuous electrical connection that is consistent in its conductivity over the service life of the device is made. The electrical connection is between the titanium ferrule 112 and the filter capacitor ground metallization 142 via the electrical connection material 152 directly to the non-oxidizable *gold bond* pad 165.

Figure 21:
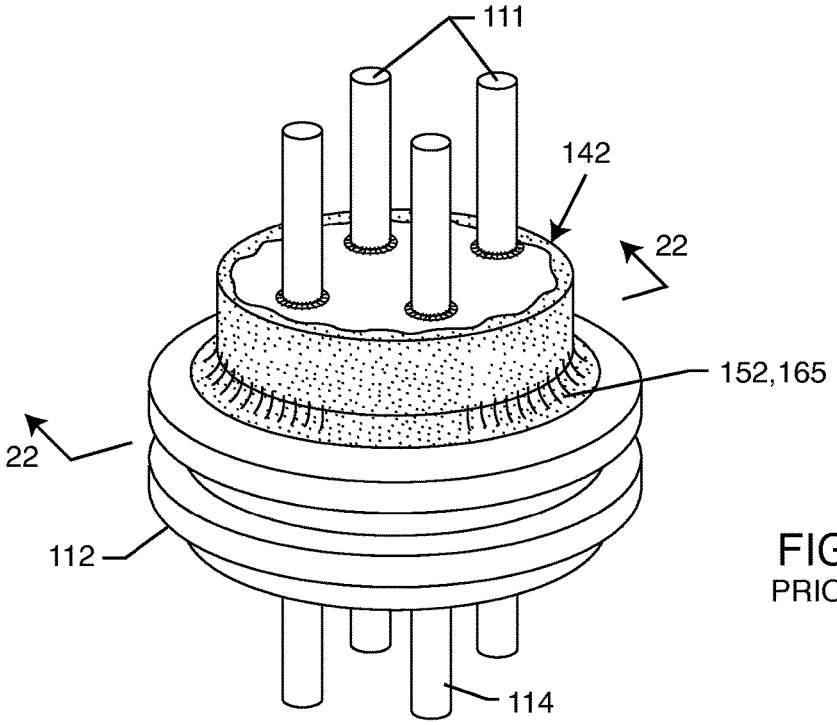
FIG. 21 PRIOR ART
FIG. 21 is very similar to FIG. 19, except that the quad polar capacitor is round which is consistent with the feedthrough capacitor previously illustrated in the cardiac pacemaker of FIG. 6.

FIG. 21 is very similar to FIG. 19, except in this case, the quad polar capacitor is round which is consistent with the feedthrough capacitor 132 previously illustrated in the cardiac pacemaker of FIG. 6.

Figure 22:
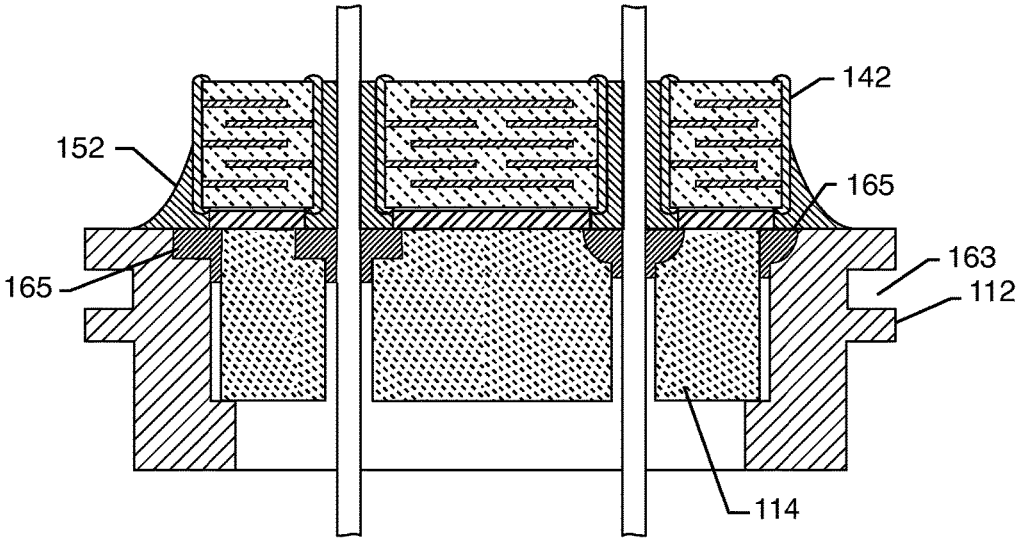
FIG. 22 PRIOR ART
FIG. 22 is generally taken from section 22-22 from FIG. 21 and illustrates the capacitor's internal structure including its ground and active electrode plates.

FIG. 22 is generally taken from section 22-22 from FIG. 21 and illustrates the capacitor's internal structure including its ground and active electrode plates. Importantly, outside diameter electrical connection material 152, which connects the outside diameter metallization 142 to the ferrule 112, is directly attached to the gold braze material 165. The fact that some of this overlaps onto the titanium surface is not important. What is critical is that a suitable amount of the electrical connection material 152 is directly attached to an oxide resistant noble surface, such that an undesirable resistance can never develop.

Figure 23:
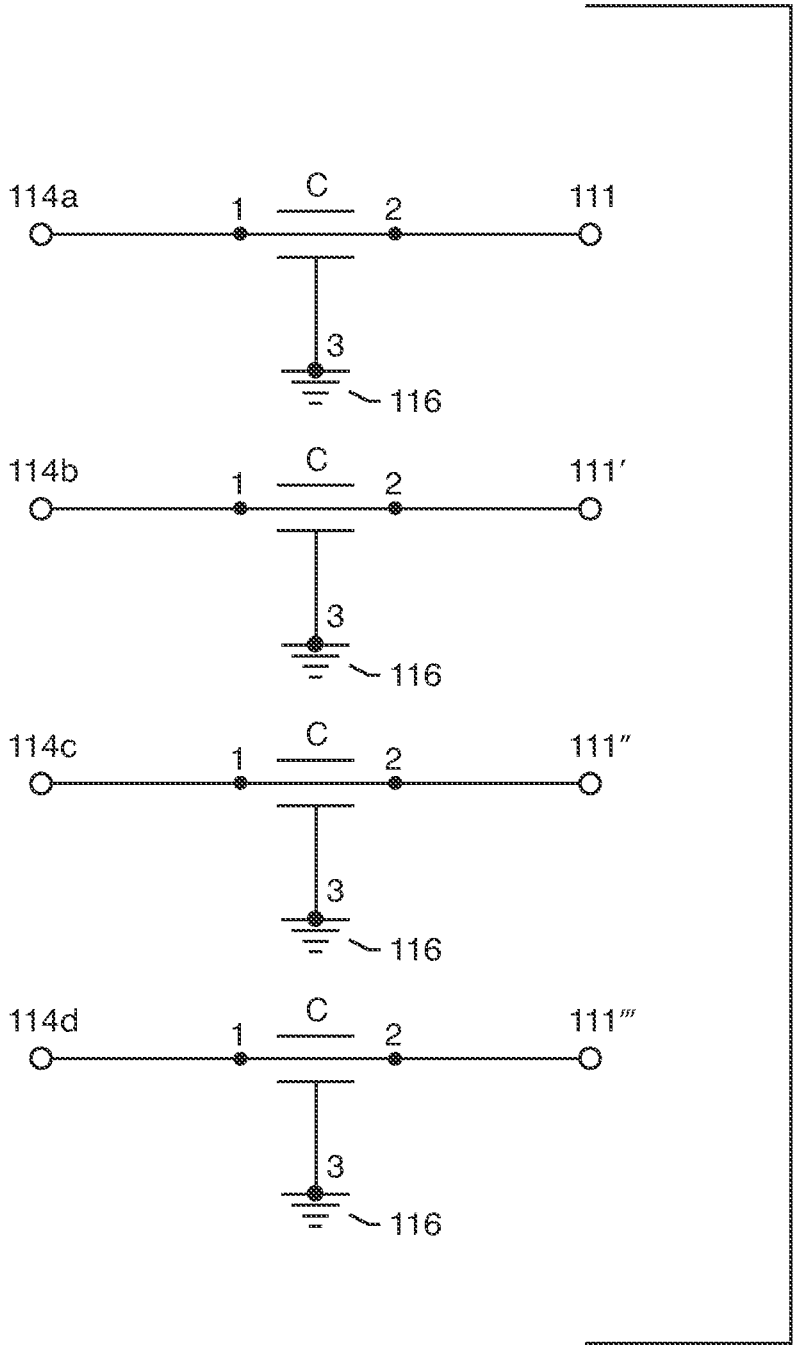
FIG. 23 PRIOR ART
FIG. 23 illustrates the schematic diagram of the improved rectangular quad polar feedthrough capacitor of FIG. 19 and the round quad polar capacitor of FIG. 21.

FIG. 23 illustrates the schematic diagram of the improved rectangular quad polar feedthrough capacitor of FIG. 19 and the round quad polar capacitor of FIG. 21. One can see that we now have insignificant resistance in the connection from the feedthrough capacitor to ground 116, which is the overall shielded equipotential surface of the electromagnetically shielded housing 116.

Figure 24:
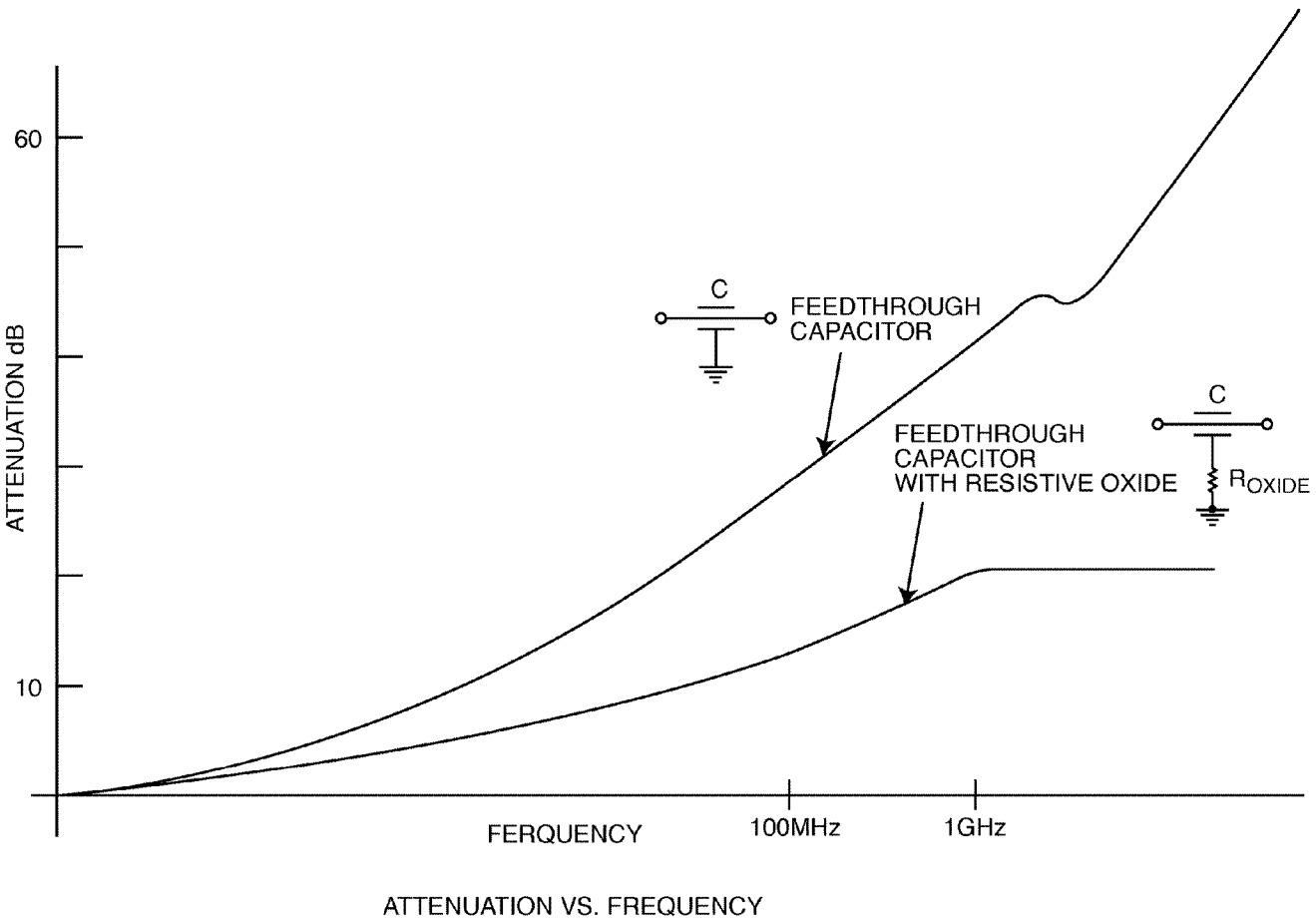
FIG. 24 PRIOR ART
FIG. 24 illustrates attenuation versus frequency comparing the ideal feedthrough capacitor to one that has undesirable ground electrode plate connection to an oxidized surface.

FIG. 24 is attenuation versus frequency curves which compares the ideal feedthrough capacitor to one that has undesirable ground electrode plate connection to an oxidized surface. One can see that the feedthrough capacitor with the resistive oxide $R_{OXIDE}$ has greatly reduced attenuation all across the frequency band as compared to the ideal feedthrough capacitor.

Figure 25:
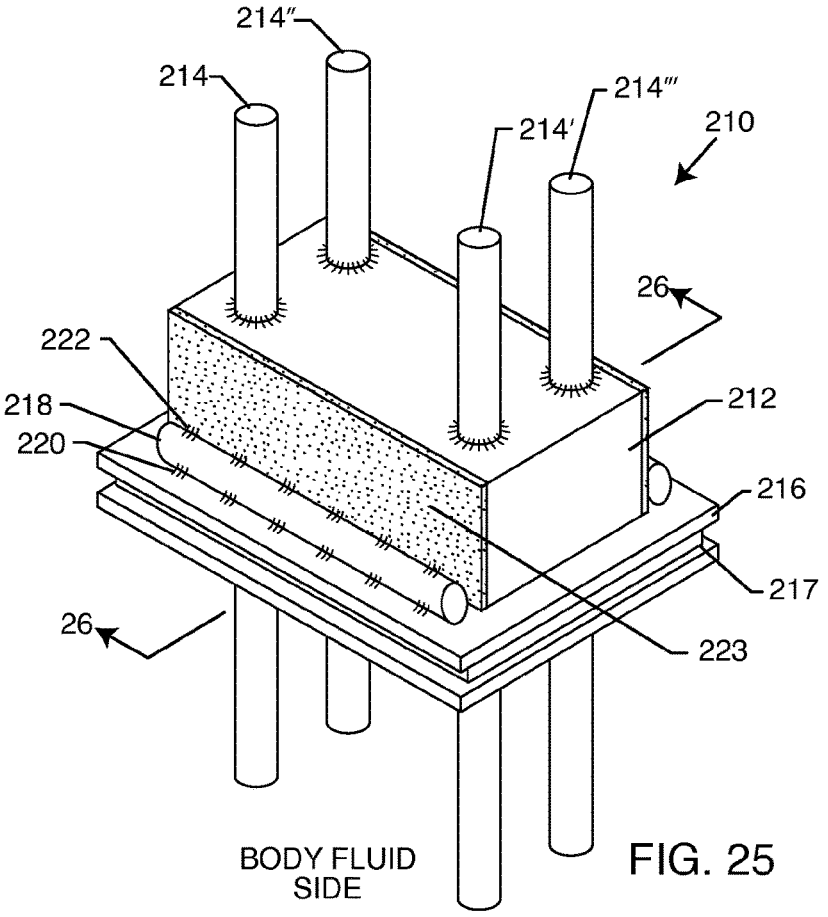
FIG. 25 is a perspective view of an exemplary feedthrough capacitor embodying the present invention.

FIG. 25 illustrates a filtered feedthrough assembly of the present invention 210. Illustrated is a ferrule 216 of the hermetic seal. The ferrule is generally of titanium. In this case, it has a continuous slot 217, which can receive the can halves of an active implantable medical device, such as a cardiac pacemaker. These titanium can halves are then laser welded to the titanium ferrule 216. In general, a feedthrough capacitor 212 would be oriented towards the inside of the can to protect it from body fluids. In this case, there are novel round platinum iridium wires 218, which have been laser welded 220 directly to the ferrule 216. Laser weld 220 could also be replaced by a resistance weld or a secondary braze operation at a lower temperature using for example, but not limited to, copper based brazing materials such as Cu—SiI or Ti—Cu—SiI, silver based brazing materials such as SiIvaloy (Ag—Cu—Zn) or Gapasil (Ag—Pd—Ga), gold based brazing materials such as Au—Cu, Au—Cu—Ag, or Au—Cu—Ni, or palladium based braze materials such as Pd—Ni—Si. A capacitor ground metallization 223 is attached using solder or thermal-setting conductive adhesives 222 to the platinum iridium wire 218. The platinum iridium wire can actually be of any noble material including platinum, gold and its alloys, palladium and its alloys, silver and its alloys and combinations thereof. Leadwires 214 through 214''' pass through the feedthrough capacitor and through the hermetic seal. This is best understood by referring to FIG. 26, which is taken from section 26-26 from the structure of FIG. 25.

Figure 26:
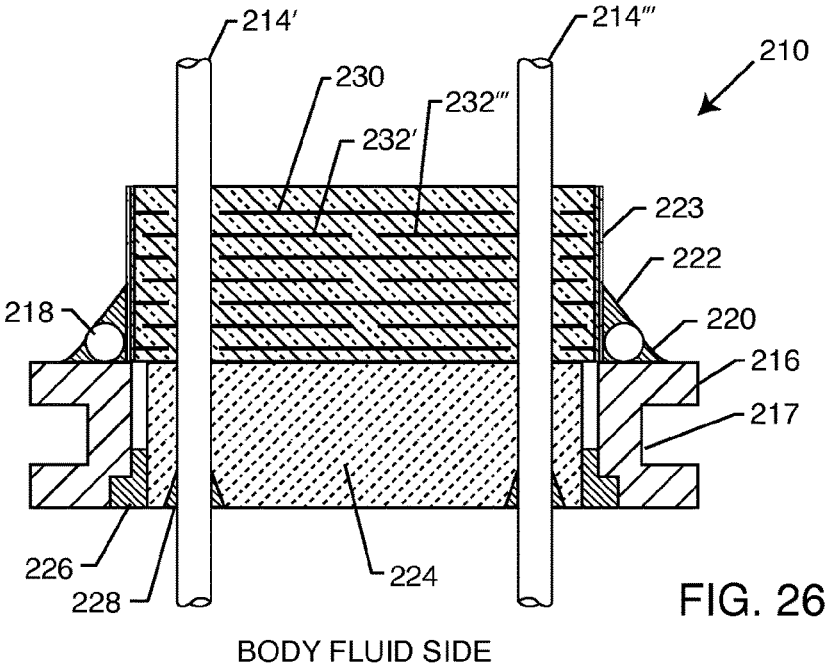
FIG. 26 is a sectional view taken along line 26-26 of the structure of FIG. 25.

FIG. 26 illustrates the laser weld 220, the noble wire 218 and the solder or thermal-setting conductive adhesive 222. In FIG. 26, one can see the capacitor interior electrode plate stacks. A ground electrode plate stack 230 and an active electrode plate stack are designated by 232' and 232''' which are connected respectively to terminal pins 214' and 214'''. (The preformed capacitor feedthrough hole, inside diameter metallization of the capacitor feedthrough hole and electrical connection material has been omitted for clarity. It is understood by one skilled in the art that various structures and techniques are used to connect the active electrode plates to the lead wires. In this case, the active electrodes 232 are shown directly contacting the lead 214'. It will be appreciated that these other features which have been omitted incorporate part of the invention.) On the body fluid side of the capacitor, one can see gold brazes 226 and 228. Gold braze 226 connects the ferrule 216 to the alumina insulator 224 providing a robust mechanical and hermetically sealed joint. Gold braze 228 forms a robust mechanical and hermetic seal between the alumina ceramic 224 and the leads 214.

Referring once again to FIGS. 25 and 26, one can see that the leadwire 218 provides a very novel feature, that is, electrical connection material 222 does not directly attach to the ferrule 216. The reason for this is that the ferrule is typically of titanium, which commonly forms titanium oxides. Titanium oxides are very resistive and can also act as semiconductors. This means that a direct connection to titanium would degrade the effectiveness of the capacitor ground electrode plate stack. The noble wire 218 acts as an intermediate surface. By laser welding it to the titanium ferrule 216, one forms a very strong oxide resistant metallurgical bond. Now, the surface on wire 218 is relatively oxide free. For example, it could be gold, platinum or the like which are oxide resistant at room temperatures. In fact, it would be preferable if the wire 218 be pure platinum and not platinum iridium. The reason for this is that the iridium can form oxides.

Referring once again to FIG. 26, shown is that the gold brazes forming the hermetic seals 226 and 228 are on the body fluid side. There are a number AIMD manufacturers that prefer having the gold braze on the body fluid side. By having the gold braze in this location, however, making a connection to the capacitor's outside perimeter or diameter metallization 223 to the same gold braze surface becomes impossible. In other words, as previously described in FIG. 18, there is no possibility to provide the gold bond pad 165, which is a contiguous part of the hermetic seal braze 226. This is major driving feature of the present invention in that a methodology is provided so that the feedthrough capacitor can be properly grounded to an oxide resistant surface even when the gold brazes are disposed on the opposite side (the body fluid side).

Figure 27:
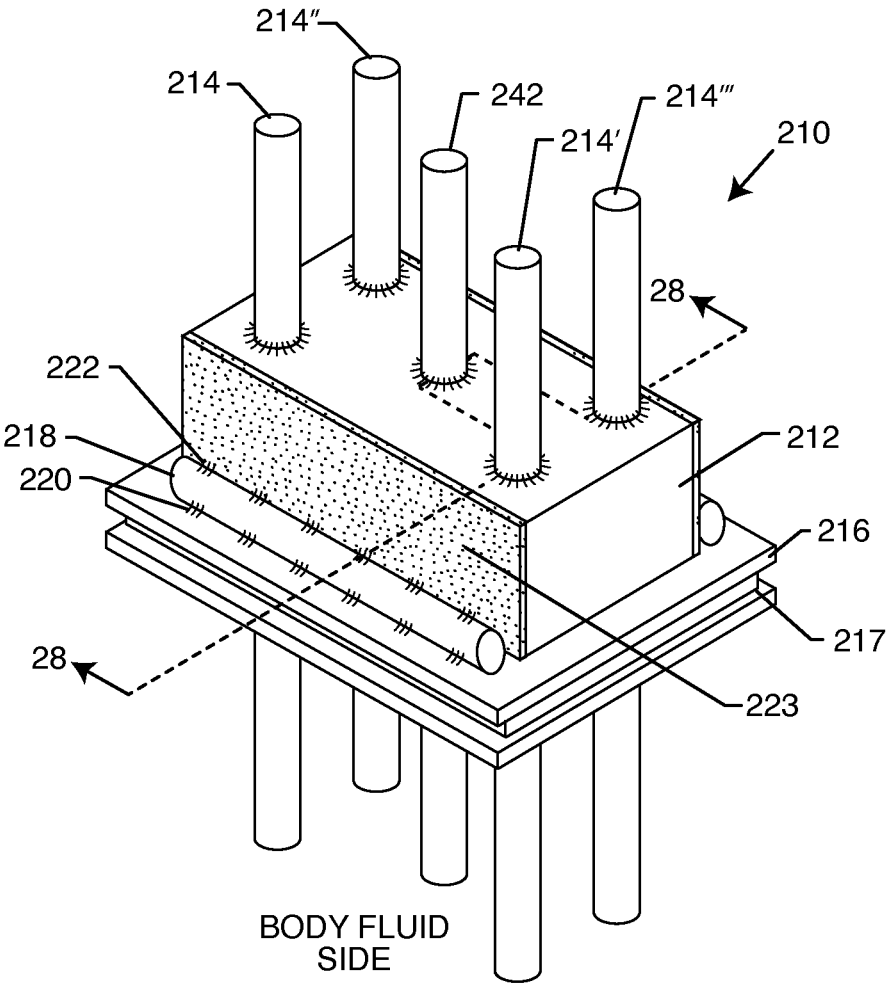
FIG. 27 is a perspective view of another exemplary feedthrough capacitor embodying the present invention.
Figure 28:
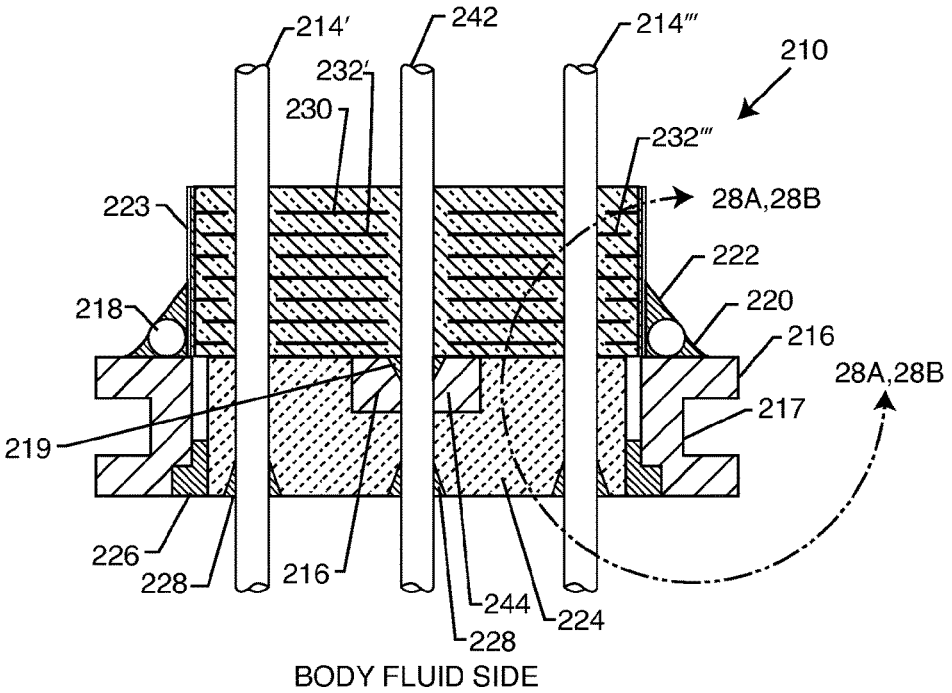
FIG. 28 is a sectional view taken along line 28-28 of the structure of FIG. 27.

FIGS. 27-28 are similar to FIGS. 25-26 but now show a peninsula structure 244 formed as part of the ferrule 216. A ground wire 242 is attached to the peninsula 244. As can be seen best in the cross-section of FIG. 28, the ground wire 242 is not connected to the ground electrode plates 230. The ground electrode plates are still electrically coupled to the metallization 223 which is then electrically coupled to the ferrule 216 through the weld 220, the wire 218 and the thermosetting conductive adhesive 222 or solder.

Referring once again to FIG. 27A, one can see that the grounded peninsula 244, which is a continuous part of the machined ferrule 216, is electrically attached via material 219 to the grounded pin 242. The ground material could be a laser weld, a gold braze, a solder, a thermal-setting conductive adhesive or the like. In general, pin 242 is provided as a convenience to the AIMD manufacturer to either ground the internal circuit board, or to provide an addition pacing vector to a conductor of an implanted lead (not shown) or both. The electrical ground attachment from the peninsula 244 to lead 242 is very low in resistivity, meaning that it would also be applicable for high voltage implantable cardioverter defibrillator applications. In such an application, a very light shock current would flow through this ground joint to an external electrode (not shown).

Figure 28A:
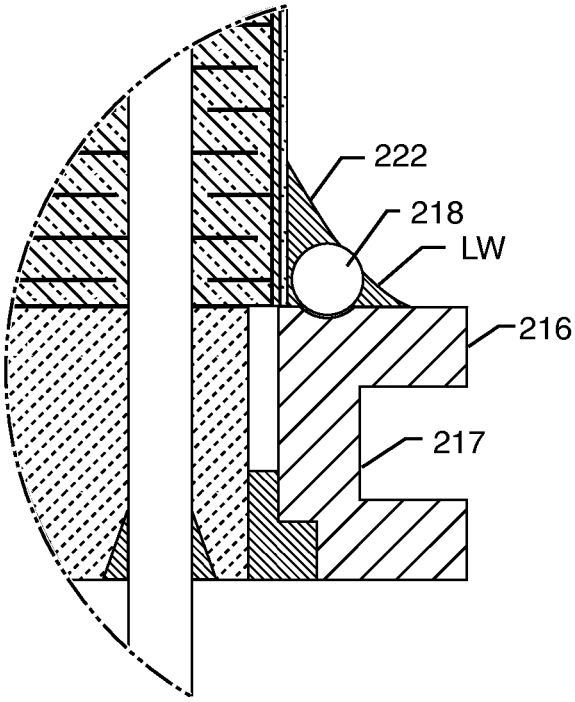
FIG. 28A is an enlarged view of a novel embodiment of a similar structure of FIG. 28 taken along lines 28A-28A.

FIG. 28A is an enlarged view of a new embodiment of the structure from FIG. 28 taken from lines 28A-28A now showing the wire 218 recessed into the ferrule 216. In this way the wire 218 may be positioned and affixed in a more efficient manner.

Figure 28B:
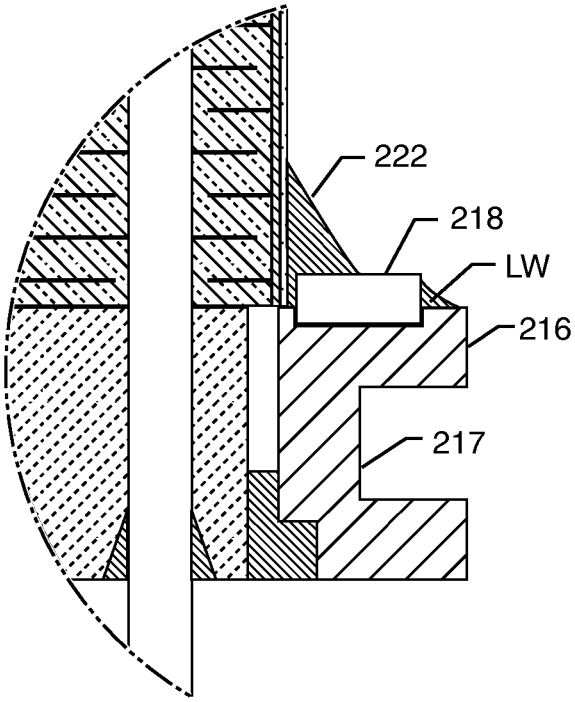
FIG. 28B is another embodiment of the structure of FIG. 28A now showing a rectangular shaped structure attached to the ferrule.

FIG. 28B is an enlarged view of another embodiment of the structure from FIG. 28 taken from lines 28B-28B now showing the rectangular wire 218 recessed into the ferrule 216. In this way the rectangular wire 218 may be positioned and affixed in a more efficient manner.

Figure 27A:
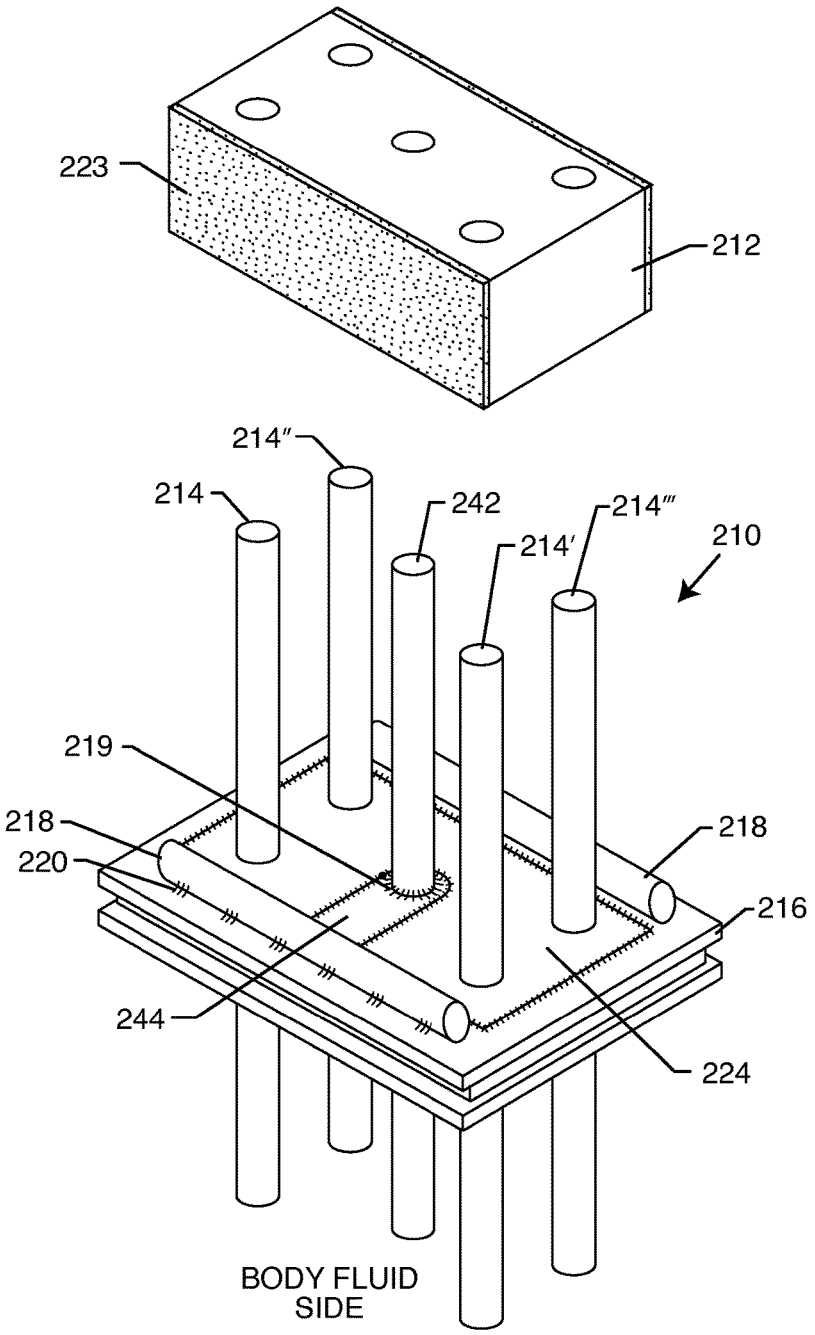
FIG. 27A is an exploded view of the structure of FIG. 27 showing the peninsula portion of the ferrule.
Figure 28C:
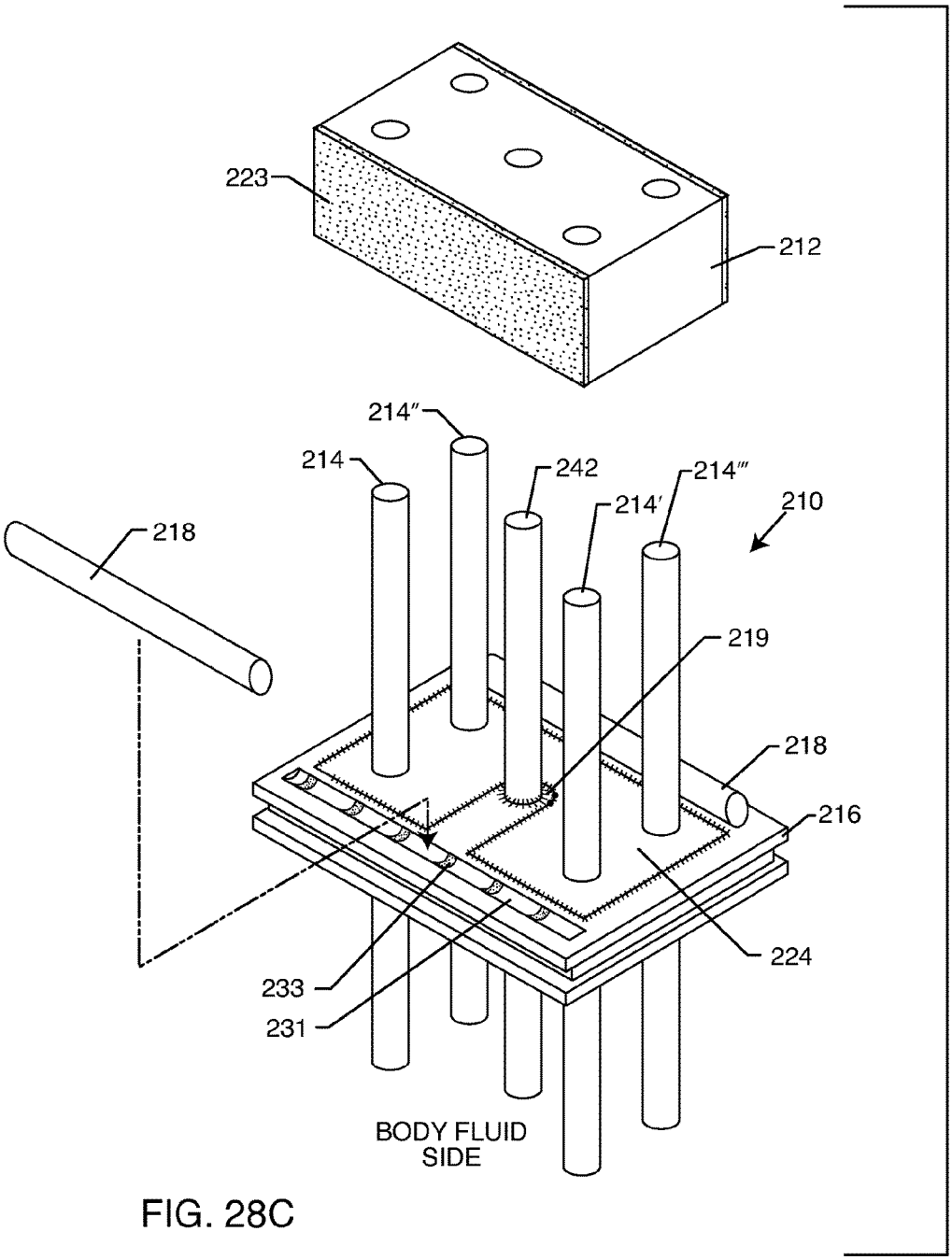
FIG. 28C is a view similar to 27A except now showing a recess on the ferrule for the wire to fit within.

FIG. 28C shows a perspective view similar to FIG. 27A now with the recess 231 and inserts 233 clearly shown. The inserts 233 are placed in the recess 231 before the wire 218 is placed and may be gold metal, gold brazed or any of the material variations and connection methods already described herein.

Figure 29:
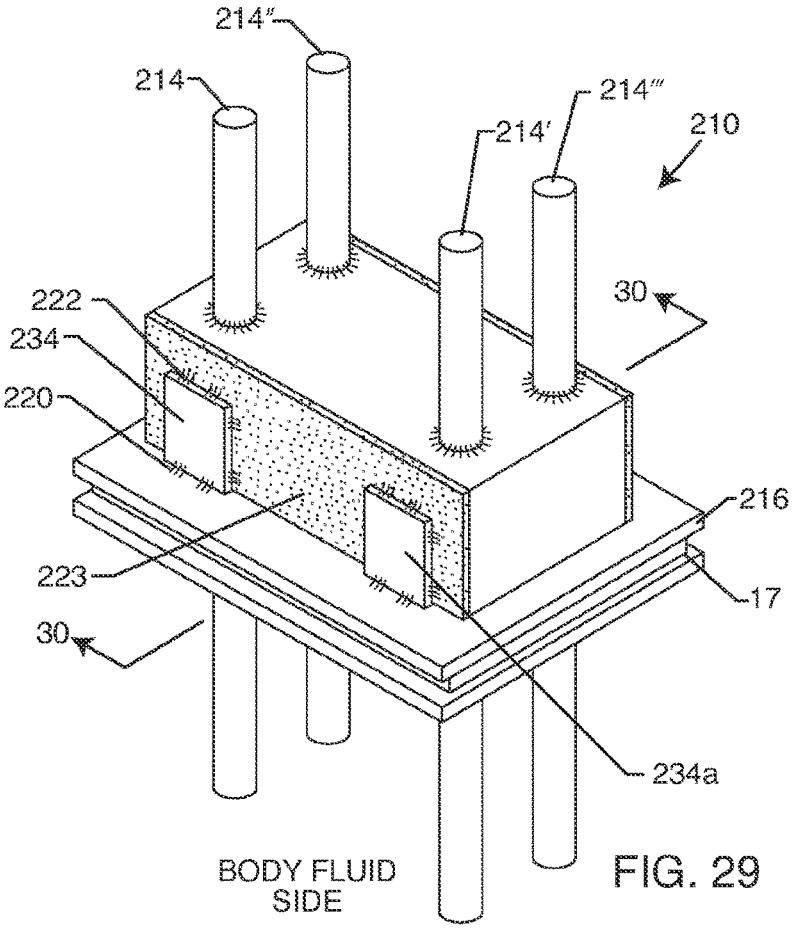
FIG. 29 is a perspective view of another exemplary feedthrough capacitor embodying the present invention.

FIG. 29 is similar to FIG. 25 and illustrates that the two wires 218 could be replaced by a number of pads 234 as shown. In general, the pads could be formed as a continuous part (not shown) of the machining of the ferrule 216 or they could be added as a subsequent assembly by gold brazing or laser welding 220 as shown. The pads 234 would be of the same noble materials previously described as for the wire 218. This means that a convenient oxide resistant electrical connection 222 could be made using solder or thermal-setting conductive adhesives.

Throughout the invention, the intermediate biostable and oxide resistant intermediate structure, such as lead 218 shown in FIG. 27 with pad 234 as illustrated in FIG. 29, must have the following properties: 1) they must be weldable or brazable to the titanium ferrule 216; 2) this weld or braze joint must break through any oxides of titanium and form a metallurgical bond between the structure 218 or 220 and the ferrule 216; and 3) the intermediate biostable wire of pad 234 must be connectable to the capacitor's external metallization 223. The number of connection methods to the capacitor's external metallization is limited. This includes solders, solder paste and all types of thermal-setting inductive adhesives. In general, although possible, it is not reliably possible to braze or weld directly to the capacitor's external metallization 223, hence this option is not a preferred embodiment. In summary, the biostable wire 218 or pad 234 need not be platinum, but it can consist of a long list of metals that would meet the above criteria. Obvious choices would be gold, palladium, tantalum, and niobium. Additional non-limiting considerations include: tungsten, iridium, ruthenium, rhodium, silver, osmium, or combinations thereof. Other nonlimiting examples include platinum based materials such as platinum-rhodium, platinum-iridium, platinum-palladium, or platinum-gold, and naturally occurring alloys like platiniridium (platinum-iridium), iridiosmium and osmiridium (iridium-osmium).

Figure 30:
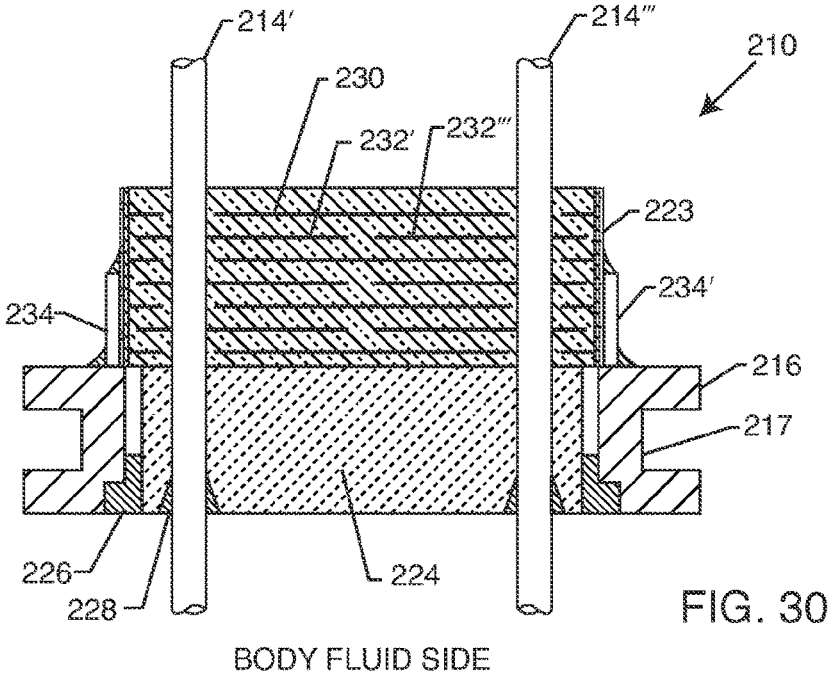
FIG. 30 is a sectional view taken along line 30-30 of the structure of FIG. 29.

FIG. 30 is a sectional view taken from section 30-30 from FIG. 29 illustrating that the pads 234 and 234' are disposed on both sides of the capacitor. It will be obvious to those skilled in the art that they could also be disposed at the ends of the capacitor (not shown). It will be appreciated to one skilled in the art that the pads could be connected. For example, referring once again to FIG. 27, pads 234 and 234a could be filled in between so that there was one large continuous pad. These pads could also have holes in them to further facilitate the electrical attachment between the pad and the capacitor external ground metallization 223.

Figure 31:
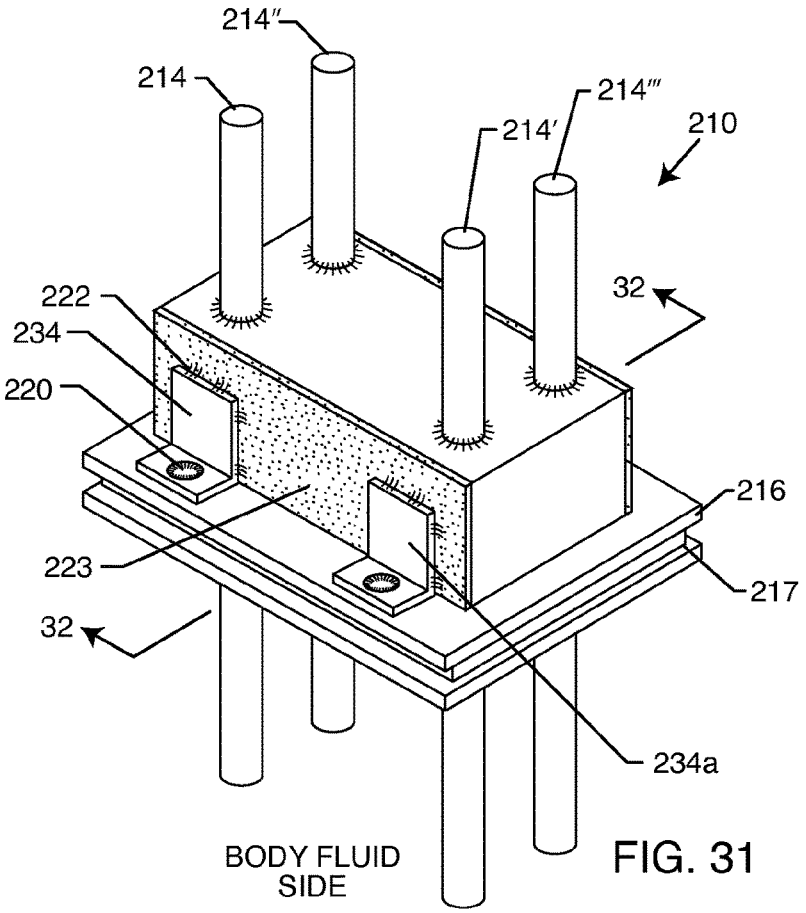
FIG. 31 is a perspective view of another exemplary feedthrough capacitor embodying the present invention.
Figure 32:
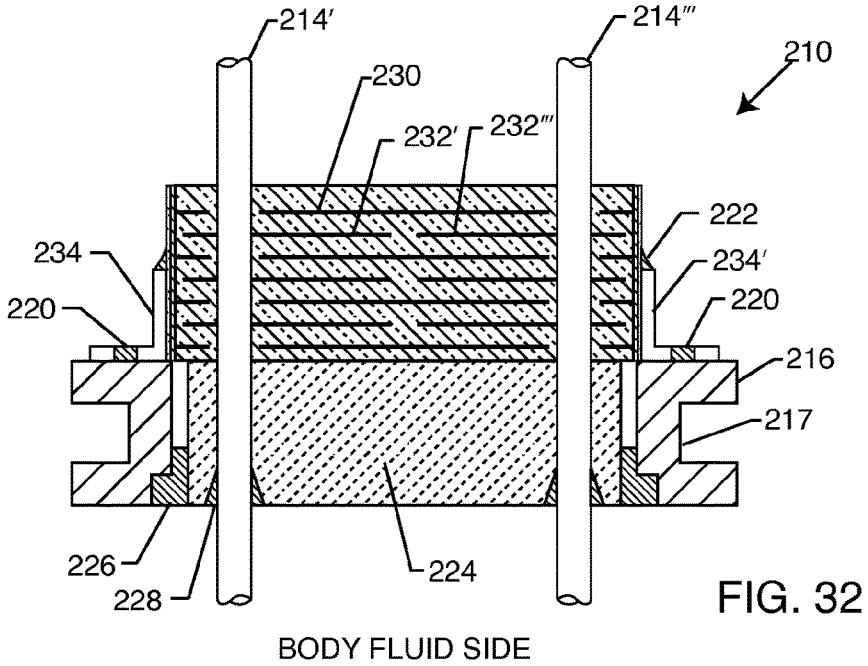
FIG. 32 is a sectional view taken along line 32-32 of the structure of FIG. 31.

FIG. 31 is a perspective view of another embodiment similar to FIGS. 25-30 now showing a different configuration of pad 234. Here, pad 234 is shown in an L-shape. There is a hole in the bottom of the pad facilitating the laser weld or braze 220 to the ferrule 216. FIG. 32 is a sectional view taken along line 32-32 from the structure of FIG. 31.

Figure 33:
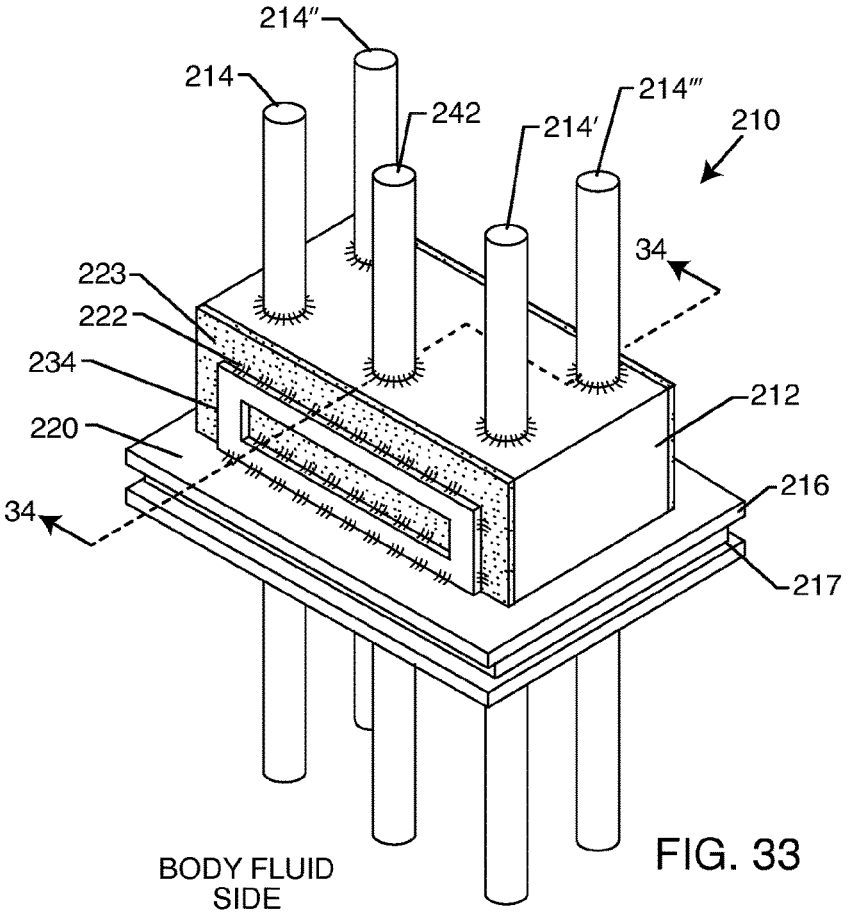
FIG. 33 is a perspective view of another exemplary feedthrough capacitor embodying the present invention.
Figure 34:
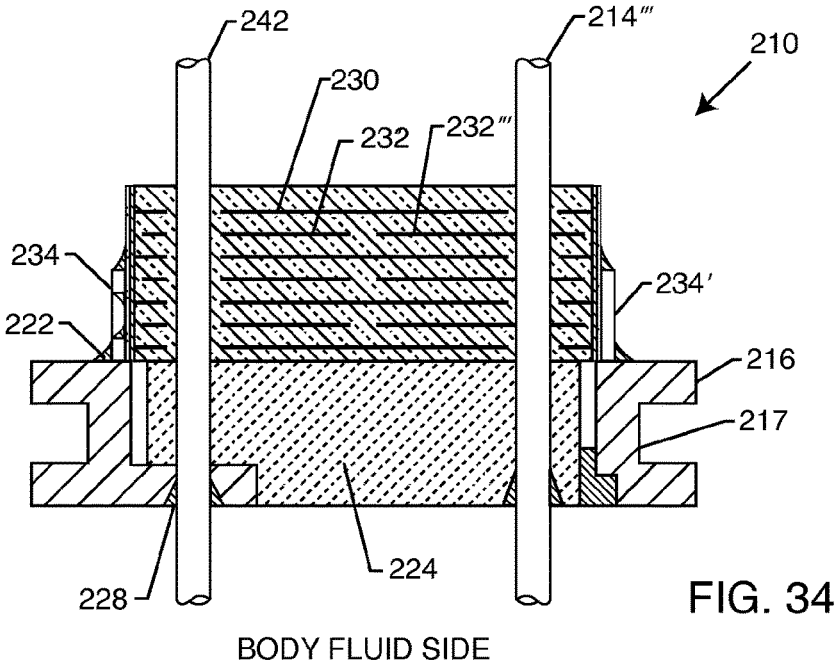
FIG. 34 is a sectional view taken along line 34-34 of the structure of FIG. 33.

FIG. 33 is a perspective view of yet another embodiment of a feedthrough capacitor assembly 210 similar to FIGS. 25-32. Here the pad 234 is a long pad that spans the length of the long side of the capacitor 212. The pad 234 has a large hole to facilitate the placement and bonding of the conductive adhesive 222. FIG. 34 is a sectional view taken from lines 34-34 from the structure of FIG. 33.

FIG. 34 is a sectional view taken from section 34-34 from FIG. 33. It shows the long bracket 234 cross-section along with laser weld 222.

Figure 35:
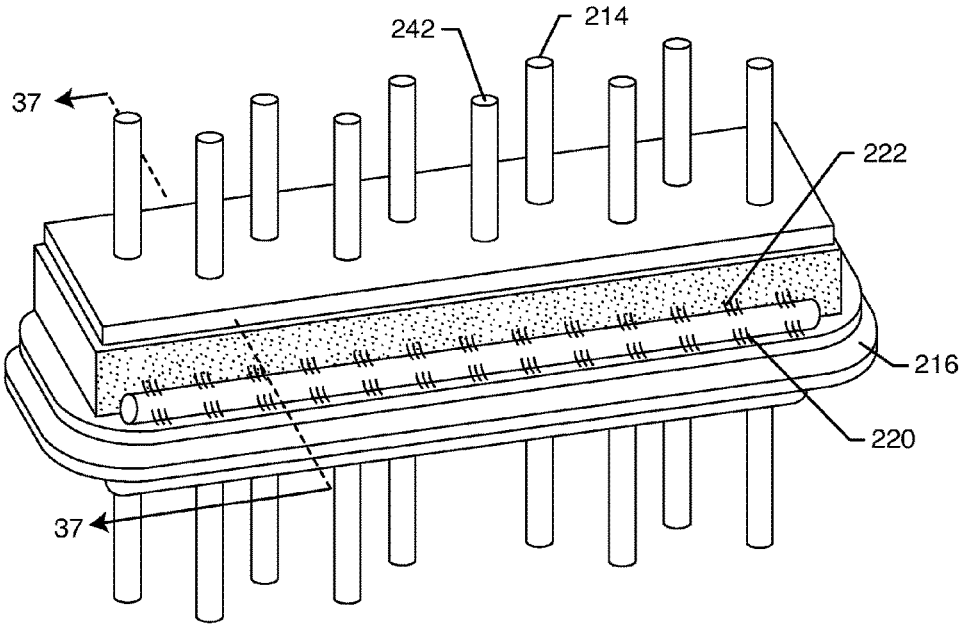
FIG. 35 is a perspective view of another exemplary feedthrough capacitor embodying the present invention.
Figure 36:
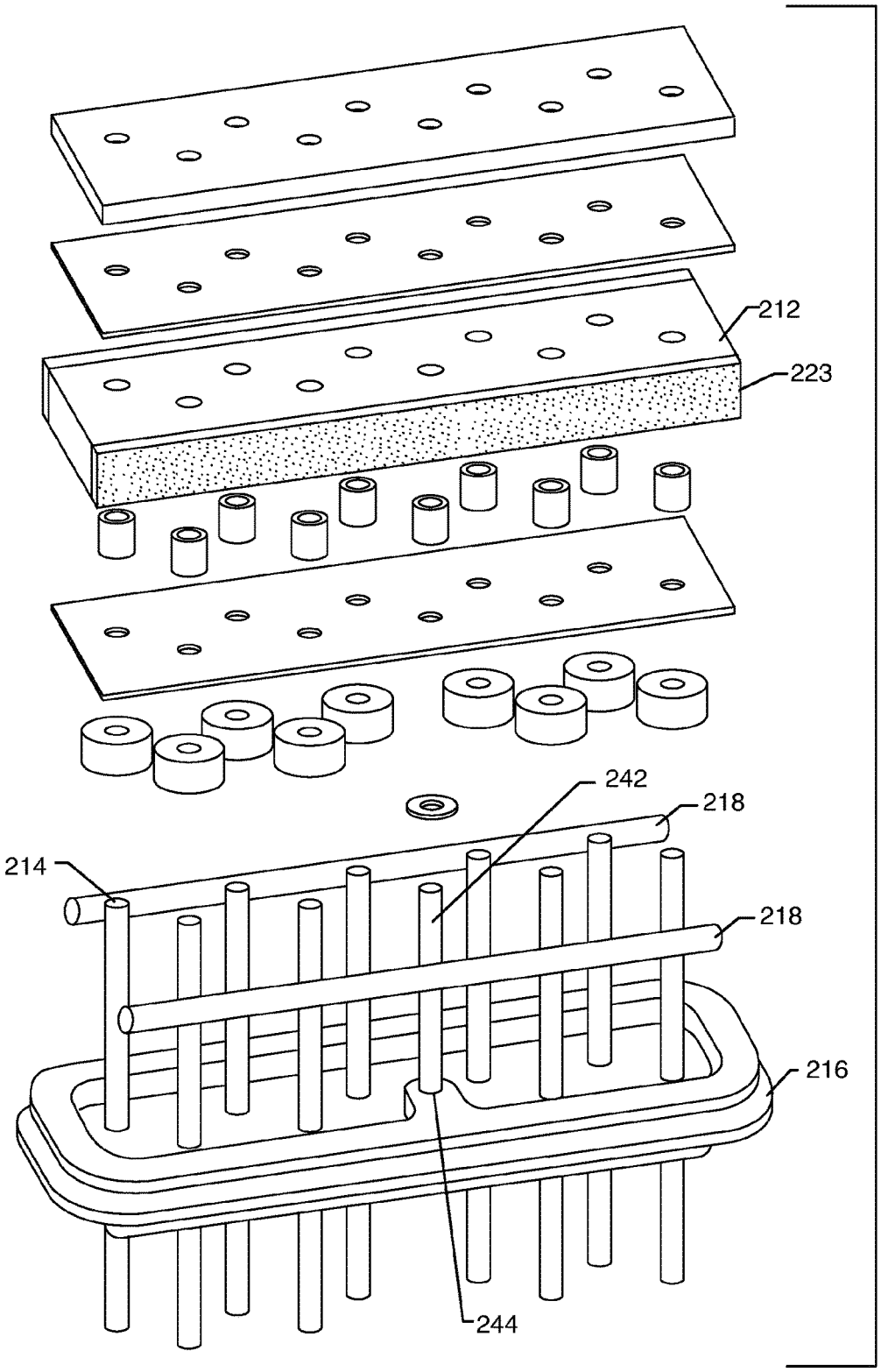
FIG. 36 is an exploded view of the structure of FIG. 35 showing the peninsula portion of the ferrule.

FIG. 35 is similar to FIG. 25 except in this case there are more terminal pins 214. Accordingly, it is necessary that the oxide-free biostable wire 220 be longer and have more laser welds 222. This is because it would be undesirable to have a long distance between a filtered terminal pin and its associated ground. This is because inductance and resistance can build up across an internal ground plane, thereby degrading the RF filtered performance of a distal filtered pin. FIG. 36 is an exploded view of the structure of FIG. 35. In FIG. 36, the ground pin 242 is shown laser welded or gold brazed into the ferrule 216 in the peninsula area 244. In this case, the capacitor is a conventional capacitor wherein the ground electrode plates are terminated 223 with metallization disposed along the two long outside ends of the capacitor 212. In this case, there is no connection between terminal pin 242 and the capacitor's ground electrode plate stack 230. In a different embodiment (not shown), a capacitor's ground electrode plates could be connected to this grounded pin as completely described in U.S. Pat. No. 6,765,779, the contents of which are incorporated herein by reference. Referring once again to FIGS. 35-37, an alternative is given wherein a direct connection to terminal pin 242 and the grounding of the capacitor's electrode stacks 230 is nonexistent. That is, the electrical connection is between the capacitor metallization 223 and the noble wires 218.

Figure 37:
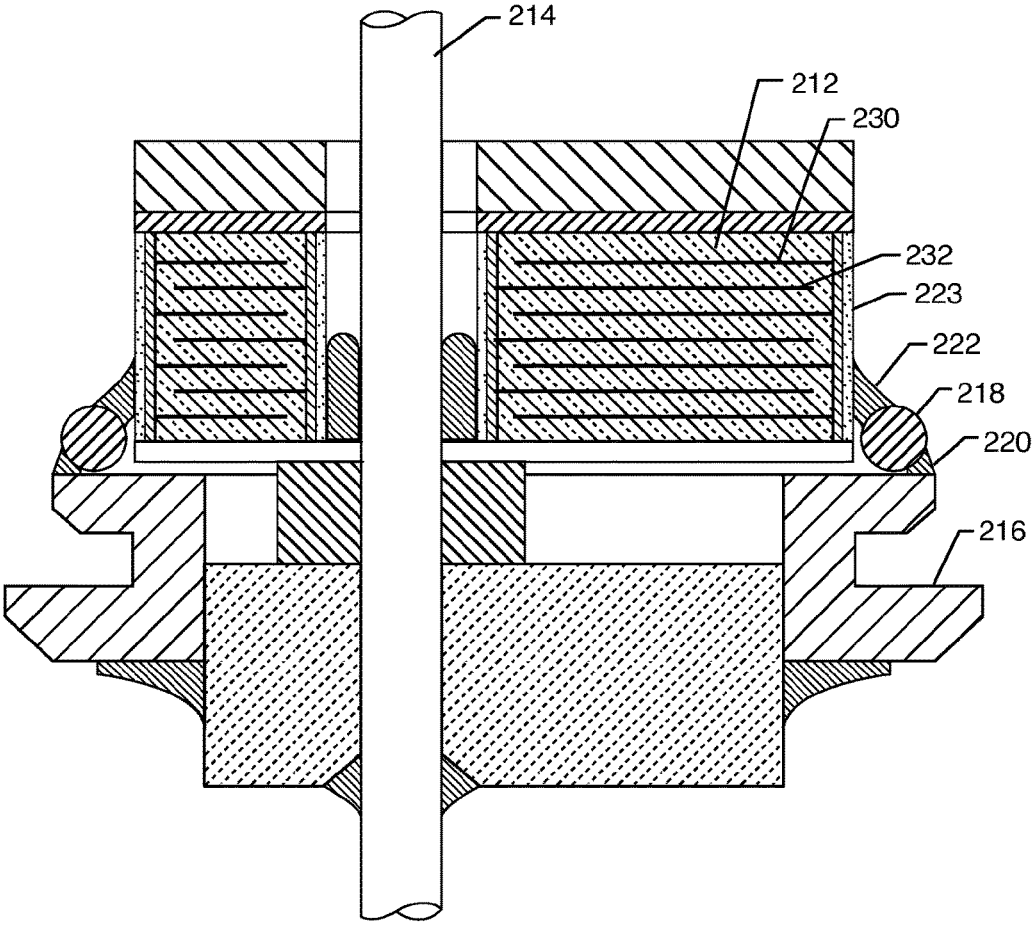
FIG. 37 is a sectional view taken along line 37-37 of the structure of FIG. 35.

FIG. 37 is a sectional view taken from section 37-37 from FIG. 35 illustrating that any one of the active pins 214 passes through feedthrough holes near the center of the capacitor 212 in a staggered pattern where the pin 214 makes contact with its own individual set of active electrode plates (not shown) or many active electrode plates. The ground electrode plates contact the capacitor's long-side perimeter metallization 223 and then electrical attachment material, which can be solder or thermal-setting conductive adhesive, attaches the capacitor ground metallization 223 to the noble wire 218.

Figure 38:
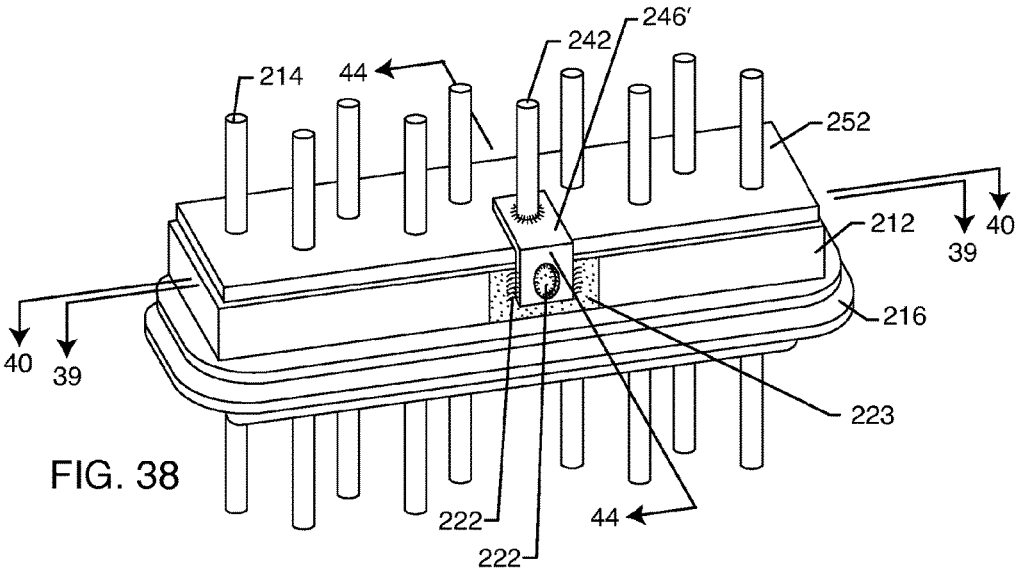
FIG. 38 is a perspective view of another exemplary feedthrough capacitor embodying the present invention.

FIG. 38 is similar to FIG. 35, which illustrates an alternative method of grounding the capacitor's ground electrode stack 230. Referring back to FIG. 36, one can see the novel ferrule pedestal 244 to which ground pin 242 is electrically and mechanically attached. In FIG. 28, ground pin 242 is electrically attached to the ferrule 216 and is thereby grounded in a similar manner as shown in FIG. 36. A novel L-shaped clip 246' is electrically attached to ground pin 242 and engages a portion of the capacitor's external ground metallization 223. This is best illustrated in FIG. 28, where the ground clip 246' being electrically connected 222 to the capacitor's ground metallization 223 is shown.

Referring back to FIG. 38, illustrated is clip 246' disposed on the top surface of the capacitor 212. There is an insulating structure 252 that is disposed on top of capacitor 212. This can be a conformal coating of insulation, an insulation sheet with adhesive layer, or even an alumina ceramic thin sheet of insulation. For the case where this insulation sheet 252 is alumina ceramic, it may have a cut-out pocket so that the clip 246' drops down into it and fits flush with the top of the insulating layer 252. This would help to hold the clip 246' in place and to index it.

Figure 39:
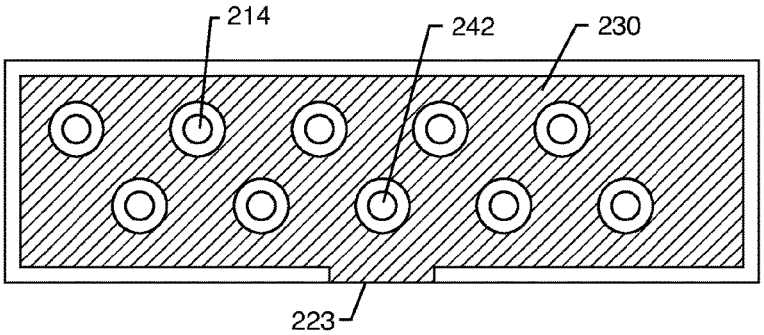
FIG. 39 is a sectional view taken along line 39-39 of the structure of FIG. 38 now showing a ground electrode plate.

FIG. 39 shows the ground electrode plate 230 which does not make contact with the leadwires 214 or the grounded wire 242. The ground electrode plate 230 makes contact with metallization 223 which is then in electrical contact with novel pad 246'.

Figure 40:
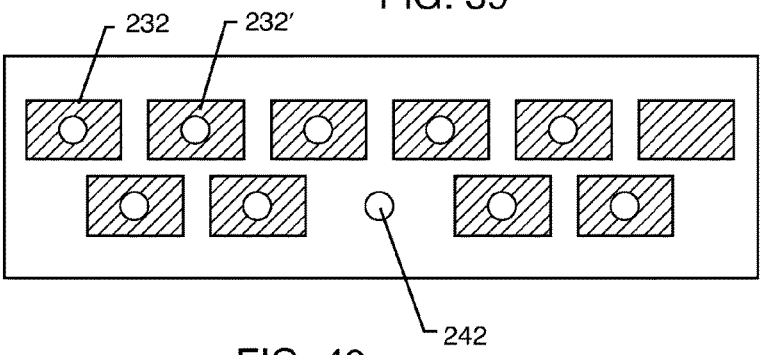
FIG. 40 is an sectional view taken along line 40-40 of the structure of FIG. 38 now showing an active electrode plate.

FIG. 40 shows a multitude of active electrode plates 232 electrically coupled to the leadwires 214. Note that the grounded pin 242 lacks an active electrode plate 232.

Figure 41:
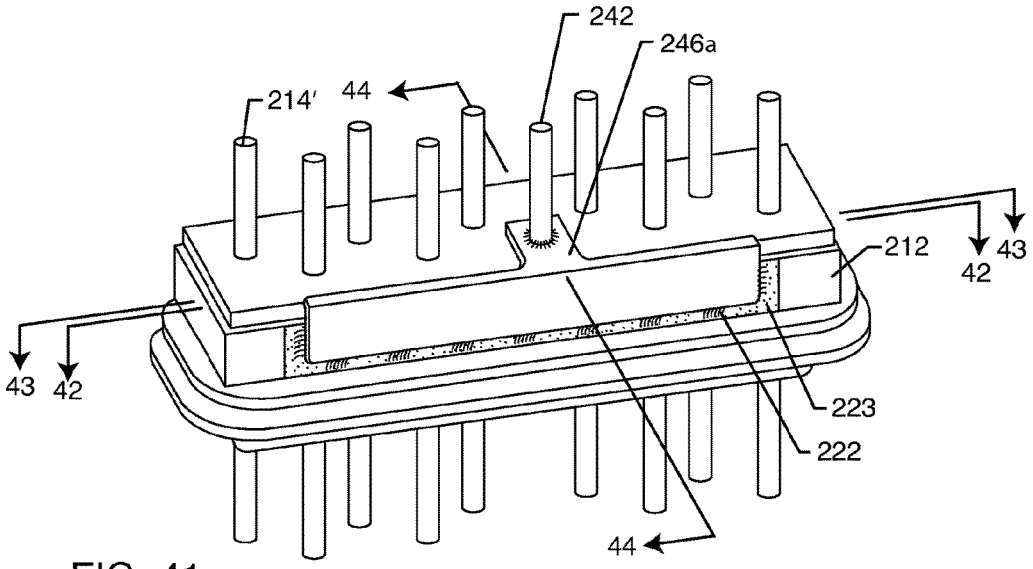
FIG. 41 is a perspective view of another exemplary feedthrough capacitor embodying the present invention.
Figure 42:
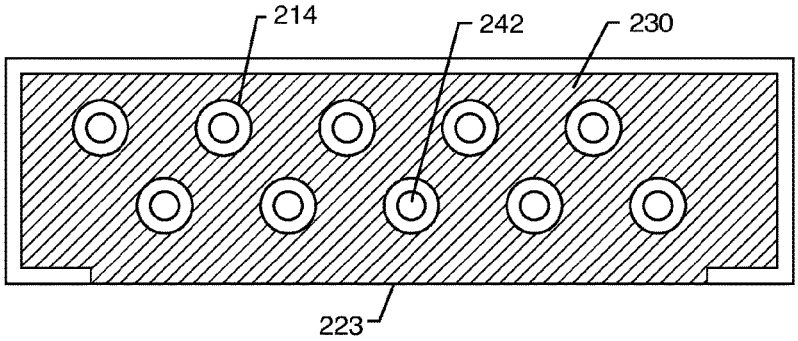
FIG. 42 is an sectional view taken along line 42-42 of the structure of FIG. 41 now showing a ground electrode plate.
Figure 43:
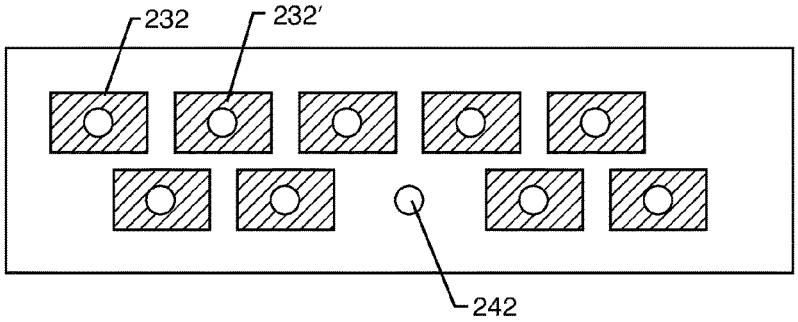
FIG. 43 is an sectional view taken along line 43-43 of the structure of FIG. 41 now showing an active electrode plate.

FIGS. 41-43 are very similar to FIGS. 28-30. FIGS. 41-43 show a different embodiment of the novel pad 246a. Pad 246a is longer along the length of increased metallization 223. This design would increase filter performance due to the shortened electrical pathways. In this way, the inductance across the ground planes of the capacitor is greatly reduced. This means that outer pins 214 will have improved attenuation and greater insertion loss than the structure previously illustrated in FIG. 38.

Figure 44:
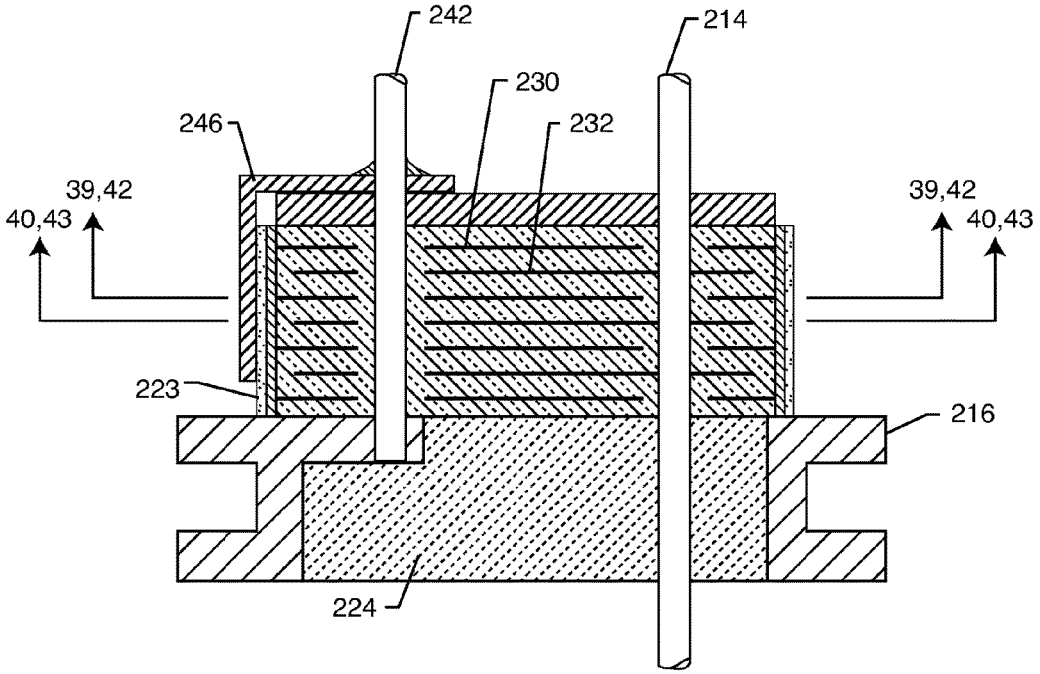
FIG. 44 is a sectional view taken along lines 44-44 of the structures of both FIGS. 38 and 41.

FIG. 44 is a sectional view for both FIGS. 38 and 41. One can see better the peninsula or extension that attaches to the ground wire 242. It will be understood that novel pad 246 could also extend over the opposite side metallization and also make electrical contact. This would further improve filter performance by lowering electrical pathway lengths.

Figures 45A, 45B, 45C:
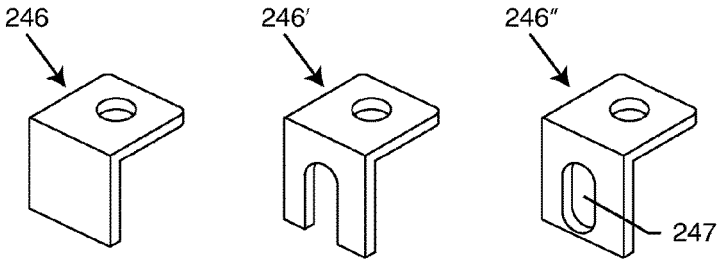
FIGS. 45A, 45B and 45C are perspective views of various embodiments of the novel ground attachments shown in FIGS. 38, 41 and 44.

FIGS. 45A, 45B and 45C illustrate various types of L-shaped clips 246. In FIG. 45C, one can see the advantage of having a clip with an elliptical hole 247 because this allows electrical connection material 222, which can be a solder or a thermal-setting conductive adhesive, to be placed on the outside of the clip and also inside the elliptical hole. This increases the electrical contact area and thereby reduces the resistance as well as improves mechanical strength.

Figure 46:
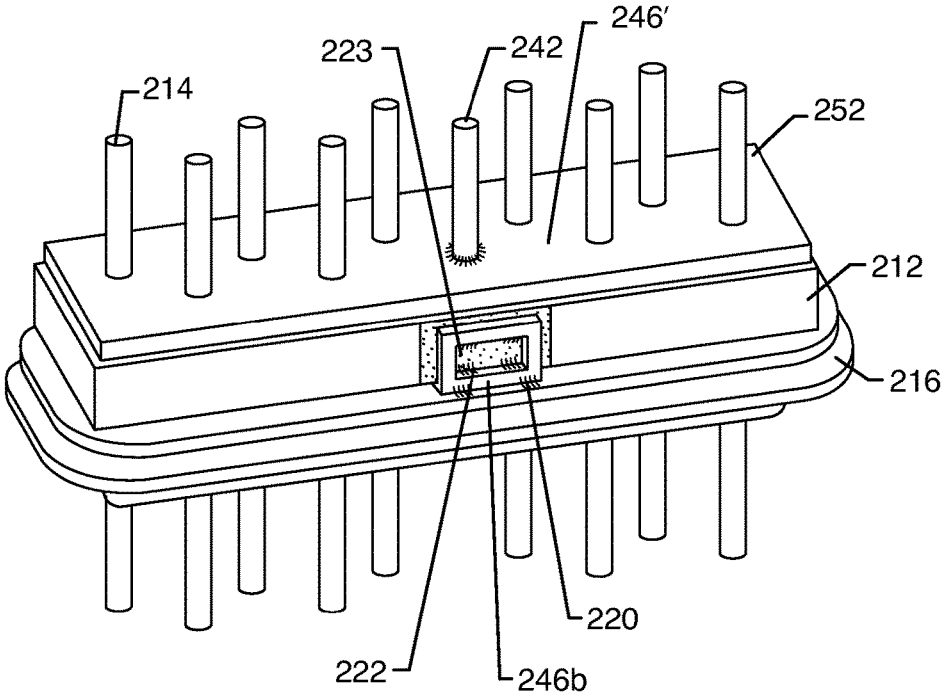
FIG. 46 is a perspective view of another exemplary feedthrough capacitor embodying the present invention.
Figure 47:
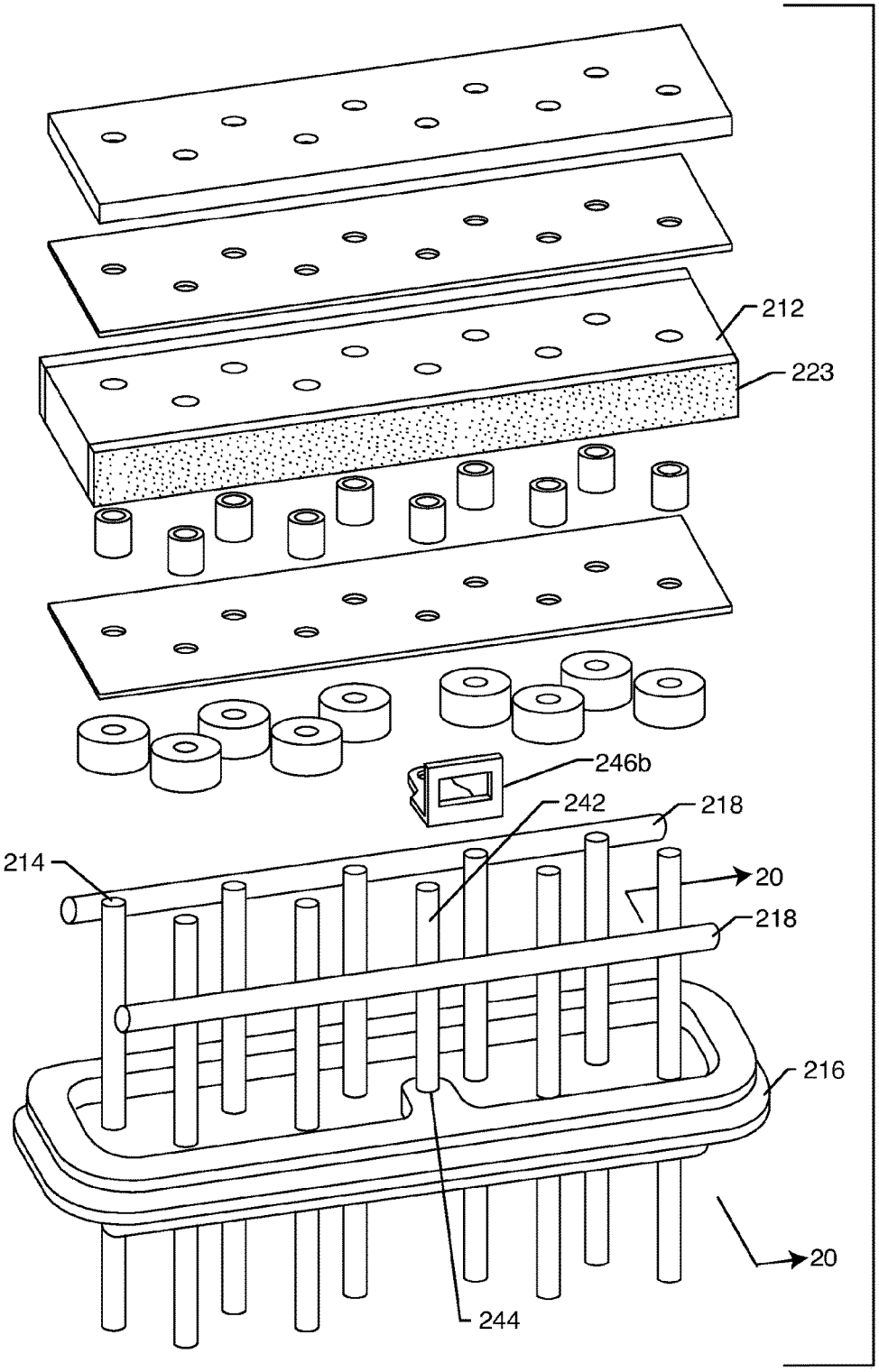
FIG. 47 is an exploded view of the structure of FIG. 46 showing the novel ground attachment below the capacitor.

FIGS. 46 and 47 are an alternative embodiment of clip 246b previously illustrated in FIGS. 38 and 41. The novel clip 246b is under the capacitor 212 sandwiched between the ferrule 216 and the capacitor 212. A hole is also in the clip 246b to facilitate placement of conductive adhesive 222. FIG. 47 is an exploded view that best shows the shape of novel clip 246b.

In the alternative embodiment shown in FIG. 46, the clip 246 is disposed underneath the capacitor 212 and electrically and mechanically attached directly to the peninsula structure. Having the clip 246' disposed underneath the capacitor 212, and then coming up on the side as is illustrated, would improve the RF performance of the capacitor. Effectively, this would shorten the ground pin 242 to almost zero thereby reducing the impedance and inductance of the ground clip 246'. A notch (not shown) could be put in the ferrule 216 of the hermetic terminal to facilitate the clip coming out through the bottom so that the capacitor 212 still would sit flush on top of the ferrule structure 216.

Figure 51:
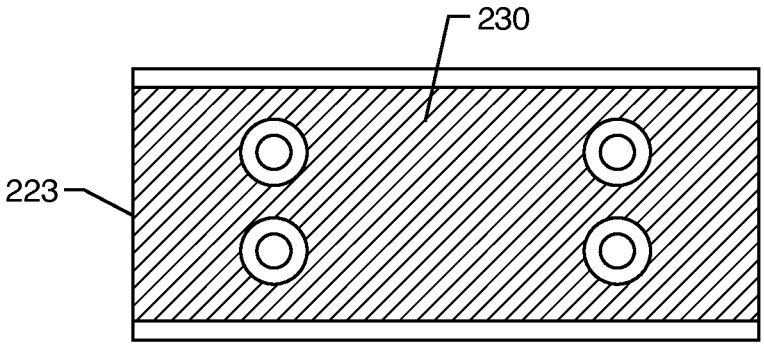
FIG. 51 is a sectional view taken along line 51-51 of the structure of FIG. 50 now showing a ground electrode plate.
Figure 52:
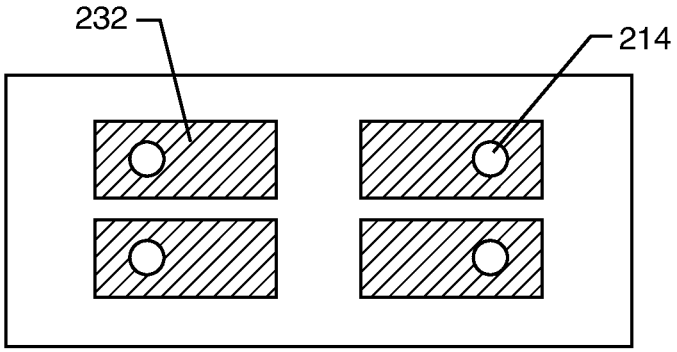
FIG. 52 is a sectional view taken along line 52-52 of the structure of FIG. 50 now showing an active electrode plate.
Figure 53:
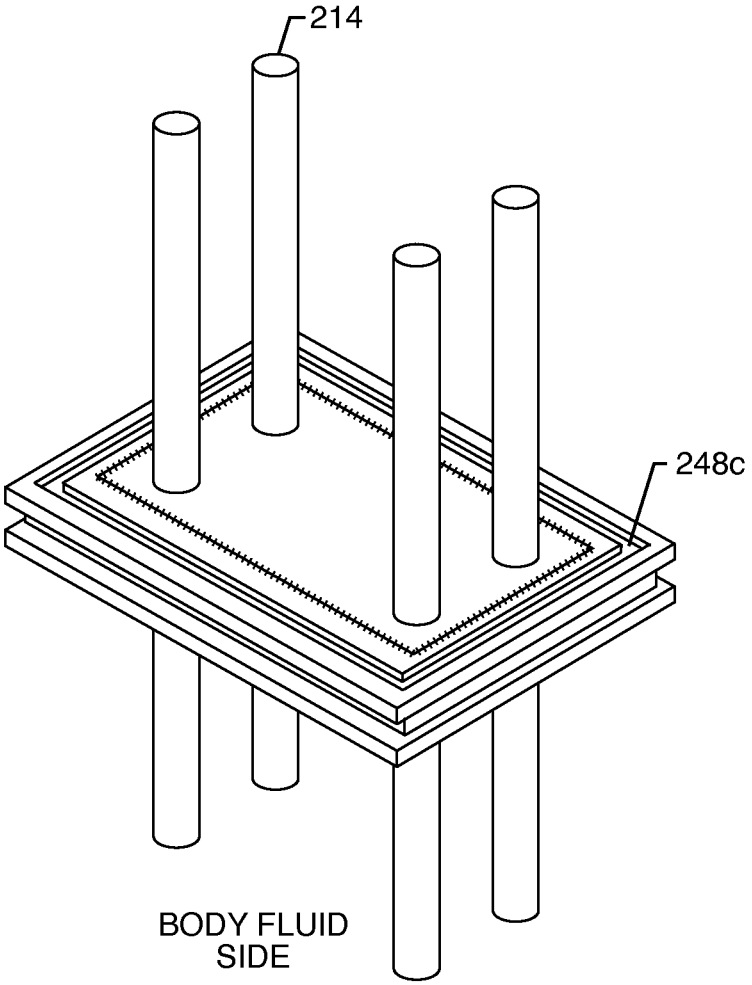
FIG. 53 is a perspective view of another exemplary feedthrough embodying the present invention now showing novel ground attachments around the continuous perimeter of the ferrule.

FIGS. 48-53 are similar to FIGS. 25-34 except that in this case pockets 248 and noble metal inserts 250 have been formed so that an oxide resistant electrical attachment 222 can be made between the capacitor ground metallization 223 and the ferrule 216. An alternative embodiment 250' is shown where first, a brazing perform, such as a gold braze perform 250a, is placed and then a platinum cap 250b is placed over it. Alternative metals may be used as noted earlier. In addition, instead of a braze 250a, one could use a resistance weld or lower temperature brazes such as those listed previously with the Cu—SiI or Ti—Cu—SiI examples. Platinum pad 250b would be slightly longer in the length direction and slightly longer in the width direction than the underlying pre-form 150A. This overlaying would prevent it from reflowing and leaking out during a gold braze operation. In addition, the pad 250b would protrude above the surface of the ferrule. This turns out to be very convenient during electrical attachment of the feedthrough capacitor (not shown) outside perimeter metallization 223. In other words, the protruding pad 250b would provide a convenient stop for a solder paste, a solder pre-form or a thermal-setting conductive adhesive (dispensed by robot). This is best understood by referring to FIGS. 48 and 49, which shows that a pocket 248 and 248a are first formed at the time of manufacturing the ferrule 216 of the hermetic seal subassembly 210. These pockets can be rectangular (as shown), can be rectangular with rounded ends or it can be round holes as illustrated as 248a or even a continuous groove or slot as illustrated in FIG. 53 as 248c. Into these pockets or grooves 248 can be placed a noble wire 218 as previously described in FIG. 25, or a material 250, such as CuSiI or TiCuSiI, gold or any other material as disclosed earlier that can form a metallurgically sound bond to titanium while at the same time, providing an oxide resistant surface to which electrical attachment 222 can form a solid bond.

Figure 48:
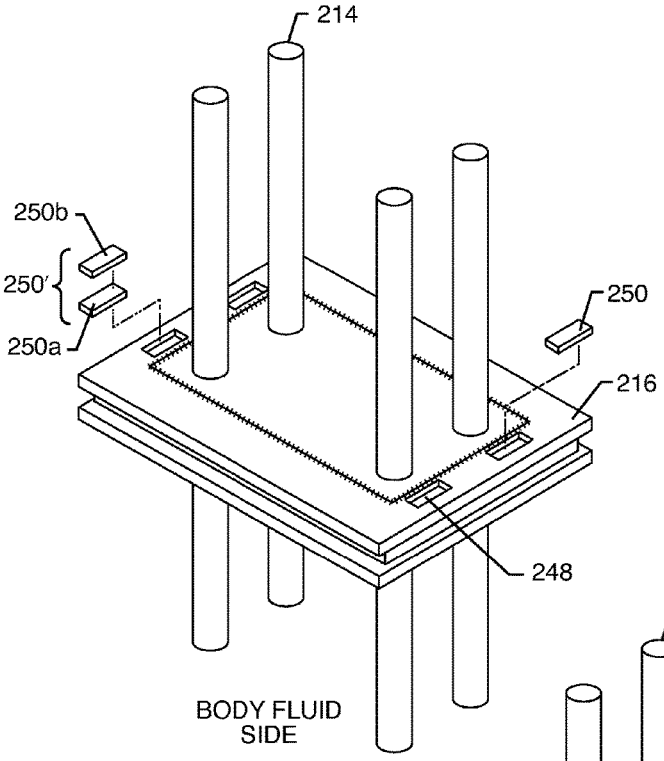
FIG. 48 is a perspective view of another exemplary feedthrough embodying the present invention now showing novel rectangular ground attachments in the ferrule.

Referring once again to FIG. 49, one can see that there is an alternative arrangement similar to that previously described in FIG. 48. In this case, a circular gold braze pre-form 250Ab could first be placed into the counter-bore hole 248a and then a platinum or equivalent cap 250Aa could be placed over it. These could all be reflowed into place leaving a convenient area to make electrical attachment between the capacitor external ground metallization 223, through the oxide resistant pad 250Aa, through the braze material 250Ab and, in turn, to the ferrule 216.

Figure 50:
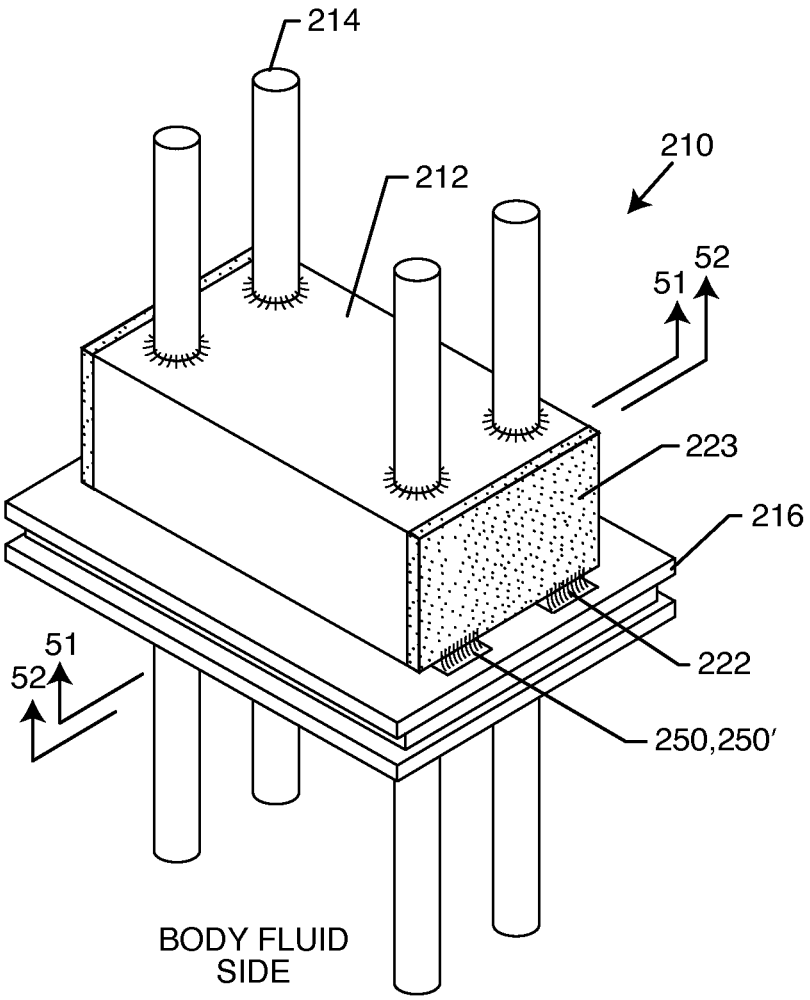
FIG. 50 is similar to either FIG. 48 or 49 now showing the capacitor grounded to the ferrule.

FIG. 50 is an isometric view of the quad polar feedthrough capacitor 212 shown mounted to the hermetically sealed ferrule assembly previously illustrated in FIG. 48. Shown is an electrical attachment material 222 between the capacitor ground metallization 223 that connects to the oxide resistant connection pads 250, 250'. Referring once again to FIG. 50, one can see that there is metallization 223 on both short ends of the capacitor 212. This metallization 223 could extend along the long sides or, alternatively, along all perimeter sides of the capacitor. In the case where the length of the perimeter metallization 223 is made longer, then additional pockets and oxide resistant pads 250 would be required.

FIGS. 51 and 52 illustrate the ground and active electrode plate sets of the capacitor 212 previously illustrated in FIG. 50. In FIG. 51, shown is that the ground electrode plate 230 does not make contact with any of the terminal pins 214. The metallization 223 contacts the ground electrode plate set 230 on its left and right ends. FIG. 52 illustrates the active electrode plates 232. In this case, the active electrode plates 232 are connected to each one of the feedthrough terminal pins 214.

Figure 49:
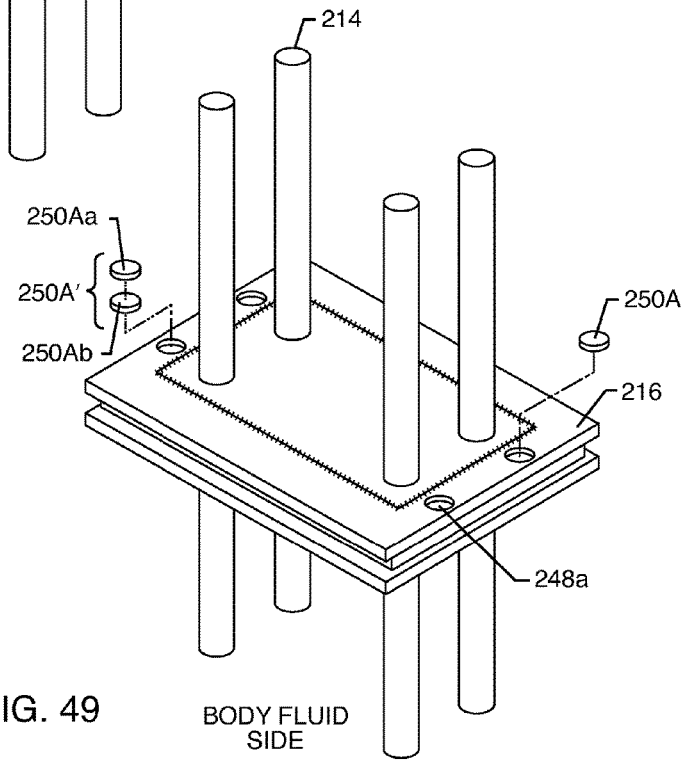
FIG. 49 is a perspective view of another exemplary feedthrough embodying the present invention now showing novel circular ground attachments in the ferrule.

FIG. 53 is the same ferrule as previously described in FIGS. 49 and 50 except that instead of a discrete number of machined pads 248, there is a continuous groove 248c formed around the entire perimeter of the capacitor. This would be filled with a gold braze, Cu—SiI or Ti—Cu—SiI or other material previously listed to form an oxide resistant connection area for the feedthrough capacitor (not shown). A feedthrough capacitor 212, in this case, would have perimeter metallization 223 along all four of its perimeter sides and either a continuous or a multiplicity of short electrical connections 222 would be made between the capacitor metallization 223 and the gold braze or equivalent material that has been flowed in the trough 248c (not shown).

Figure 54:
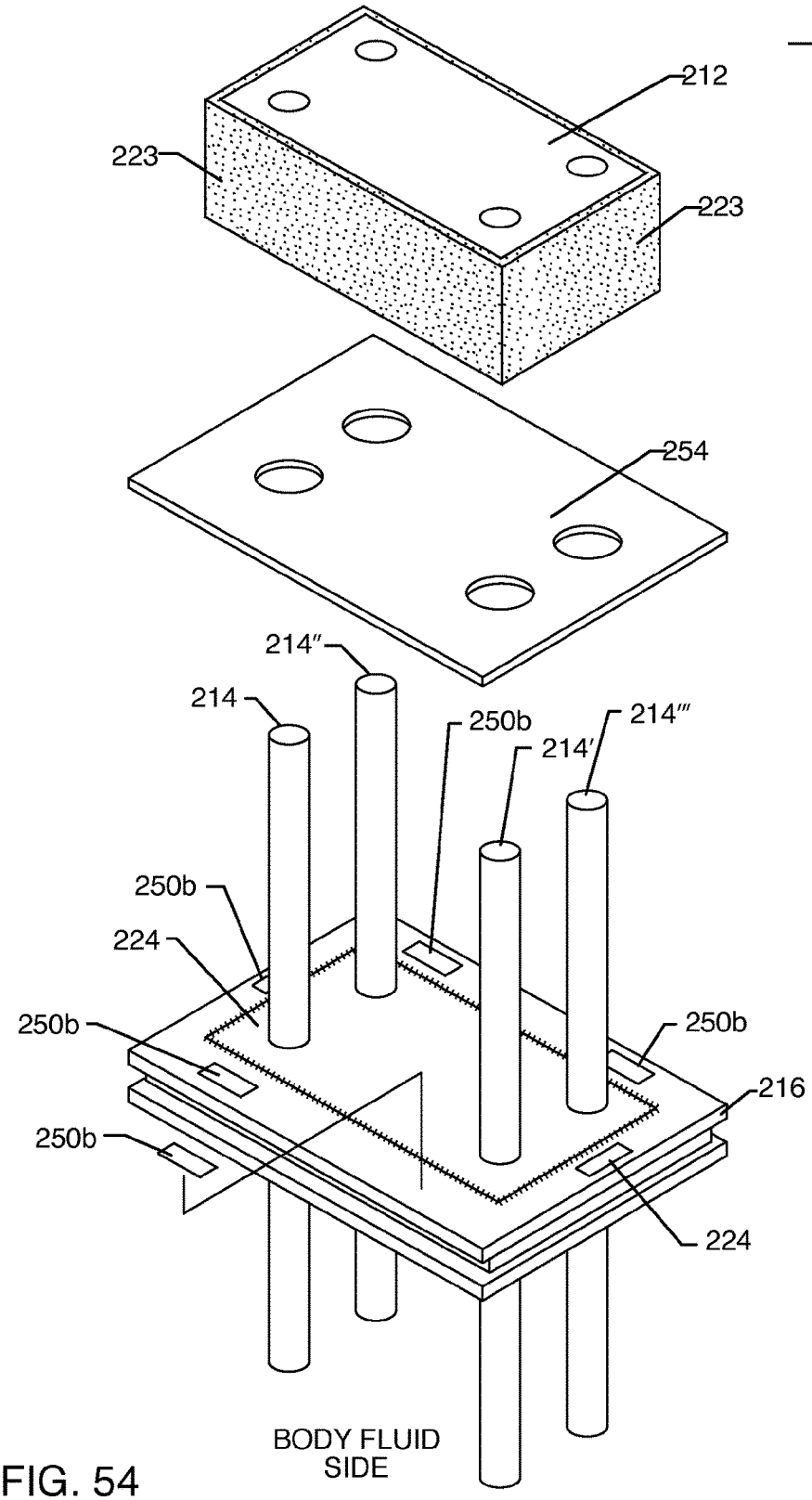
FIG. 54 is an exploded view of another exemplary feedthrough capacitor embodying the present invention now showing novel ground attachment plate.
Figure 55:
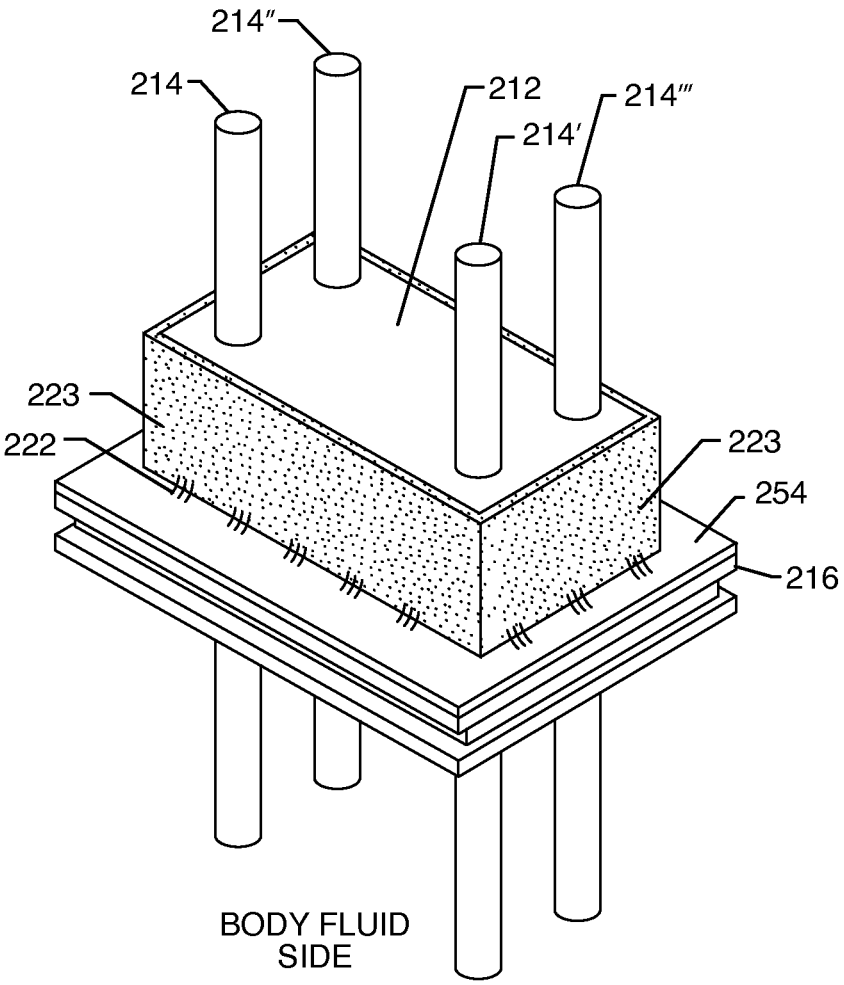
FIG. 55 is the perspective assembled view of the structure of FIG. 54 showing the capacitor metallization grounded to the novel plate.

FIGS. 54 and 55 are yet another embodiment of the present invention. As shown in FIG. 54, gold films 250b may be placed on top of the ferrule 216. Then a conductive sheet 254 is laid overtop the gold films 250b. In a brazing procedure the gold films or plates bond between the conductive sheet 254 and the ferrule 216. The capacitor 212 can be placed overtop the conductive sheet 254 and then an electrical connection using conductive adhesives 222 can be made between the external metallization 223 and the conductive sheet 254. As shown in FIGS. 54 and 55, the metallization is around the entirety of the capacitor 212. This design would also reduce both the inductance and equivalent series resistance of the capacitor 212.

Although several embodiments have been described in detail for purposes of illustration, various modifications may be made to each without departing from the scope and spirit of the invention. Various features of one embodiment may be incorporated into another embodiment, as each embodiment is not exclusive of the other features taught and shown herein. Accordingly, the invention is not to be limited, except as by the appended claims.

What is claimed is:

1. A hermetically sealed filtered feedthrough assembly for an implantable medical device, the filtered feedthrough assembly comprising:

a) an insulator of electrically non-conductive material, the insulator comprising an [outer] insulator *outer* surface extending longitudinally from [a first] *an* insulator *first* end to [a second] *an* insulator *second* end, wherein the insulator has at least one conductor bore extending there through to the [first and second] insulator *first and second* ends;

b) a ferrule of an electrically conductive material, the ferrule comprising a ferrule sidewall defining a ferrule opening, wherein the insulator is hermetically sealed to the conductive ferrule sidewall in the ferrule opening;

c) a conductor comprising an electrically conductive material extending from a [first] conductor *first* end to a [second] conductor *second* end, wherein the conductor is hermetically sealed and disposed through the *at least one* conductor bore in the insulator and in a non-conductive relation with the conductive ferrule;

d) a filter capacitor, comprising:

i) a dielectric comprising [an outer] *a* dielectric *outer* surface extending longitudinally from a [first] dielectric *first* end to a [second] dielectric *second* end;

ii) at least one active electrode plate supported by the dielectric in an interleaved, partially overlapping relationship with at least one ground electrode plate; and iii) at least one terminal pin bore extending through the dielectric to the [first and second] dielectric *first and second* ends, iv) wherein the [second] dielectric *second* end is disposed adjacent to the [first] insulator *first* end;

e) a first metallization electrically contacted to the at least one active electrode plate in the terminal [in] *pin* bore;

f) a first electrical connection electrically coupling the first metallization to the conductor extending through the terminal pin bore in the dielectric;

g) a second metallization electrically contacted to the at least one ground electrode plate at at least a portion of the [outer] dielectric *outer* surface; and h) a second electrical connection electrically coupling the second metallization to the ferrule, wherein the second electrical connection comprises:

i) at least one [oxide-resistant metal] *noble-metal* addition supported by the ferrule adjacent to the second metallization, *wherein the noble-metal metal addition is selected from the group consisting of gold, platinum, palladium, silver, and combinations thereof*;

ii) a first conductive material electrically and physically coupling a first portion of the [oxide-resistant metal] *at least one noble-metal* addition directly to the ferrule; and iii) a second conductive material electrically and physically coupling a second portion of the [oxide-resistant metal] *at least one noble-metal* addition to the second metallization at the [outer] dielectric *outer* surface of the filter capacitor, iv) wherein the first and second conductive materials are different.

2. The assembly of claim 1, wherein the [oxide-resistant metal] *at least one noble-metal* addition comprises a different material as compared to the ferrule.

[3. The assembly of claim 1, wherein the oxide-resistant metal addition comprises a noble metal.]

[4. The assembly of claim 1, wherein the oxide-resistant metal addition is selected from the group consisting of gold, platinum, palladium, silver, and combinations thereof.]

5. The assembly of claim 1, wherein the first conductive material is a weld portion of the [oxide-resistant metal] *at least one noble-metal* addition electrically and physically coupling to the ferrule.

6. The assembly of claim 1, wherein the first conductive material comprises a brazed metal electrically and physically coupling the [oxide-resistant metal] *the at least one noble-metal* addition to the ferrule.

7. The assembly of claim 6, wherein the brazed metal [comprising the oxide-resistant metal addition] is selected from the group consisting of gold, gold-based metal, platinum, platinum based metal, palladium, palladium based metal, silver, silver based metal, gold-palladium, gold-boron, and palladium silver.

8. The assembly of claim 1, wherein the conductor comprises a leadwire.

9. The assembly of claim 8, wherein the leadwire is selected from the group consisting of platinum, palladium, silver, and gold.

10. The assembly of claim 1, wherein the first side of the insulator is flush with the ferrule adjacent to the [second] dielectric *second* end of the filter capacitor.

11. The assembly of claim 1, wherein the insulator comprises an alumina substrate comprised of at least 96% alumina and the conductor comprises a substantially closed pore and substantially pure platinum fill disposed within the conductor bore and extending from the [first] insulator *first* end to the [second] insulator *second* end of the alumina substrate.

12. The assembly of claim 11, wherein the platinum fill forms a tortuous and mutually conformal knitline or interface at the hermetic seal to the alumina substrate comprising the insulator, and wherein the hermetic seal has a leak rate that is no greater than $1\times10^{-7}$ std cc He/sec.

13. The assembly of claim 12, wherein the alumina dielectric substrate and the platinum fill are characterized as the alumina dielectric substrate being in a green state having a first inherent shrink rate during a heat treatment that is greater than a second inherent shrink rate of the platinum fill in the green state during the heat treatment.

14. The assembly of claim 1, wherein the [oxide-resistant metal] *the at least one noble-metal* addition is selected from the group consisting of a wire, a pad, an L-shaped pad, and an L-shaped pad with cutouts.

15. The assembly of claim 1, including a ground wire disposed through both the insulator and the dielectric of the filter capacitor, where the ground wire is not electrically coupled to the at least one active and ground electrode plates, but is electrically coupled to the ferrule.

16. The assembly of claim 15, wherein the ferrule comprises an integrally formed conductive peninsula, and wherein the ground wire is electrically coupled to the peninsula.

17. The assembly of claim 1, wherein the feedthrough capacitor has a resonant frequency above 400 MHz.

18. The assembly of claim 1, wherein the feedthrough capacitor has a capacitance of from 300 picofarads to 10,000 picofarads.

19. The assembly of claim 1, wherein the second conductive material is selected from a solder and a thermal-setting conductive adhesive.

20. The assembly of claim 1, wherein the [first and second] conductor *first and second* ends are spaced from the respective [first and second] insulator *first and second* ends.

21. The assembly of claim 1, wherein the at least one [oxide-resistant metal] *noble-metal* addition is received in a pocket in the ferrule.

22. A hermetically sealed filtered feedthrough assembly for an implantable medical device, the filtered feedthrough assembly comprising:

a) a ferrule comprising a conductive peninsula or extension;

b) an insulator hermetically sealed to the conductive ferrule;

c) a conductor hermetically sealed and disposed through the insulator in non-conductive relation to the conductive ferrule between a body fluid side and a device side;

d) a feedthrough capacitor located on the device side, the feedthrough capacitor comprising a first and a second end metallization, wherein the first end metallization is connected to at least one active electrode plate and wherein the second end metallization is connected to at least one ground electrode plate, wherein the at least one active electrode plate is interleaved and disposed parallel to the at least one ground electrode plate, wherein the at least one active and ground electrode plates are disposed within a capacitor dielectric;

e) a first low impedance electrical connection between the first end metallization and the conductor;

f) a ground conductor disposed through the feedthrough capacitor in non-conductive relation with the at least one ground and active electrode plates, where the ground conductor is electrically coupled to the conductive [peninsular] *peninsula* or extension; and g) an oxide-resistant metal addition attached directly at one end to the ground conductor and connected at the other end to the second end metallization of the feedthrough capacitor.

23. A hermetically sealed filtered feedthrough assembly for an implantable medical device, the filtered feedthrough assembly comprising:

a) an insulator of electrically non-conductive material, the insulator comprising an outer insulator surface extending longitudinally from [a first] *an* insulator *first* end to [a second] *an* insulator *second* end, wherein the insulator has at least one conductor bore extending there through to the [first and second] insulator *first and second* ends;

b) a ferrule of an electrically conductive material, the ferrule comprising[,] a ferrule sidewall including a peninsula and defining a ferrule opening, wherein the insulator is hermetically sealed to the conductive ferrule in the ferrule opening;

c) a conductor comprising an electrically conductive material extending from a [first] conductor *first* end to a [second] conductor *second* end, wherein the conductor is hermetically sealed and disposed through the *at least one* conductor bore in the insulator and in a non-conductive relation with the conductive ferrule;

d) a filter capacitor located adjacent to the [first] insulator *first* end, the filter capacitor comprising:

i) a dielectric comprising [an outer] *a* dielectric *outer* surface extending longitudinally from a [first] dielectric *first* end to a [second] dielectric *second* end;

ii) at least one active electrode plate supported by the dielectric in an interleaved, partially overlapping relationship with at least one ground electrode plate; and iii) at least one terminal pin bore extending through the dielectric to the [first and second] dielectric *first and second* ends, iv) wherein the [second] dielectric *second* end is disposed adjacent to the [first] insulator *first* side;

e) a first metallization electrically contacted to the at least one active electrode plate in the terminal pin bore;

f) a first electrical connection electrically coupling the first metallization to the conductor extending through the terminal pin bore in the dielectric;

g) a second metallization electrically contacted to the at least one ground electrode plate at the [outer] dielectric *outer* surface;

h) a ground conductor disposed through the filter capacitor in non-conductive relation with the at least one ground and active electrode plates, wherein the ground conductor is electrically coupled to the conductive peninsula; and i) a second electrical connection electrically coupling the second metallization to the ferrule, wherein the second electrical connection comprises:

i) at least one noble-metal addition supported by the ferrule adjacent to the second metallization, wherein the noble-metal addition is selected from the group consisting of gold, platinum, palladium, silver, and combinations thereof;

ii) a first conductive material electrically and physically coupling a first portion of the [oxide-resistant metal] *noble-metal* addition to the ferrule; and iii) a second conductive material electrically and physically coupling a second portion of the [noble metal] *noble-metal* addition to the second metallization at the outer dielectric surface of the filter capacitor, iv) wherein the first and second conductive materials are different.

24. The assembly of claim 23, wherein the first conductive material is a weld portion of the [oxide-resistant metal] *noble-metal* addition electrically and physically coupling to the ferrule.

25. The assembly of claim 23, wherein the first conductive material comprises a brazed metal electrically and physically coupling the [oxide-resistant metal] *noble-metal* addition to the ferrule.

26. The assembly of claim 23, wherein the second conductive material is selected from a solder and a thermal-setting conductive adhesive.

27. The assembly of claim 23, wherein the second conductive material does not contact the conductive material.

28. An implantable medical device, comprising:

a) a thermally or electrically conductive AIMD housing containing at least one of tissue-stimulating and biological-sensing circuits for the AIMD, wherein the housing has an opening providing passage from a body fluid side outside the housing to a device side inside the housing; and b) a filtered feedthrough assembly hermetically sealed in the housing opening, the filtered feedthrough assembly comprising:

i) an insulator of electrically non-conductive material, the insulator comprising an [outer] insulator *outer* surface extending from [a body fluid side] *an* insulator *body fluid side* end to [a device side] *an* insulator *device side* end, wherein the insulator has at least one conductor bore extending there through to the [body fluid and device side] insulator *body fluid and device side* ends;

ii) a ferrule of an electrically conductive material electrically and physically connected to the housing in the housing opening, the ferrule comprising a ferrule sidewall having [an inner] *a* ferrule *inner* sidewall surface defining a ferrule opening and [an outer] *a* ferrule *outer* sidewall surface hermetically sealed to the device housing, wherein the insulator is received in the ferrule opening and hermetically sealed to the ferrule at the [inner] ferrule *inner* surface;

iii) a conductor comprising an electrically conductive material extending from a [body fluid side] conductor *body fluid side* end to a [device side] conductor *device side* end, wherein the conductor is hermetically sealed and disposed through the *at least one* conductor bore in the insulator and in a non-conductive relation with the conductive ferrule;

iv) a filter capacitor, comprising:

A) a dielectric comprising [an outer] *a* dielectric *outer* surface extending from a [first] dielectric *first* end to a [second] dielectric *second* end;

B) at least one active electrode plate supported by the dielectric in an interleaved, partially overlapping relationship with at least one ground electrode plate; and C) at least one terminal pin bore extending through the dielectric to the [first and second] dielectric *first and second* ends, D) wherein the second end of the capacitor dielectric is located adjacent to the device side of the insulator;

v) a first metallization electrically contacted to the at least one active electrode plate in the terminal pin bore;

vi) a first electrical connection electrically coupling the first metallization to the conductor in the terminal pin bore extending through the dielectric;

vii) a second metallization electrically contacted to the at least one ground electrode plate at the [outer] dielectric *outer* surface; and viii) a second electrical connection electrically coupling the second metallization to the ferrule, wherein the second electrical connection comprises:

A) at least one [oxide-resistant metal] *noble-metal* addition supported by the ferrule adjacent to the second metallization, *wherein the at least one noble-metal addition is selected from the group consisting of gold, platinum, palladium, silver, and combinations thereof*;

B) a first conductive material electrically and physically coupling a first portion of the [oxide-resistant metal] *at least one noble-metal* addition directly to the ferrule hermetically sealed to the device housing; and C) a second conductive material electrically and physically coupling a second portion of the [oxide-resistant metal] *at least one noble-metal* addition to the second metallization at the [outer] dielectric *outer* surface of the filter capacitor, D) wherein the first and second conductive materials are different.

29. The implantable medical device of claim 28, wherein the first conductive material is a weld portion of the [oxide-resistant metal] *at least one noble-metal* addition electrically and physically coupling to the ferrule.

30. The implantable medical device of claim 28, wherein the first conductive material comprises a brazed metal electrically and physically coupling the [oxide-resistant metal] *at least one noble-metal* addition to the ferrule.

31. The implantable medical device of claim 28, wherein the second conductive material is selected from a solder and a thermal-setting conductive adhesive.

32. The implantable medical device of claim 28, wherein the second conductive material[,] does not contact the ferrule.

33. A hermetically sealed filtered feedthrough assembly for an implantable medical device, the filtered feedthrough assembly comprising:

a) an insulator of electrically non-conductive material, the insulator comprising an [outer] insulator *outer* surface extending from [a first] *an* insulator *first* end to [a second] *an* insulator *second* end, wherein the insulator has at least one conductor bore extending there through to the [first and second] insulator *first and second* ends;

b) a ferrule of an electrically conductive material, the ferrule comprising a ferrule sidewall defining a ferrule opening, wherein the insulator is hermetically sealed to the conductive ferrule sidewall in the ferrule opening;

c) a conductor comprising an electrically conductive material extending from a [first] conductor *first* end to a [second] conductor *second* end, wherein the conductor is hermetically sealed and disposed through the *at least one* conductor bore in the insulator and in a non-conductive relation with the conductive ferrule;

d) a filter capacitor, comprising:

i) a dielectric comprising [an outer] *a* dielectric *outer* surface extending from a [first] dielectric *first* end to a [second] dielectric *second* end;

ii) at least one active electrode plate supported by the dielectric in an interleaved, partially overlapping relationship with at least one ground electrode plate; and iii) at least one terminal pin bore extending through the dielectric to the [first and second] dielectric *first and second* ends, iv) wherein the [second] dielectric *second* end is disposed adjacent to the [first] insulator *first* end;

e) a first metallization electrically contacted to the at least one active electrode plate in the terminal pin bore;

f) a first electrical connection electrically coupling the first metallization to the conductor extending through the terminal pin bore in the dielectric;

g) a second metallization electrically contacted to the at least one ground electrode plate at the [outer] dielectric *outer* surface; and h) a second electrical connection electrically coupling the second metallization to the ferrule, wherein the second electrical connection comprises:

i) at least one noble-metal addition supported by the ferrule adjacent to the second metallization, wherein the *at least one* noble-metal addition is selected from the group consisting of gold, platinum, palladium, silver, and combinations thereof;

ii) a weld portion of the [oxide-resistant metal] *at least one noble-metal* addition electrically and physically coupling to the ferrule; and iii) a solder or thermal-setting material electrically and physically coupling a second portion of the [oxide-resistant metal] *at least one noble-metal* addition to the second metallization at the [outer] dielectric *outer* surface of the filter capacitor.

* * * * *